(12) United States Patent
Mitchell et al.

(10) Patent No.: US 10,925,628 B2
(45) Date of Patent: Feb. 23, 2021

(54) TISSUE ENGAGEMENT APPARATUS FOR THEAPEUTIC ULTRASOUND APPARATUS AND METHOD

(71) Applicant: Novuson Surgical, Inc., Bothell, WA (US)

(72) Inventors: Stuart B. Mitchell, Bothell, WA (US); Eric Hadford, Bothell, WA (US); Daniel Baker, Bothell, WA (US)

(73) Assignee: Novuson Surgical, Inc., Bothell, WA (US)

( * ) Notice: Subject to any disclaimer, the term of this patent is extended or adjusted under 35 U.S.C. 154(b) by 682 days.

(21) Appl. No.: 15/787,616

(22) Filed: Oct. 18, 2017

(65) Prior Publication Data
US 2019/0083125 A1    Mar. 21, 2019

Related U.S. Application Data

(60) Provisional application No. 62/560,069, filed on Sep. 18, 2017.

(51) Int. Cl.
*A61B 17/068* (2006.01)
*A61B 18/12* (2006.01)
(Continued)

(52) U.S. Cl.
CPC .... *A61B 17/320092* (2013.01); *A61B 17/225* (2013.01); *A61B 17/295* (2013.01);
(Continued)

(58) Field of Classification Search
CPC .............. A61B 17/225; A61B 17/295; A61B 2090/378; A61B 2017/320094;
(Continued)

(56) References Cited

U.S. PATENT DOCUMENTS

| 4,545,386 A | 10/1985 | Hetz et al. |
| 4,601,296 A | 7/1986 | Yerushalmi |

(Continued)

FOREIGN PATENT DOCUMENTS

| JP | 2009-177302 A | 8/2009 |
| WO | WO 2007/021958 A2 | 2/2007 |
| WO | WO 2007/035529 A2 | 3/2007 |

OTHER PUBLICATIONS

Invitation to Pay Additional Fees and, Where Applicable, Protest Fee in PCT Application No. PCT/US18/51215 dated Nov. 8, 2018 in 2 pages.

(Continued)

*Primary Examiner* — Thomas M Dougherty
(74) *Attorney, Agent, or Firm* — BakerHostetler

(57) ABSTRACT

Various devices related to a therapeutic ultrasound device for use during a medical procedure to cauterize tissue are disclosed. The device includes an apparatus for tissue engagement. The apparatus includes a first jaw and a second jaw that each includes a body portion and an ear located adjacent to the body portion. The body portion is configured to receive an acoustic stack and the ear includes a slot configured to receive a first pin. The first and second jaws include an opening located between the body portion and the ear. The opening is configured to receive a second pin such that the first jaw and the second jaw are configured to rotate about the second pin.

24 Claims, 38 Drawing Sheets

(51) Int. Cl.
*H01L 41/09* (2006.01)
*A61B 17/32* (2006.01)
*A61N 7/02* (2006.01)
*A61B 17/295* (2006.01)
*A61B 17/225* (2006.01)
*A61B 17/29* (2006.01)
*A61B 17/28* (2006.01)
*A61B 90/00* (2016.01)
*A61N 7/00* (2006.01)

(52) U.S. Cl.
CPC .............. *A61N 7/02* (2013.01); *A61N 7/022* (2013.01); *A61B 2017/2825* (2013.01); *A61B 2017/2926* (2013.01); *A61B 2017/2929* (2013.01); *A61B 2017/2936* (2013.01); *A61B 2017/320069* (2017.08); *A61B 2017/320094* (2017.08); *A61B 2017/320095* (2017.08); *A61B 2090/378* (2016.02); *A61N 2007/0056* (2013.01); *A61N 2007/0073* (2013.01)

(58) Field of Classification Search
CPC ....... A61B 2018/320069; A61B 2017/320095; A61B 2017/2825; A61B 2017/2926; A61B 2017/2936; A61N 7/022; A61N 2007/0056; A61N 2007/0073; A62B 2017/2929
USPC .......................................... 310/311–371, 800
See application file for complete search history.

(56) References Cited

U.S. PATENT DOCUMENTS

| | | |
|---|---|---|
| 4,611,372 A | 9/1986 | Enjoji et al. |
| 5,762,066 A | 6/1998 | Law et al. |
| 5,895,356 A | 4/1999 | Andrus et al. |
| 6,007,499 A | 12/1999 | Martin et al. |
| 6,226,543 B1 | 5/2001 | Gilboa et al. |
| 6,432,067 B1 | 8/2002 | Martin et al. |
| 6,558,333 B2 | 5/2003 | Gilboa et al. |
| 6,574,498 B1 | 6/2003 | Gilboa |
| 6,679,875 B2 | 1/2004 | Honda et al. |
| 6,711,429 B1 | 3/2004 | Gilboa et al. |
| 6,719,694 B2 | 4/2004 | Weng et al. |
| 6,764,488 B1 | 7/2004 | Burbank et al. |
| 6,996,430 B1 | 2/2006 | Gilboa et al. |
| 7,625,397 B2 | 12/2009 | Foerster et al. |
| 7,668,582 B2 | 2/2010 | Sirimanne et al. |
| 7,806,892 B2 | 10/2010 | Makin et al. |
| 7,833,219 B2 | 11/2010 | Tashiro et al. |
| 7,833,221 B2 | 11/2010 | Voegele et al. |
| 7,846,155 B2 | 12/2010 | Houser et al. |
| 8,023,712 B2 | 9/2011 | Ikuma et al. |
| 8,155,728 B2 | 4/2012 | Voegele et al. |
| 8,204,576 B2 | 6/2012 | Ikuma et al. |
| 8,244,329 B2 | 8/2012 | Su |
| 8,306,602 B2 | 11/2012 | Sirimanne et al. |
| 8,333,721 B2 | 12/2012 | Makin et al. |
| 8,414,494 B2 | 4/2013 | Vaezy et al. |
| 8,500,643 B2 | 8/2013 | Curra et al. |
| 8,701,035 B2 | 4/2014 | Hibi et al. |
| 8,852,113 B2 | 10/2014 | Nishina et al. |
| 8,900,145 B2 | 12/2014 | Curra et al. |
| 8,900,152 B2 | 12/2014 | Ogawa et al. |
| 9,005,144 B2 | 4/2015 | Slayton et al. |
| 9,198,635 B2 | 12/2015 | Crum et al. |
| 2002/0007118 A1 | 1/2002 | Adachi et al. |
| 2002/0068866 A1 | 6/2002 | Zikorus et al. |
| 2002/0115917 A1 | 8/2002 | Honda et al. |
| 2003/0013960 A1 | 1/2003 | Makin et al. |
| 2003/0013972 A1 | 1/2003 | Makin |
| 2003/0018270 A1 | 1/2003 | Makin et al. |
| 2003/0032898 A1 | 2/2003 | Makin et al. |
| 2004/0059220 A1 | 3/2004 | Mourad et al. |
| 2004/0242992 A1 | 12/2004 | Hereyama |
| 2005/0261585 A1 | 11/2005 | Makin et al. |
| 2006/0129146 A1 | 6/2006 | Dycus et al. |
| 2006/0183972 A1 | 8/2006 | Tashiro et al. |
| 2007/0205698 A1 | 9/2007 | Chaggares et al. |
| 2008/0086051 A1 | 4/2008 | Voegele |
| 2008/0221444 A1 | 9/2008 | Ritchie et al. |
| 2008/0269614 A1 | 10/2008 | Adachi et al. |
| 2008/0281189 A1 | 11/2008 | Komuro |
| 2008/0306379 A1 | 12/2008 | Ikuma et al. |
| 2009/0005689 A1 | 1/2009 | Kodama et al. |
| 2009/0054761 A1 | 2/2009 | Voegele et al. |
| 2009/0093726 A1 | 4/2009 | Takayama |
| 2009/0175518 A1 | 7/2009 | Ikuma et al. |
| 2009/0221911 A1 | 9/2009 | Igarashi |
| 2009/0318813 A1 | 12/2009 | Thompson et al. |
| 2009/0318954 A1 | 12/2009 | Johnson et al. |
| 2010/0063401 A1 | 3/2010 | Nishina et al. |
| 2010/0198048 A1 | 8/2010 | Togawa |
| 2010/0256499 A1 | 10/2010 | Imahashi |
| 2011/0015631 A1 | 1/2011 | Wiener et al. |
| 2011/0021907 A1 | 1/2011 | Igarashi |
| 2011/0073114 A1 | 3/2011 | Su |
| 2011/0130773 A1 | 6/2011 | Saliman et al. |
| 2011/0237934 A1 | 9/2011 | Onishi |
| 2012/0059247 A1 | 3/2012 | Speeg et al. |
| 2012/0265057 A1 | 10/2012 | Nishina et al. |
| 2012/0283555 A1 | 11/2012 | Su |
| 2013/0066195 A1 | 3/2013 | Sirimanne et al. |
| 2013/0137990 A1 | 5/2013 | Tsuruta |
| 2013/0267839 A1 | 10/2013 | Lin et al. |
| 2013/0310684 A1 | 11/2013 | Takachi |
| 2013/0317351 A1 | 11/2013 | Case et al. |
| 2013/0317352 A1 | 11/2013 | Case et al. |
| 2013/0317353 A1 | 11/2013 | Frank et al. |
| 2013/0345551 A1 | 12/2013 | Arts et al. |
| 2014/0018668 A1 | 1/2014 | Zheng et al. |
| 2014/0046174 A1 | 2/2014 | Ladtkow et al. |
| 2014/0046175 A1 | 2/2014 | Ladtkow et al. |
| 2014/0046176 A1 | 2/2014 | Ladtkow et al. |
| 2014/0107474 A1 | 4/2014 | Ogawa et al. |
| 2014/0114195 A1 | 4/2014 | Inui et al. |
| 2014/0135805 A1 | 5/2014 | Windgassen et al. |
| 2014/0228680 A1 | 8/2014 | Fukuda |
| 2014/0252917 A1 | 9/2014 | Nishie et al. |
| 2014/0275994 A1 | 9/2014 | Liu et al. |
| 2015/0005634 A1 | 1/2015 | Curra et al. |
| 2015/0011891 A1 | 1/2015 | Yamada |
| 2015/0073267 A1 | 3/2015 | Brannan et al. |
| 2015/0141810 A1 | 5/2015 | Weadock |
| 2015/0173590 A1 | 6/2015 | Fujimura |
| 2015/0173711 A1 | 6/2015 | Hiraoka |
| 2015/0201964 A1 | 7/2015 | Murdeshwar et al. |
| 2015/0305711 A1 | 10/2015 | Ogawa |
| 2015/0359517 A1 | 12/2015 | Tan |
| 2016/0030014 A1 | 2/2016 | McWeeney et al. |
| 2016/0030015 A1 | 2/2016 | McWeeney et al. |
| 2016/0030017 A1 | 2/2016 | McWeeney |
| 2016/0051221 A1 | 2/2016 | Dickhans et al. |
| 2016/0128669 A1 | 5/2016 | Hill et al. |
| 2016/0199047 A1 | 7/2016 | McWeeney et al. |
| 2016/0302688 A1 | 10/2016 | Podhajsky |
| 2016/0372848 A1 | 12/2016 | Yamada |
| 2016/0374761 A1 | 12/2016 | Frank et al. |
| 2016/0374762 A1 | 12/2016 | Case et al. |
| 2017/0265933 A1* | 9/2017 | Yates ................. A61B 18/1445 |
| 2019/0216492 A1* | 7/2019 | Meiser ............... A61B 18/1442 |
| 2020/0138435 A1* | 5/2020 | Shelton, IV ......... A61B 17/072 |

OTHER PUBLICATIONS

International Patent Application No. PCT/US2018/051215; Int'l Preliminary Report on Patentability; dated Apr. 2, 2020; 10 pages.
International Search Report in PCT/US2006/031414 dated Mar. 26, 2007 (WO 2007/021958).
International Search Report in PCT/US2006/036106 dated Jun. 6, 2008 (WO 2007/035529).

(56) References Cited

OTHER PUBLICATIONS

Accord, Ryan E., et al., The Issue of Transmurality in Surgical Ablation for Atrial Fibrillation, Cardiothoracic Surgery Network; Aug. 8, 2005.
Wissler, Eugene H., Pennes' 1948 paper revisited; 50 years of JAP, American Physiological Society, pp. 35-41; 1998.

* cited by examiner

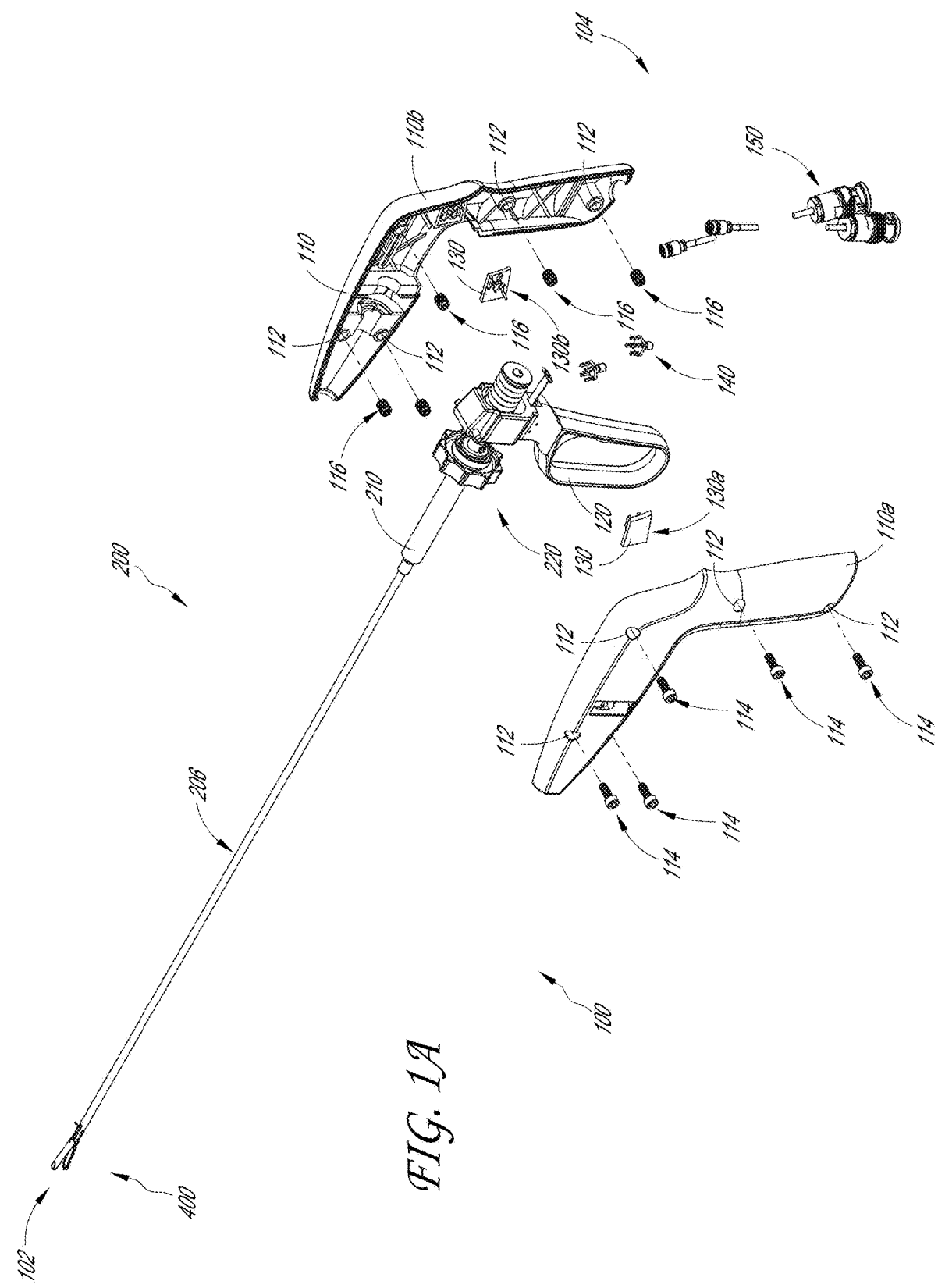

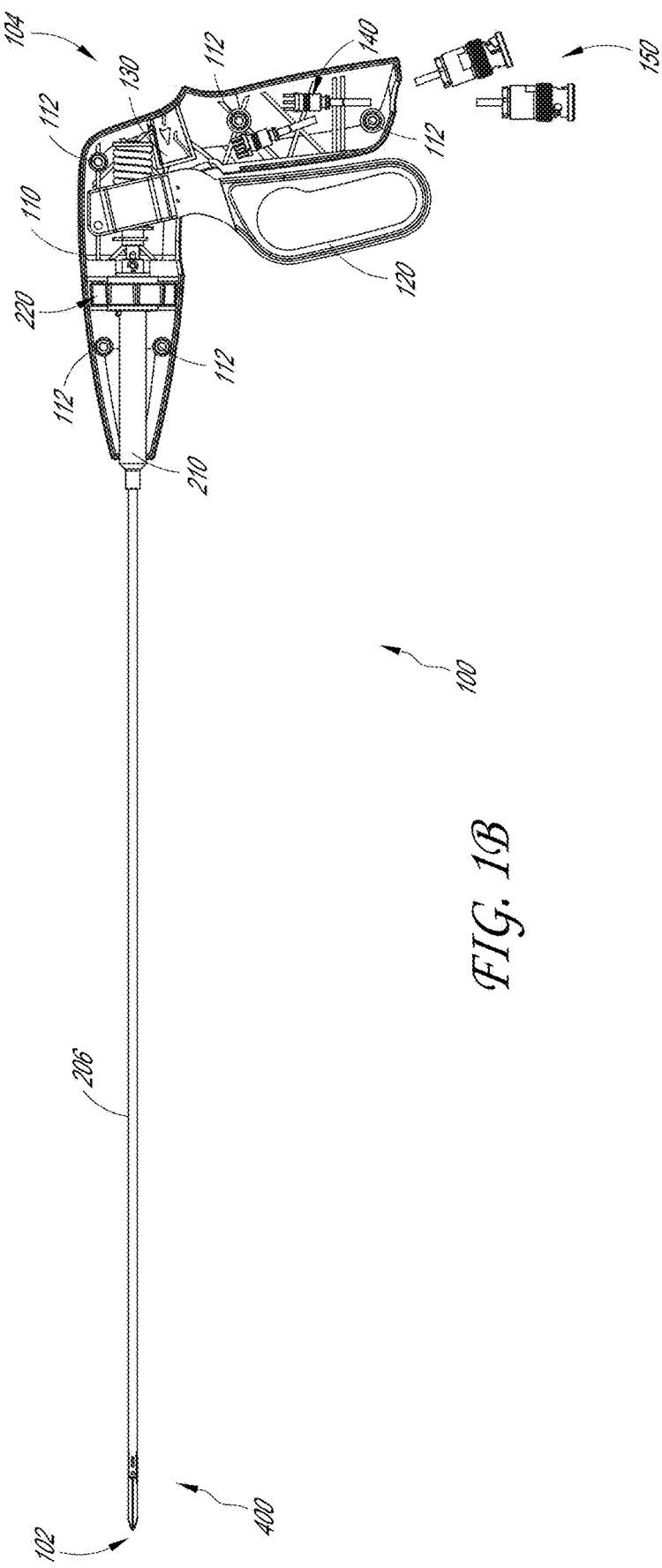

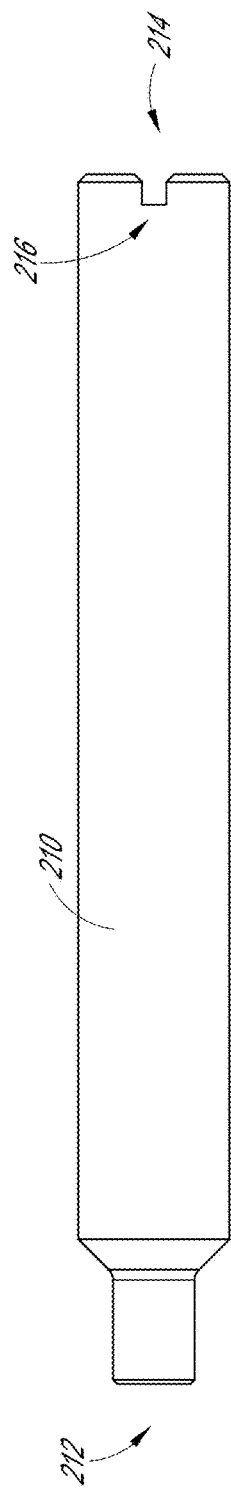
FIG. 2E
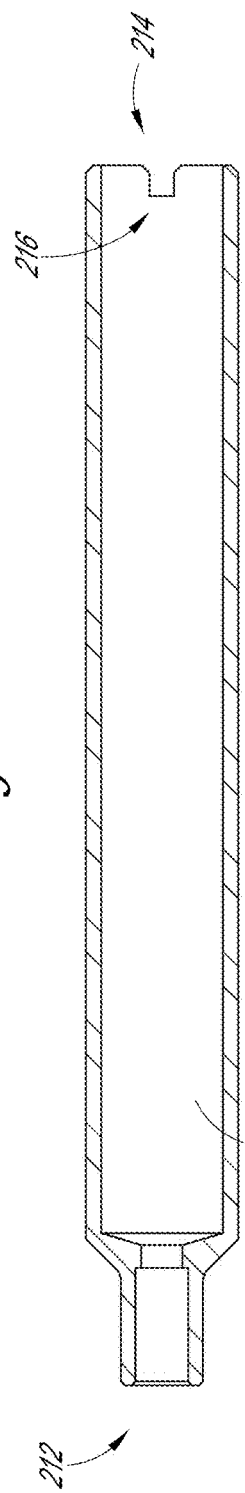
FIG. 2F
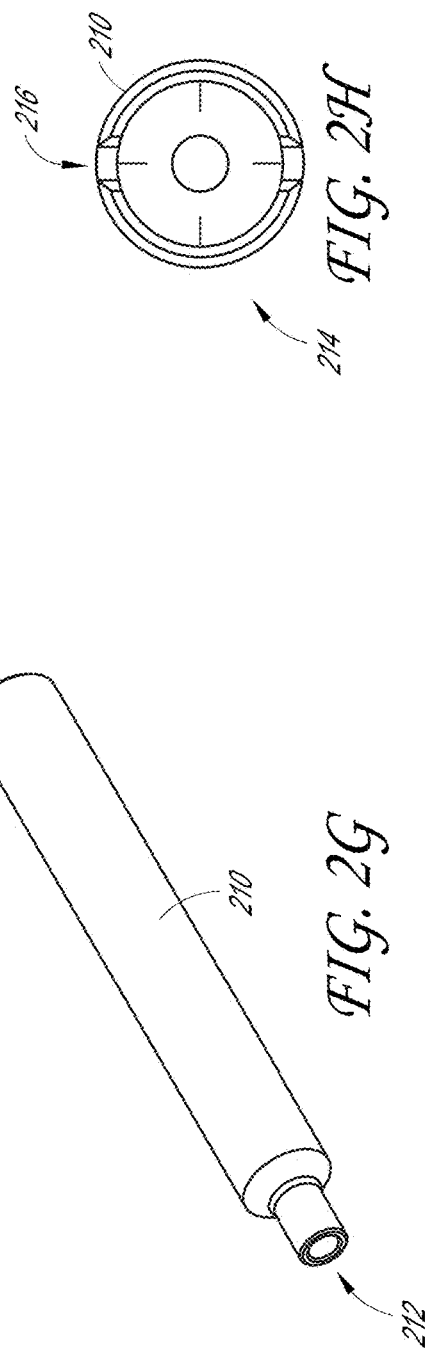
FIG. 2H
FIG. 2G

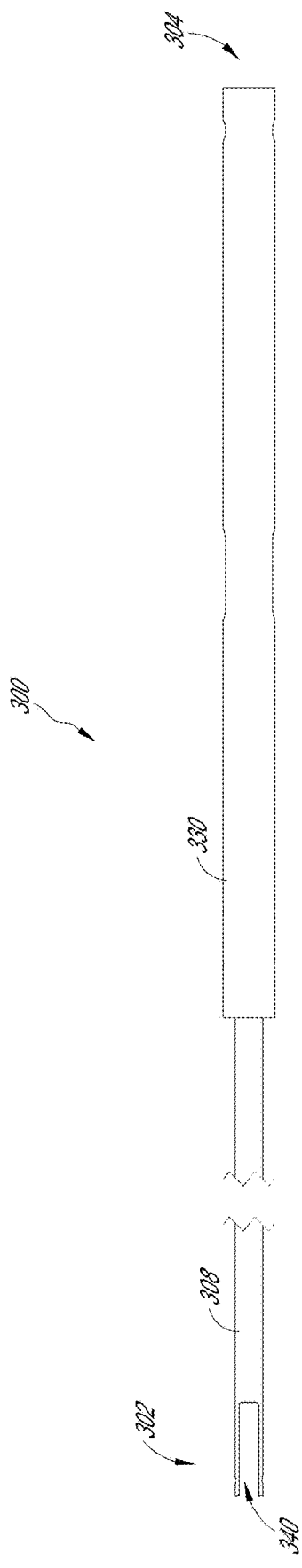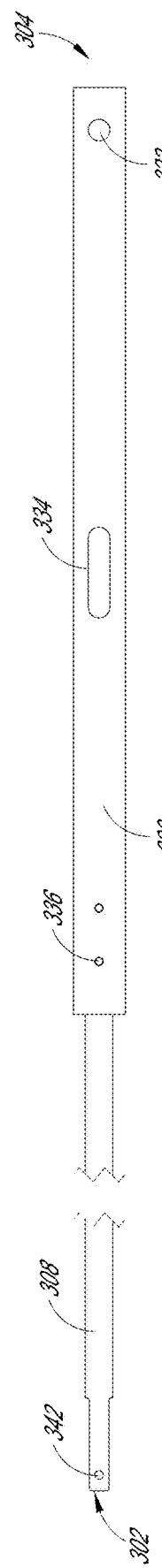

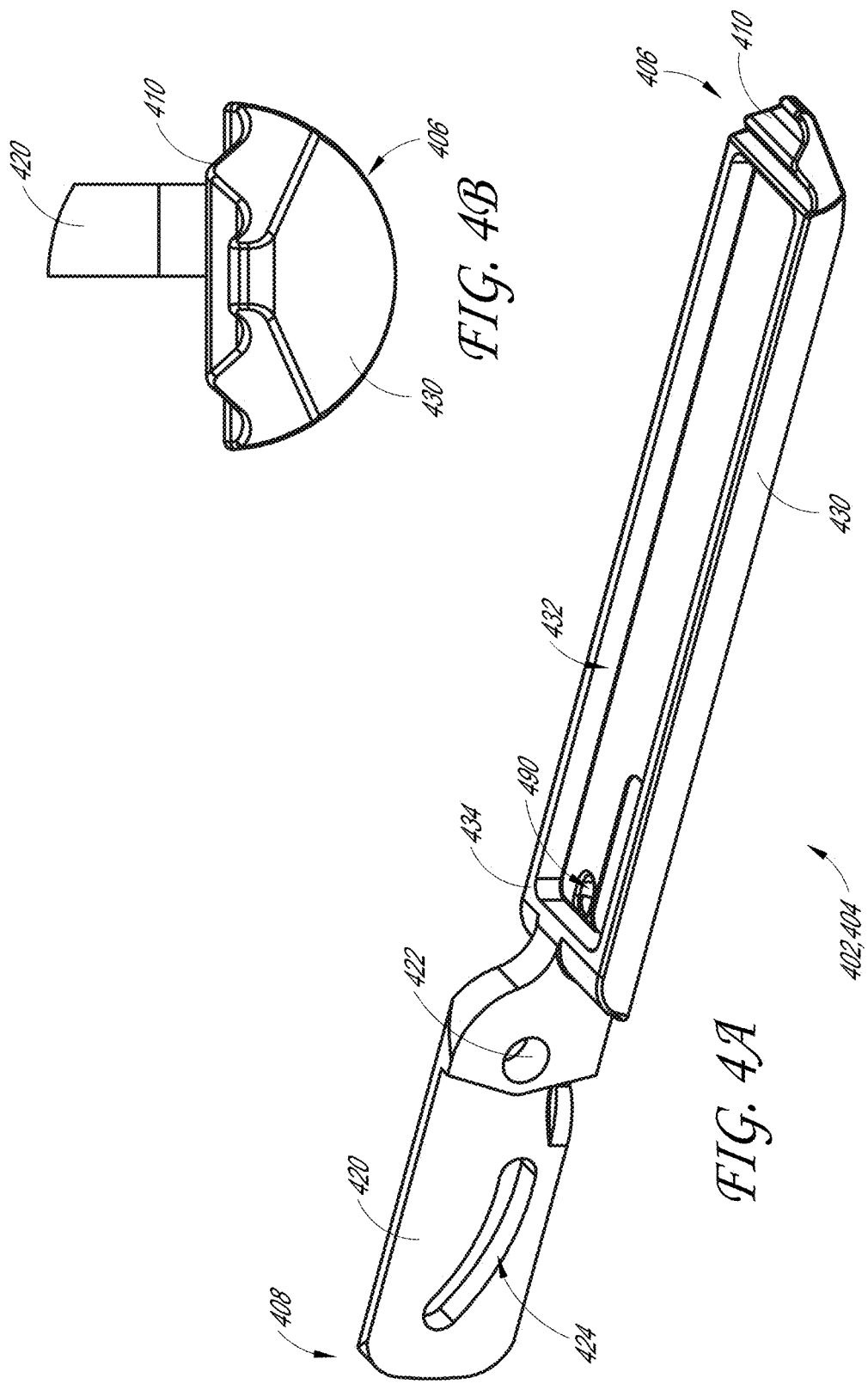

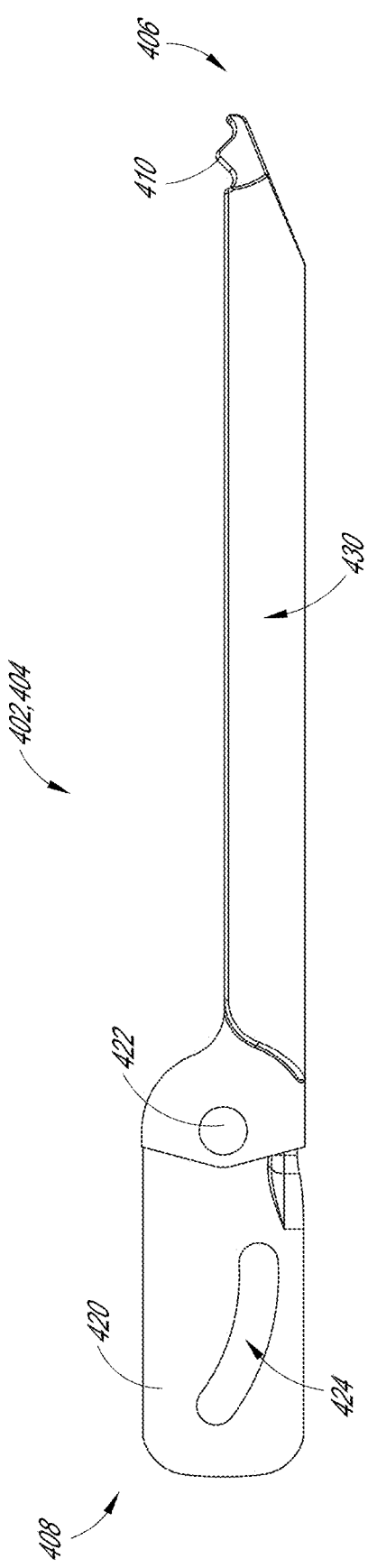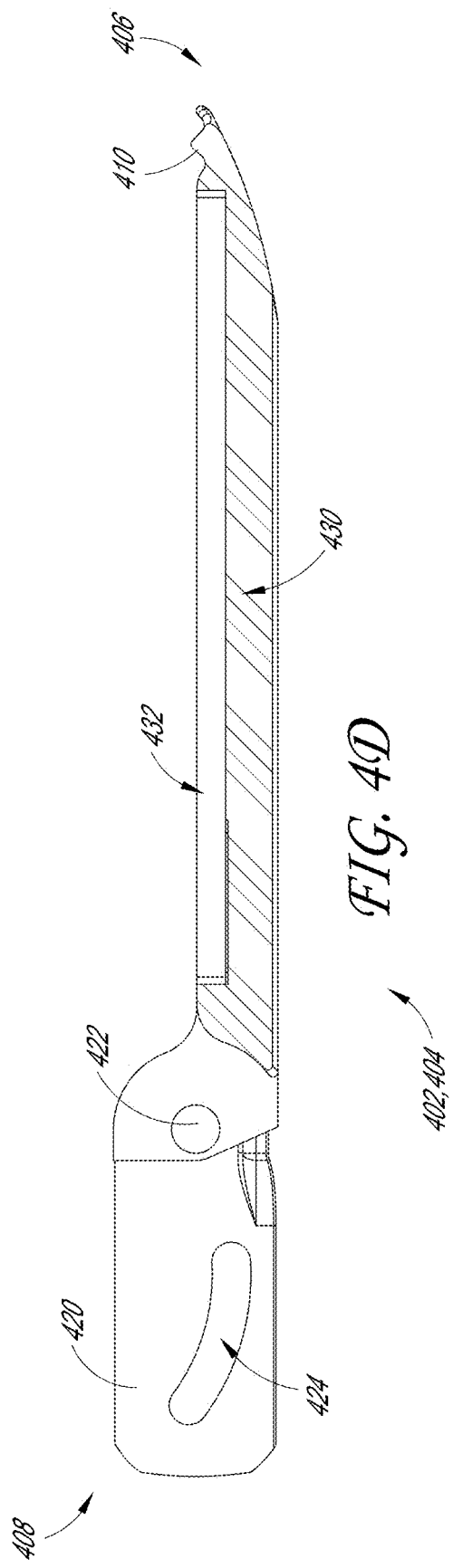

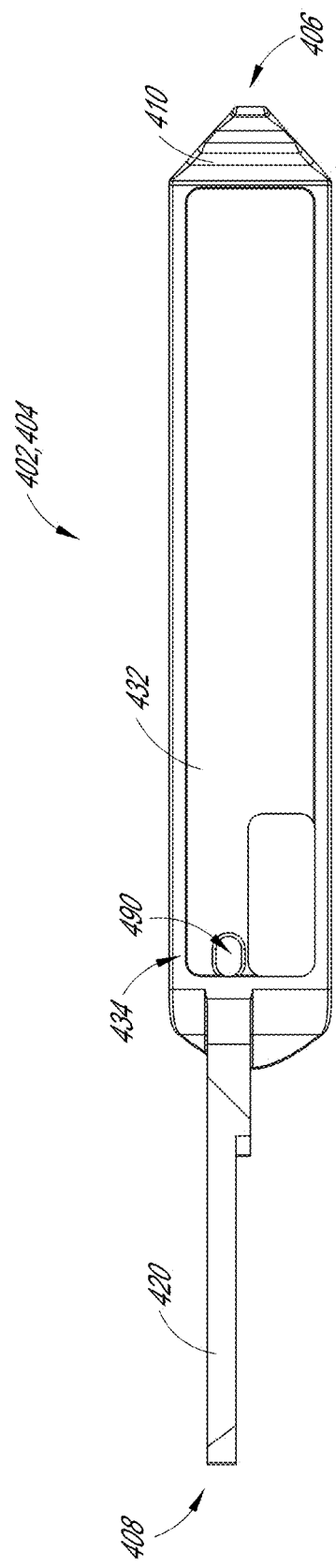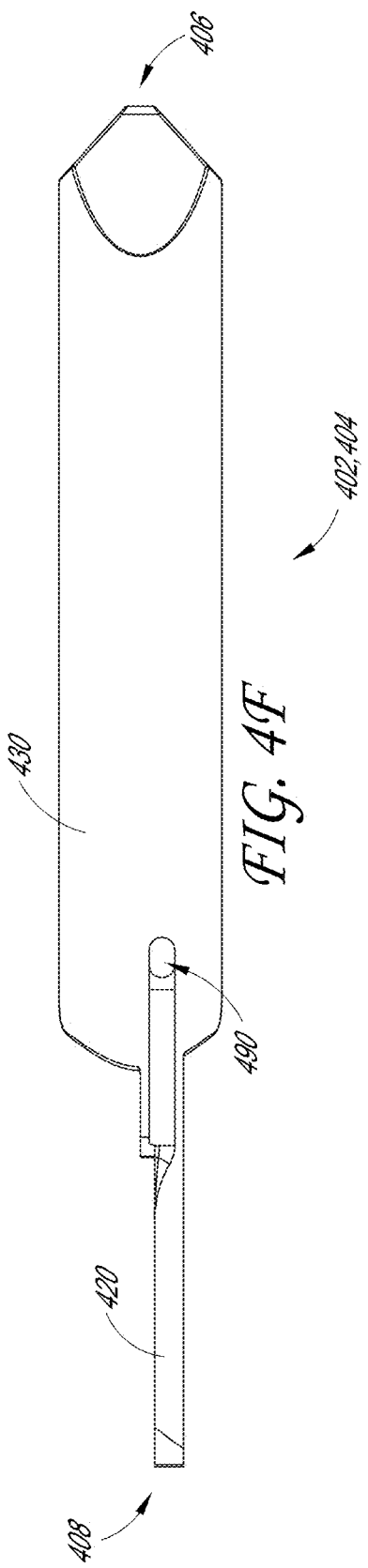

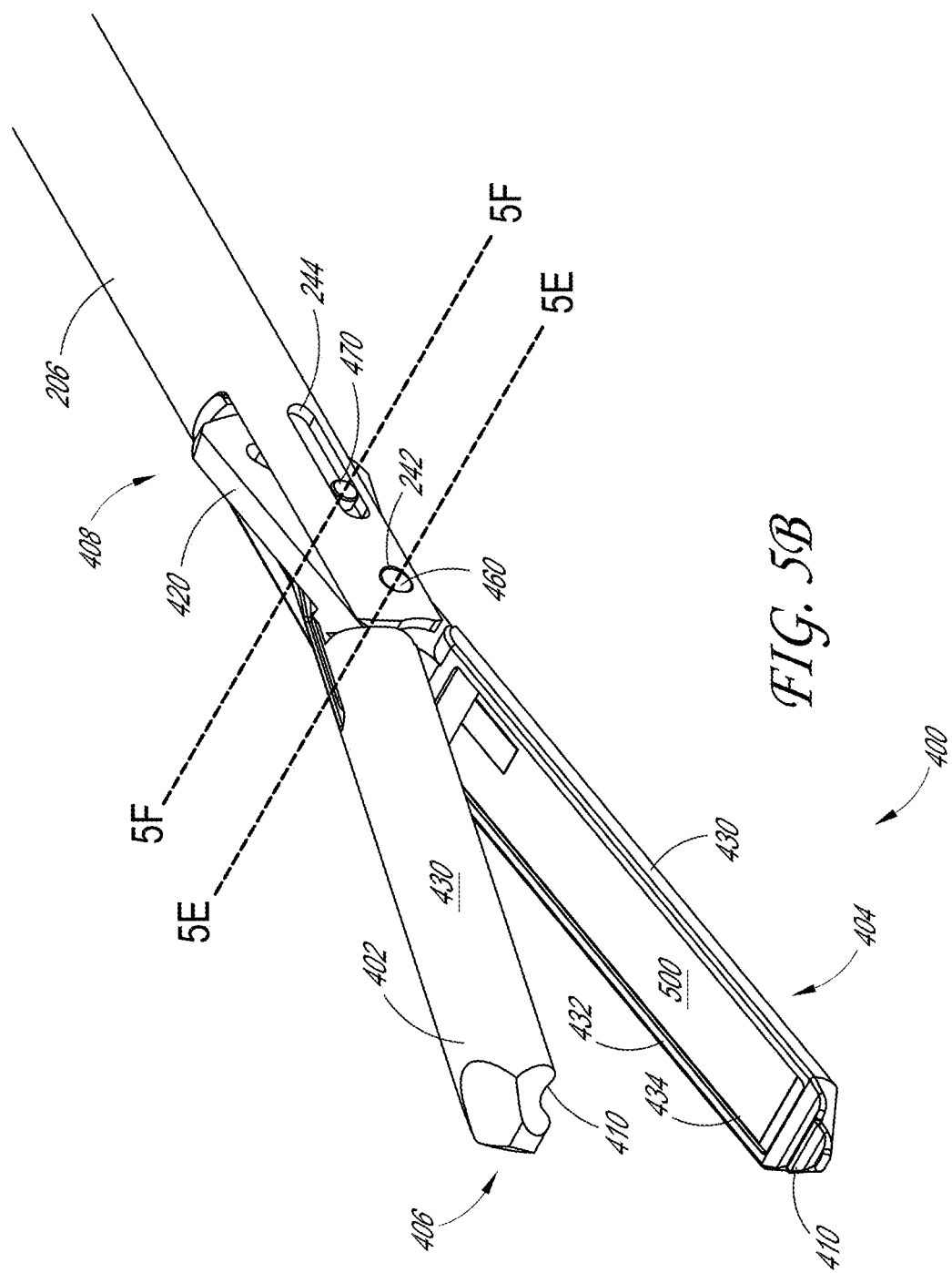

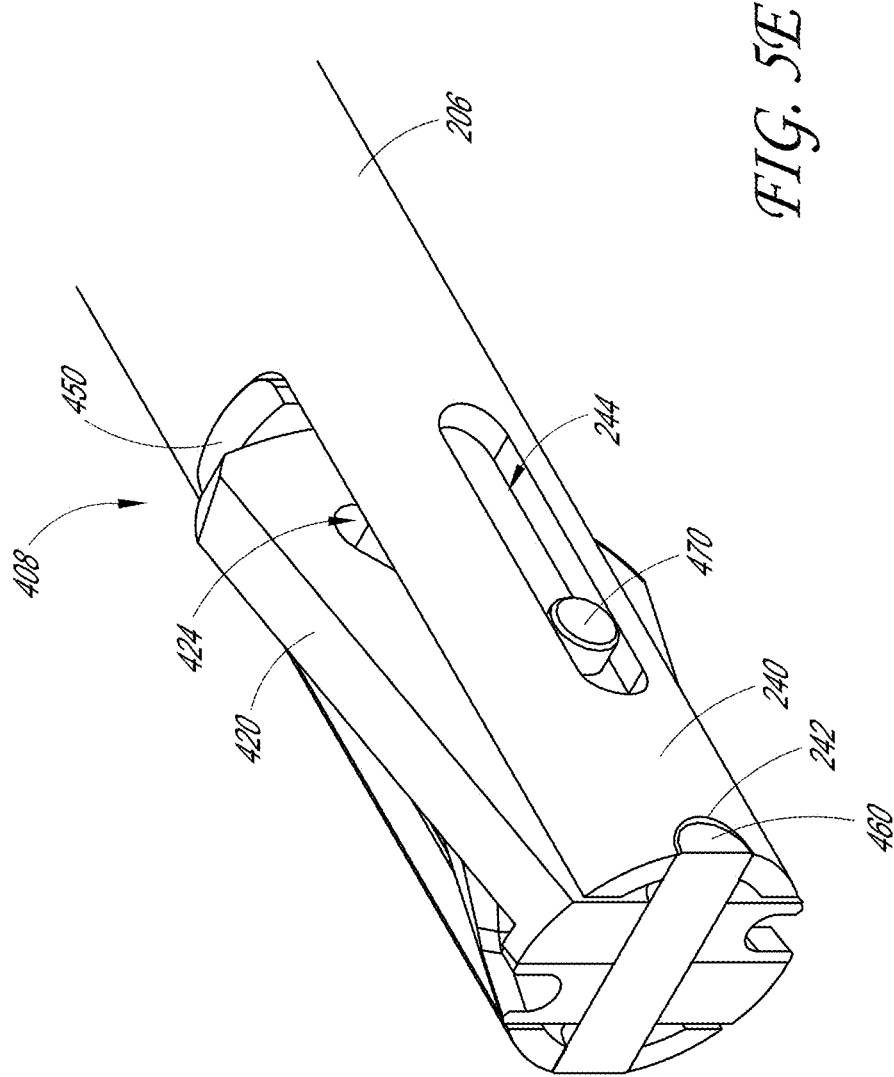

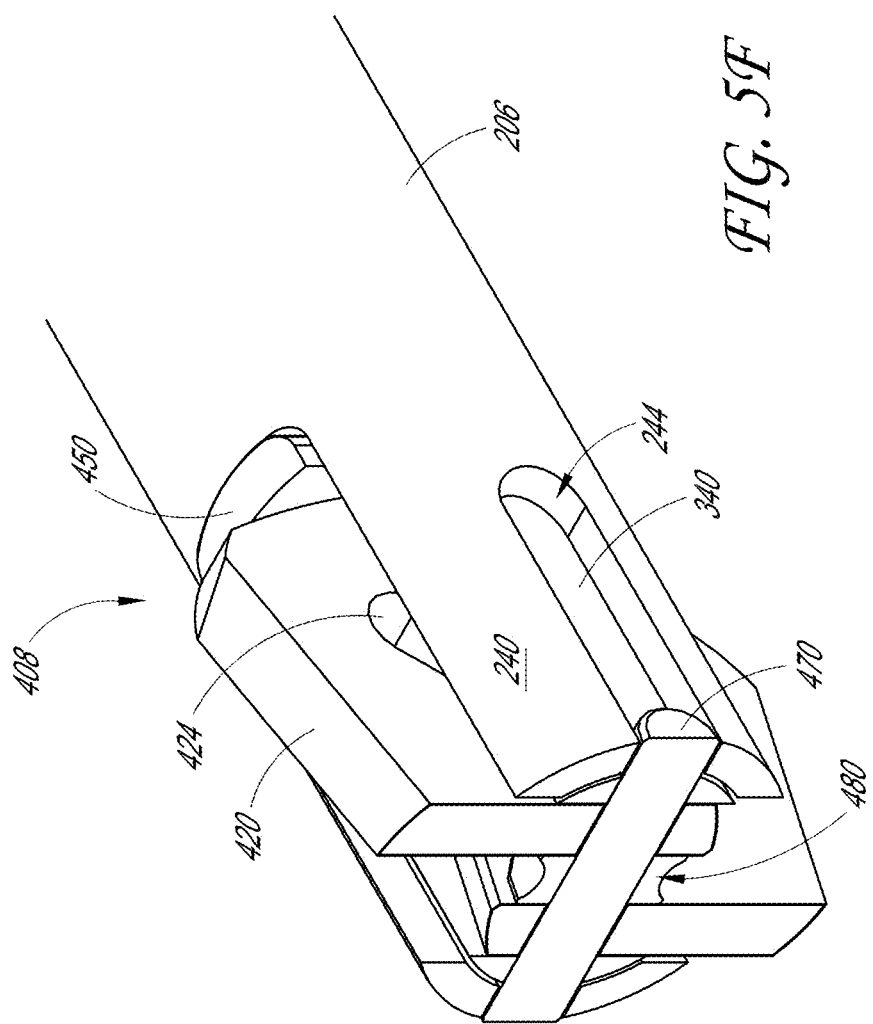

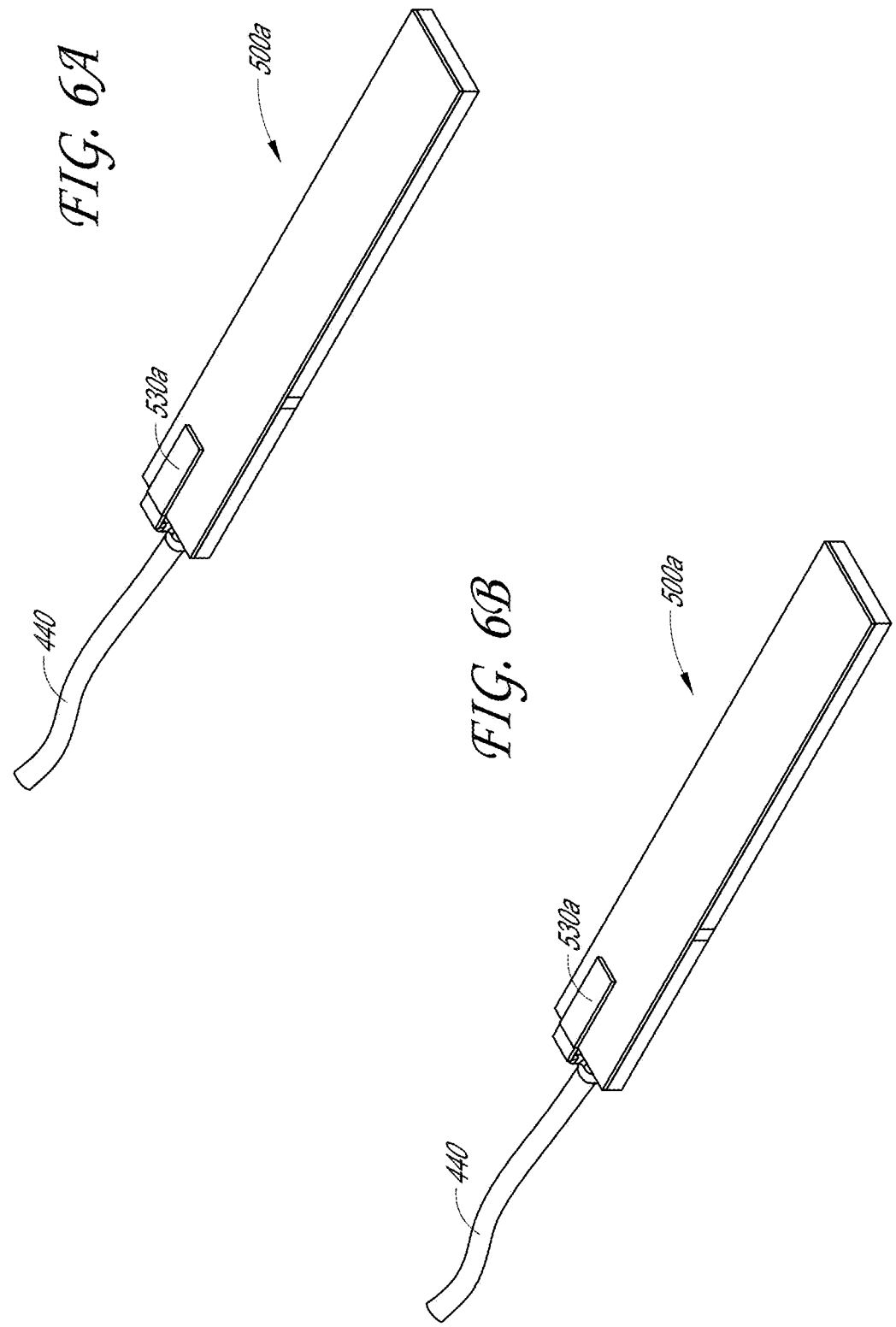

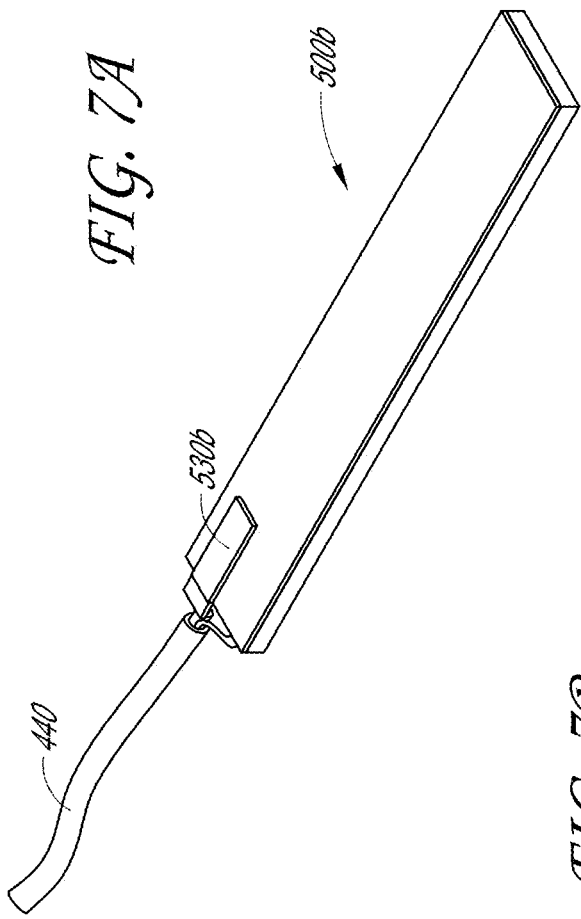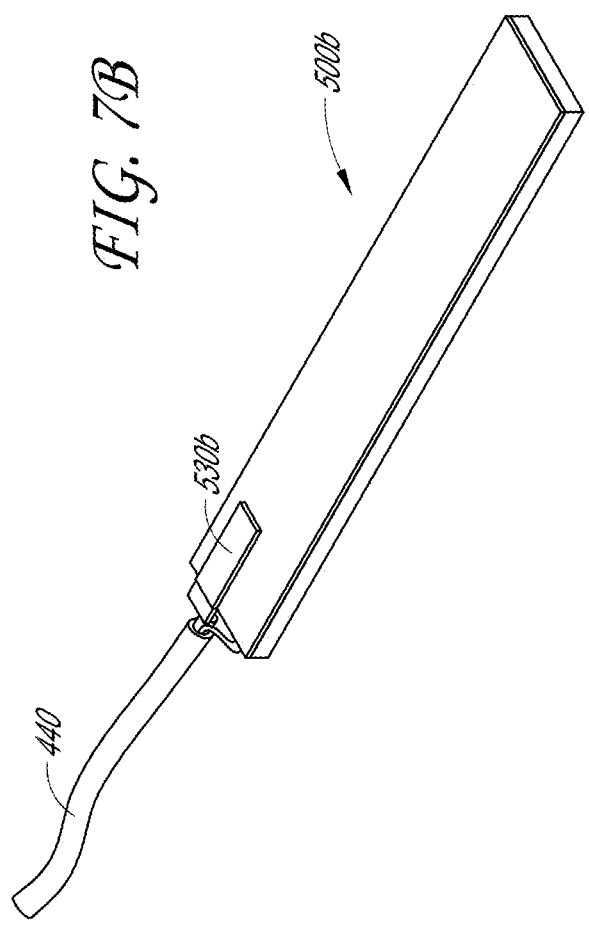

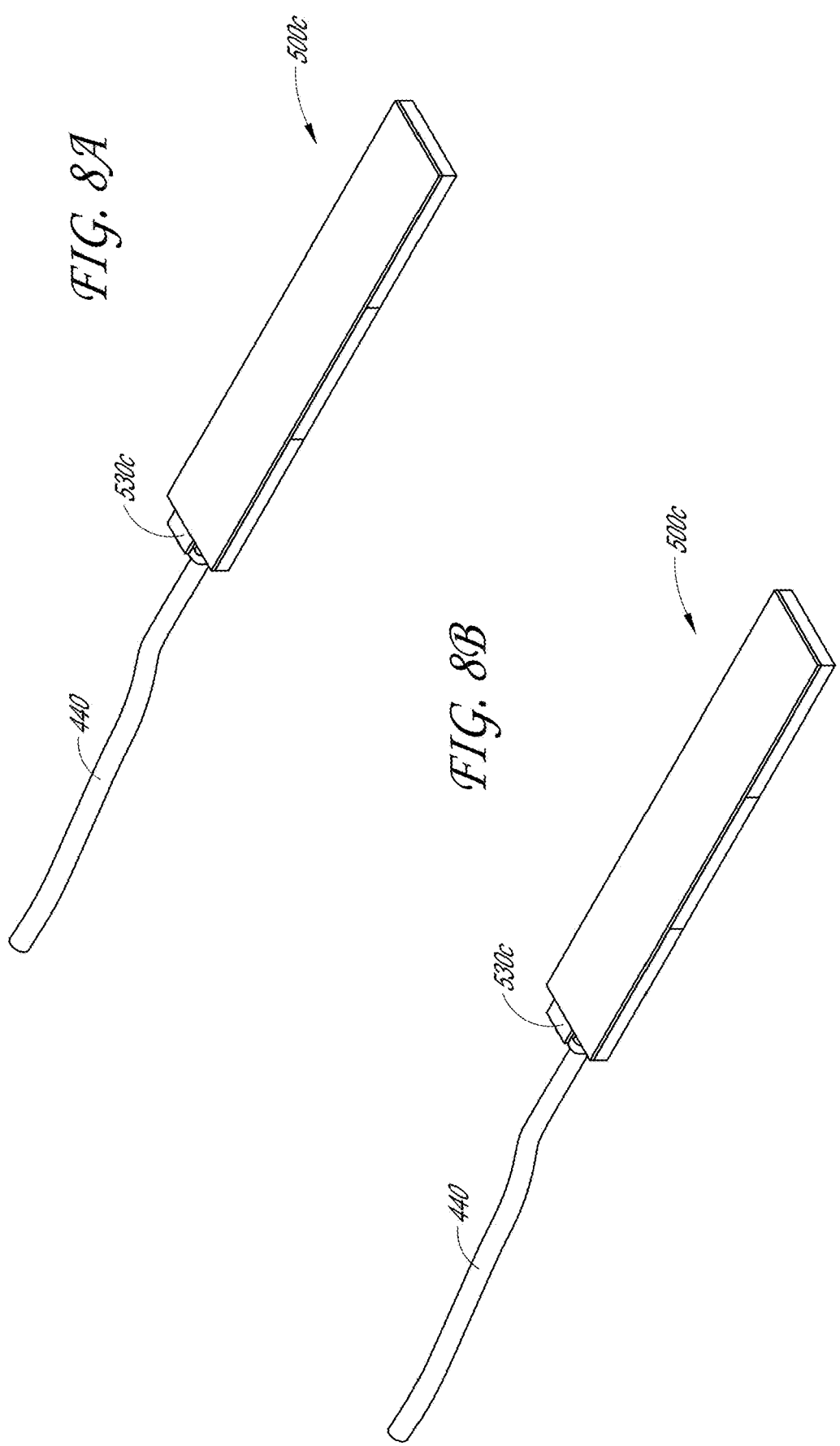

TISSUE ENGAGEMENT APPARATUS FOR THEAPEUTIC ULTRASOUND APPARATUS AND METHOD

PRIORITY STATEMENT

This application claims a priority benefit under 35 U.S.C. § 119 of U.S. Patent Application No. 62/560,069, filed Sep. 18, 2017, the entirety of which is hereby incorporated by reference herein.

BACKGROUND

This disclosure relates to methods and apparatus for surgical procedures that utilize therapeutic ultrasound. Therapeutic ultrasound refers to the use of ultrasonic waves to induce changes in tissue state through both thermal effects (e.g., induced hyperthermia) and mechanical effects (e.g., induced cavitation). Therapeutic ultrasound can refer to either High Intensity Focused Ultrasound (HIFU) or Direct Therapeutic Ultrasound (DTU) and can be employed in both hyper-thermic and cavitational medical applications, whereas low intensity ultrasound has been used principally for its cavitation effect. Diagnostic medical ultrasonic imaging is well known, for example, in the common use of sonograms for fetal examination.

BRIEF DESCRIPTION OF THE FIGURES

Various embodiments are depicted in the accompanying drawings for illustrative purposes, and should not be interpreted as limiting the scope of the embodiments. Furthermore, various features of different disclosed embodiments can be combined to form additional embodiments, which are part of this disclosure.

FIG. 1A illustrates an exploded view of a sample therapeutic ultrasound device.

FIG. 1B illustrates a cross-sectional side view of the sample therapeutic ultrasound device of FIG. 1A.

FIGS. 2E-2H illustrate a plurality of views of an adaptor of the outer tube assembly of the sample therapeutic ultrasound device of FIG. 1A.

FIGS. 3B and 3C illustrate a plurality of views of the inner tube assembly of the sample therapeutic ultrasound device of FIG. 1A.

FIGS. 4A-4F illustrate various views of a tissue engagement assembly located on a distal end of the sample therapeutic ultrasound device of FIG. 1A.

FIG. 5B illustrates a prospective view of the tissue engagement assembly located at the distal end of the sample therapeutic ultrasound device of FIG. 1A.

FIG. 5E illustrates a cross-sectional view of the distal end of the sample therapeutic ultrasound device of FIG. 1A located along plane "5E-5E" as shown in FIG. 5B.

FIG. 5F illustrates a cross-sectional view of the distal end of the sample therapeutic ultrasound device of FIG. 1A located along plane "5F-5F" as shown in FIG. 5B.

FIGS. 6A-6B illustrate a first embodiment of an acoustic stack located in the tissue engagement assembly of the sample therapeutic ultrasound device of FIG. 1A.

FIGS. 7A-7B illustrate a second embodiment of the acoustic stack located in the tissue engagement assembly of the sample therapeutic ultrasound device of FIG. 1A.

FIGS. 8A-8B illustrate a third embodiment of the acoustic stack located in the tissue engagement assembly of the sample therapeutic ultrasound device of FIG. 1A.

DETAILED DESCRIPTION

Figure 1C:
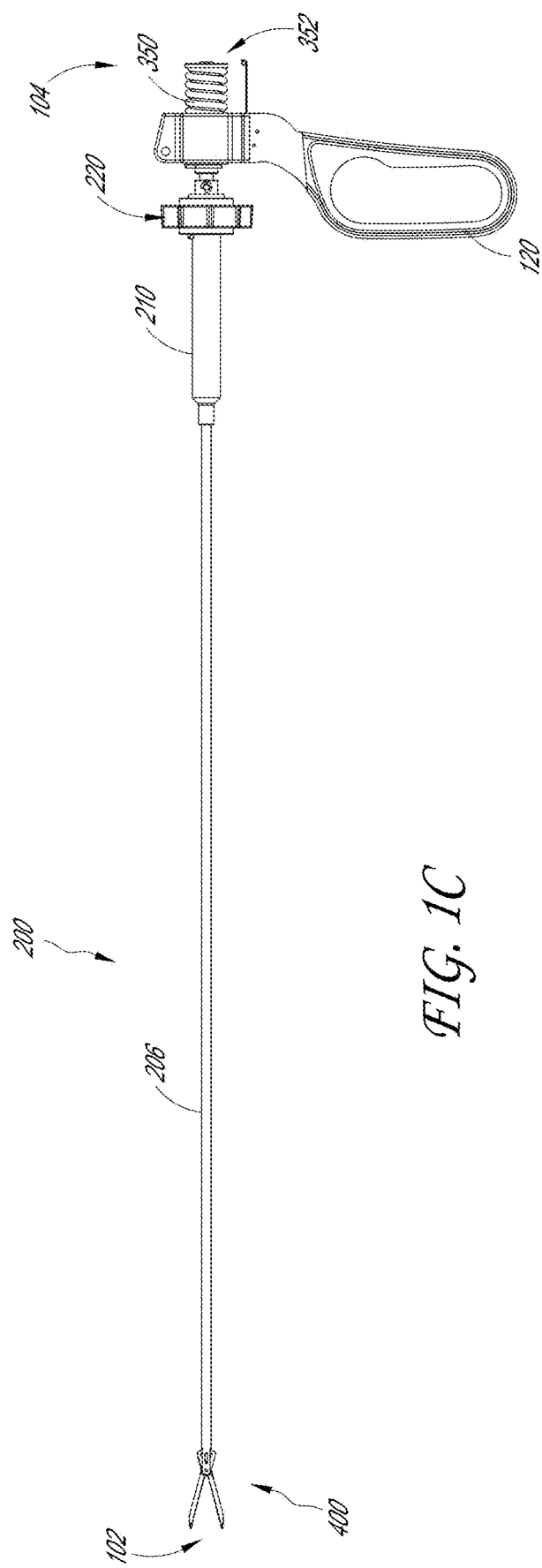
FIG. 1C illustrates a side view of internal elements of the sample therapeutic ultrasound device of FIG. 1A wherein the external housing is removed.

Various therapeutic ultrasound apparatus and methods are disclosed that may be employed to achieve one or more desired improvements in the field of surgery. For purposes of presentation, certain embodiments are disclosed with respect to a surgical therapeutic ultrasound apparatus and methods of use, but the disclosed embodiments can be used in other contexts as well. Indeed, the described embodiments are examples only and are not intended to restrict the general disclosure presented and the various aspects and features of this disclosure. The general principles described herein may be applied to embodiments and applications other than those discussed herein without departing from the spirit and scope of the disclosure. This disclosure should be accorded the widest scope consistent with the principles and features that are disclosed or suggested herein.

Although certain aspects, advantages, and features are described herein, it is not necessary that any particular embodiment include or achieve any or all of those aspects, advantages, and features. For example, some embodiments may not achieve the advantages described herein, but may achieve other advantages instead. No feature, component, or step is necessary or critical.

Overview

In the U.S. alone, several hundred thousand surgical procedures are performed each year that involve the removal of tissue, or a portion of an organ because of some pathology involving the tissue. Many of these procedures remove benign or malignant tumors. Although a significant percentage of such tissue and organ removal procedures employ conventional surgical techniques, a major effort has been directed to replacing conventional surgical techniques with minimally invasive surgical techniques to reduce morbidity. However, performing such surgery using minimally invasive instruments requires significant training and advanced skills on the part of the operating physician. Disclosed below are methods and apparatus that are minimally invasive and are easier to implement than those currently used.

During invasive surgery, an obvious problem is bleeding. In a retrospective cohort study involving 600 hospitals, bleeding complications occurred in approximately 45% of surgical procedures, increasing hospitalization by about 125% (7 days on average), and increasing hospital costs by ~$7,500 per patient (per procedure). Bleeding also significantly contributes to the majority of the approximately 120,000 trauma deaths per year. In trauma, 30% to 40% of deaths are related to uncontrolled bleeding. Blood transfusions (planned or unexpected) and reoperations are used to mitigate bleeding and avert death. These procedures can be costly and are associated with complications. Blood transfusion can lead to nosocomial infection, immunosuppression, transfusion-related acute lung injury, and even death. Reoperations lead to increased costs and longer hospitalization. As a result, many needless bleeding complications occur with current technologies resulting in increased hospitalization times, hospital costs, and patient deaths. To reduce bleeding, surgical techniques are needed to provide for fast and robust control of bleeding—allowing surgical procedures without hemorrhaging as well as rapidly controlling bleeding in trauma.

The most common surgical technique in the state of the art for coagulating bleeding vessels is to apply an electrical cauterizing probe to the bleeding site. However, if a bleeding vessel is more than about 1.5 millimeters (mm) in diameter, or an organ which is highly vascularized and where uncontrolled hemorrhage is the primary cause of death, direct electrical cauterization is ineffective. In such instances, a more complicated technique of clamping of a large blood vessel and electrical cauterization via the clamp or with laser light can instead be used. However, problem frequently faced, that is not solved with either electrical or laser cauterization techniques, is the control of a rapidly bleeding vessel because the blood egress is often sufficiently large enough to carry the heat away before coagulation or tissue necrosis is accomplished. Particularly in surgery involving organs, neither electrical or laser cauterization is effective. Moreover, organs such as the liver and the spleen are subject to bleeding profusely from cracks in the parenchyma, which is usually diffuse and non-pulsatile due to the large number of small vessels.

The disclosed methods and apparatus can be used to assist emergency, specialty, and general physicians in performing surgeries rapidly and without common complications associated with bleeding. This can reduce surgical and anesthesia time and minimizes blood product usage, which can improve patient outcomes and decrease healthcare costs.

Therapeutic Ultrasound Overview

In view of the surgical procedures described above, disclosed are methods and apparatus for enabling surgical procedures relating to bloodless surgery and for stemming hemorrhaging. For example, therapeutic ultrasound can be used to form cauterized tissue regions prior to surgical incision. This can be particularly effective for use in surgical lesion removal or resecting highly vascularized tissue.

Generally, therapeutic ultrasound is a modality in interventional medicine that is based on the delivery of acoustic energy at ultrasonic frequencies within the human body with the precise intent of eliciting well defined biological effects. These biological consequences are induced, or mediated, primarily by two mechanisms of action: thermal effects and mechanical effects. Thermal effects derive from the absorption of the vibrational acoustic energy by the tissue (through relaxation and thermos-viscous processes) and its conversion into heat which, in turn, generates a temperature increase in the exposed region. Mechanical effects are due to the large gradients in pressure associated with the oscillatory nature of the ultrasound waves which produce high stress and strain forces as experienced by the medium. Additionally, in the presence of gas bodies within the ultrasonic field of action, cavitation may also occur. Cavitation is the dynamic activity of gas bubbles which grow and collapse under the influence of an acoustic field. It can be stable and sustained, when the bubbles oscillate in phase with the acoustic wave without being destroyed, in which case they produce significant shearing forces and additional viscous heating; or it can be inertial and transient, when new gas bubbles are nucleated from dissolved gas in the tissue and they rapidly grow and violently collapse before dissolving again, in which case they produce extremely high mechanical stresses, shock waves, and strong fluid microjets.

One type of therapeutic ultrasound is High Intensity Therapeutic Ultrasound (also commonly referred to as HIFU-High Intensity Focused Ultrasound and FUS-Focused Ultrasound Surgery). HIFU is mainly directed towards the very rapid heating of tissue above the protein denaturization and cell coagulative necrosis thresholds and is intended to create a permanent, irreversible, and localized thermal lesion within the tissue or to cauterize a bleeding vessel. This results in the concentration of the majority of the available input power in a focal volume of the order of 1-2 wavelengths in cross section and about 5-7 wavelengths in length (approximately 1.5×1.5×10 mm3 for a 1 MHz system) with extremely high energy densities in the order of hundreds to thousands of Watts/cm². This high-energy concentration allows for rapid temperature rise in the focal volume such that cell necrosis and ablation is achieved within 1-2 seconds. Although energy densities at the face of the ultrasound applicator are orders of magnitude lower than at the focus, because of the multiple unit lesions necessary for a full treatment, the ultrasound energy deposition at the skin interface and immediately below compounds during the whole application and typically unwanted skin burns and subcutaneous damage occur.

HIFU can be employed in both hyperthermic and cavitational medical applications. HIFU waves, for example, can be propagated into tissue toward a discrete focal region, and the accumulation of the resultant harmonic frequencies can induce rapid heating at the focal region that ablates, necrotizes, and/or otherwise damages the tissue. In a clinical setting, HIFU-induced heating can be used to treat benign and malignant tumors (e.g., in the brain, uterus, prostate, liver, etc.) and/or occlude blood vessels (e.g., to induce hemostasis of internal bleeds, intervene in fetal blood sharing anomalies, and confine tumor blood supply). During HIFU therapy and/or other treatments that form heat-induced lesions, image guidance and treatment monitoring (e.g., temperature monitoring) can be used for controlling and optimizing the parameters of the treatment and assessing its efficacy.

In HIFU hyperthermia treatments, the intensity of ultrasonic waves generated by a highly focused transducer increases from the source to the region of focus where it can reach a very high temperature, (e.g., 98° Centigrade). The absorption of the ultrasonic energy at the focus can induce a sudden temperature rise of tissue which can be as high as between 100-200° K/sec. Such a dramatic increase in temperature can cause the ablation of target cells at the focal region. The focal region dimensions are referred to as the depth of field, and the distance from the transducer to the center point of the focal region is referred to as the "depth of focus."

Thus, HIFU hyperthermia treatments can result in necrotization of an internal lesion without damage to the intermediate tissues. The disclosed methods and apparatus using HIFU are a non-invasive surgical technique because the ultrasonic waves provide a non-effective penetration of intervening tissues, yet with sufficiently low attenuation configured to deliver energy to a small focal target volume. For example, a very high frequency, e.g., 30 MHz wave would be absorbed nearly immediately by the first tissue it is applied to. Yet, lower frequencies, e.g., 30 KHz-60 KHz, are associated with cavitation effects because of the longer rarefaction time periods, allowing gaseous vapor formation. Thus, the effect of ultrasound energy is quite different at a frequency of 30 KHz versus 30 MHz. Moreover, the rate of heat generation in tissue is proportional to the absorption constant. For example, for the liver, the attenuation constant is approximately 0.0015 at 30 KHz, but is approximately 0.29 at 3 MHz. Therefore, all other variables being equal, the heat generated in liver tissue is about 190 times greater at 3 MHz than at 30 KHz. While this means hyperthermia can be achieved more quickly and to a much greater level with high frequencies, the danger to intervening tissue between the transducer and the focal region is much more prevalent. Therefore, by instead using a lower frequency, energy can be delivered to a small focused target volume of tissue without damaging intervening tissues.

Direct Therapeutic Ultrasound (DTU), another type of therapeutic ultrasound, refers to the use of direct therapeutic ultrasonic waves to induce changes in tissue state through both thermal effects (e.g., induced hyperthermia) and mechanical effects (e.g., induced cavitation). DTU can be used to directly lock and compress vascularized tissue, up to several millimeters thick, before being coagulated and sealed by the ultrasound energy in seconds. While still based on ultrasonically mediated thermal mechanisms, in contrast to traditional high intensity therapeutic ultrasound, this approach utilized significantly lower power densities (in the order of 5-30 W/cm²) and a uniform distribution of the ultrasound energy throughout the full treatment domain, thus avoiding generation of localized hot spots and collateral damage. In fact, the treatment region is fully contained and well-defined within the opposite jaws of the device where a uniform planar standing wave is generated between the two opposing ultrasound transducers, quickly dissipating away from the applicators edges resulting in minimal thermal spreading.

This type of application is intended for open and minimally-invasive laparoscopic surgery, and compared to standard HIFU applications does not require additional targeting and monitoring systems and does not suffer from similar safety concerns in terms of on-path unintended injury and/or cavitation effects. This is due to the fact that the propagation path is only few millimeters long and fully restricted within the applicator footprint thus avoiding significant energy diffraction; peak rarefactional pressure are well below the in-vivo threshold for cavitation processes; and the tissue is subject to significant overpressure from the clamping device, additionally inhibiting the inception of bubble formation and cavitation.

Disclosed is also an apparatus configured to emit therapeutic ultrasound (whether HIFU or DTU) from one or more transducers that are attached to a minimally invasive surgical instrument. Such a tool can provide sufficient clamping or engagement pressure to collapse blood vessels' walls, so that they will be sealed by the application of the DTU, and by the resulting thermal ablation and tissue cauterization. Such an instrument can provide feedback to the user that the lesion is completely transmural and that blood flow to the region distal of the line of thermal ablation has ceased. In some embodiments, instruments having opposed arms can be configured for use in conventional surgical applications. Instruments can be implemented with transducers on only one arm, and an ultrasound reflective material disposed on the other arm.

The disclosure provided herein describes apparatus and methods related to performing surgical procedures with a minimum of bleeding. In some embodiments, such procedures are minimally invasive procedures (e.g., laparoscopy, endoscopy, etc.). In other embodiments the disclosed procedures and apparatus can also be applied to more invasive surgical procedures. The disclosed apparatus and methods can enable removal of undesirable tissues, such as benign and malignant tumors, from the body without fear of uncontrolled bleeding that can result from such procedures using conventional techniques.

In particular, disclosed is an apparatus for sealing or cutting tissue having a small engagement region such that the apparatus can be used in minimally invasive procedures. As will be discussed in detail, although the apparatus comprises a small engagement region, the device is configured to provide sufficient clamping force and power to the target site to effectively cauterize tissue in a short amount of time.

Therapeutic Ultrasound Device

FIGS. 1A-1D illustrate a plurality of views of a sample therapeutic ultrasound device 100 formed in accordance with the present disclosure. FIG. 1A illustrates an exploded view of the proximal end 104 of the therapeutic ultrasound device 100 such that the interior components of the therapeutic ultrasound device 100 are visible. FIG. 1B illustrates a cross-sectional view of the therapeutic ultrasound device 100 showing the arrangement of the internal components of the therapeutic ultrasound device 100 within the housing 110.

The disclosed therapeutic ultrasound device 100 is configured to use focused ultrasound transducers or unfocused ultrasound transducers integrated with a hemostatic clamping instrument. When deployed, the ultrasound energy ablates the tissue contained between the heads, thereby forming a hemostatic plane of cauterization. This allows surgeons to remove tumors, tissue, or organs without bleeding and also provides a method to rapidly control bleeding in trauma situations, significantly reducing the risk of bleeding complications and reducing trauma death due to exsanguination. This technology is applicable to open and laparoscopic procedures. As will be discussed in more detail below, the disclosed therapeutic ultrasound device 100 can cauterize tissues over 3 cm thick and can assess whether treatment has been completed effectively.

As an overview, the therapeutic ultrasound device 100 may include a distal end 102 and a proximal end 104, wherein the distal end 102 includes an engagement portion and the proximal end 104 includes a user actuation mechanism. For example, the proximal end 104 of the therapeutic ultrasound device 100 includes a housing 110 that secures the internal components of the therapeutic ultrasound device 100. The housing 110 can include a first half (e.g., left housing 110a) and a second half (e.g., right housing 110b) that can be secured together using a plurality of first fasteners 114 and second fasteners 116. As shown in FIG. 1A, the plurality of first fasteners 114 and second fasteners 116 are inserted through the plurality of openings 112 through both halves of the housing 110. In some examples, the first fasteners 114 are screws and the second fasteners 116 are inserts that are configured to engage with each other and secure both halves of the housing 110, however, those skilled in the art will recognize that other types of fasteners may be used without departing from the scope of the present disclosure. The first fasteners 114 and the second fasteners 116 can comprise any structures that secure the housing 110 to the therapeutic ultrasound device 100.

As shown in FIG. 1A, the housing 110 can be configured to secure the handle 120 along with a plurality of other components that are configured to actuate the therapeutic ultrasound device 100.

The therapeutic ultrasound device 100 can include a latch guide 130. As shown in FIG. 1A, the latch guide 130 can comprise a first portion 130a and second portion 130b that are configured to provide a path for the spring latch to travel. This can allow the lever to be "latched" in a closed position. This can ensure that the tissue is compressed and held during treatment. In some examples, the two halves of the latch guide 130 are configured to provide a symmetrical path, thereby distributing the forces on the latch evenly when the latch is latched.

In some embodiments, the therapeutic ultrasound device 100 includes a connector 140 and cable 150 that are configured to provide power to the therapeutic ultrasound device 100. As will be discussed in more detail, the connector 140 and the cable 150 are configured to provide power to the plurality of transducers located in the tissue engagement assembly 400 through a plurality of wires and/or cables. The tissue engagement assembly 300 may also be referred to herein as a "jaw" assembly or "clamping" assembly FIGS. 1A and 1B also illustrate a handle 120 located at the proximal end 104 of the therapeutic ultrasound device 100. As shown in FIG. 1B, the handle 120 may extend out from the housing 110 to allow the user to grip the handle 120 with his/her fingers. In some embodiments, the handle 120, along with the housing 110, provides a comfortable and ergonomic fit for the hand of the user. For example, the palm of the user can rest on the exterior of the proximal end of the housing 110 and the thumb of the user can curl about the width of the base of the housing 110. The remaining fingers of the user can be configured to fit in the opening of the handle 120 such that the user can pull back and release the handle 120.

The handle 120 can be configured to actuate the movement of a jaw assembly 400 located on the distal end 102 of the therapeutic ultrasound device 100. FIG. 1C illustrates the therapeutic ultrasound device 100 with the proximal end 104 of the therapeutic ultrasound device 100 with the housing 110 removed. As shown, the proximal end 104 of the therapeutic ultrasound device 100 can include a spring 350 disposed about the spring guide 352 adjacent to the handle 120. In some examples, the spring 350 and the spring guide 352 allow for the handle 120 to retract and return to its original position. In some embodiments, the spring 350 and the spring guide 352 are configured to allow the user to latch the handle 120 such that the jaw assembly 400 remains clamped on the tissue. Subsequent squeezing of the handle 120 can be unlatch the handle to allow the spring to follow the spring guide 352 while the handle 120 returns to a first position wherein the jaw assembly 400 is opened. In some embodiments, the handle 120 can be configured to include a memory chip (not illustrated). The memory chip can be configured to store operating parameters for the therapeutic ultrasound device 100.

As will be discussed in more detail below, engagement of the handle 120 can be configured to move the inner tube assembly 300 (shown in FIG. 1D) relative to the outer tube assembly 200. In some embodiments, the handle 120 is adjacent to the rotation mechanism 220 which is configured to allow the jaw assembly 400 to be rotated about the longitudinal axis. In some embodiments, the rotation mechanism 220 can allow rotation through ±175 degrees about the longitudinal axis.

Figure 1D:
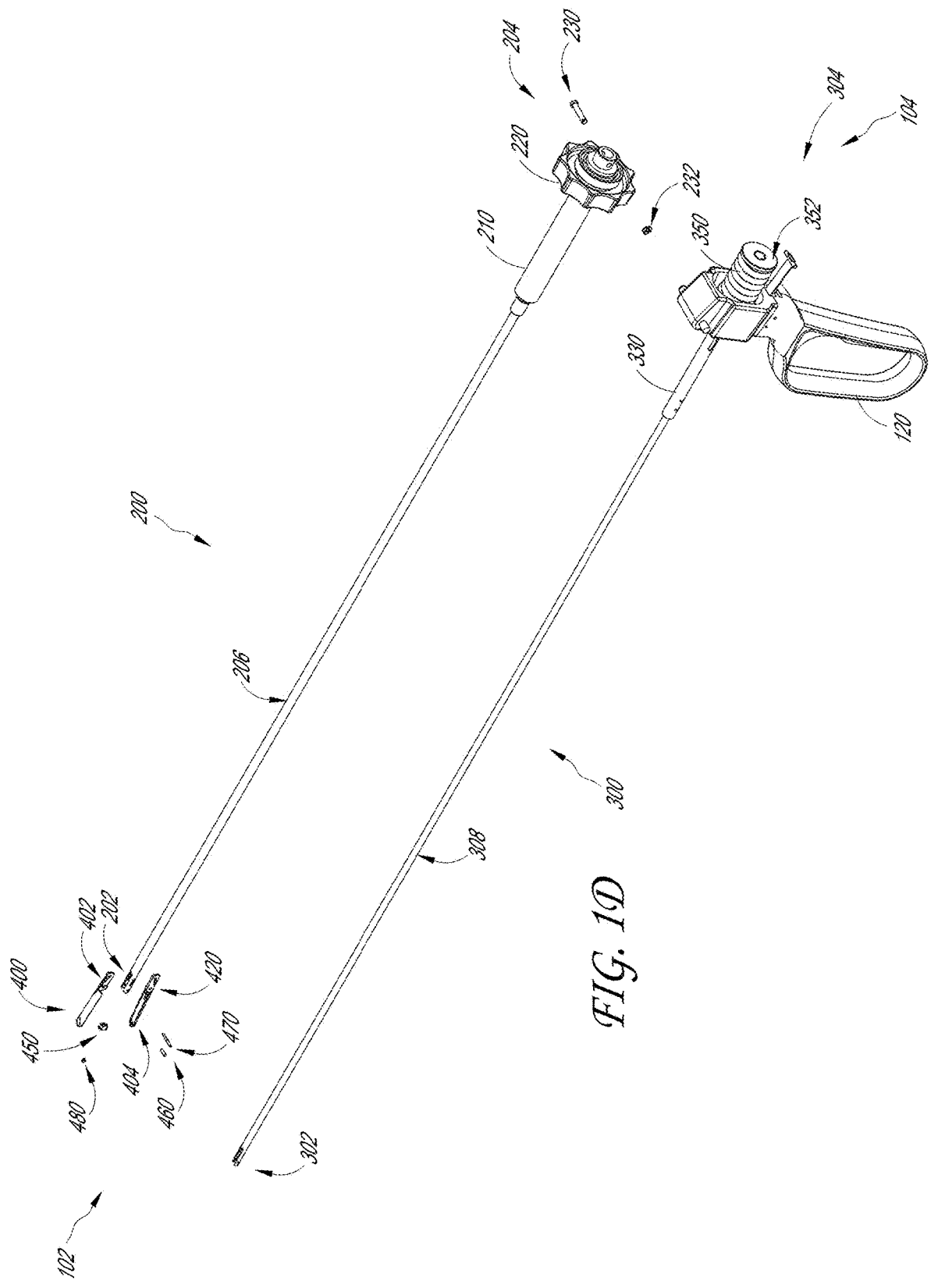
FIG. 1D illustrates an exploded view of the internal elements shown in FIG. 1C, namely, an outer tube assembly and an inner tube assembly, of the sample therapeutic ultrasound device of FIG. 1A.

FIG. 1D illustrates an exploded view of the therapeutic ultrasound device 100 with the housing 110 removed. As will be discussed in turn below, the therapeutic ultrasound device 100 can include an outer tube assembly 200, an inner tube assembly 300, and a jaw assembly 400.

As a brief overview, the outer tube assembly 200 can be disposed over the inner tube assembly 300. The outer tube assembly 200 can include an outer tube 206 and an adaptor 210 located at a proximal end 204. In some embodiments, the adaptor 210 is configured to be attached to the rotation mechanism 220. The adaptor 210 can be configured to enable the therapeutic ultrasound device 100 to accommodate an outer tube 206 and/or an inner tube 308 having varying diameters without needing to redesign the size and configuration of the attached handle assembly and other internal mechanisms of the therapeutic ultrasound device 100.

The inner tube assembly 300 can include an inner tube 308 and a connector 330 located at a proximal end 304. As shown in FIG. 1D, the connector 330 can be attached to the handle assembly. As will be discussed in more detail below, the outer tube 206 and the adaptor 210 are disposed over the inner tube 308 and the connector 330 respectively. The outer tube assembly 200 can be secured to the inner tube assembly 300 using a plurality of fasteners. In some embodiments, the plurality of fasteners comprise a retaining pin 230 and a retaining ring 232; however, as noted above the fasteners can comprise any shape or structure without departing from the scope of the present disclosure.

As shown in FIG. 1D, the jaw assembly 400 can be located at the distal end 102 of the therapeutic ultrasound device 100. As will be discussed in more detail below, the jaw assembly 400 can include a top jaw 402 and a bottom jaw 404. The top jaw 402 and the bottom jaw 404 can be secured to the distal end 202 of the outer tube 206 and the distal end 302 of the inner tube 308 using a pivot pin 460 and an inner tube pin 470. In some embodiments, the jaw assembly 400 can include a bushing 480 to secure the pivot pin 460 in place and to maintain the space between ears 420 of the top jaw 402 and the bottom jaw 404. In some examples, the bushing 480 can be configured to prevent rotation of the top jaw 402 and the bottom jaw 404 within the jaw assembly 400.

The jaw assembly 400 can be secured to the outer tube 206 and the inner tube 308 such that withdrawal or advancing of the inner tube 308 relative to the outer tube 206 will cause the top jaw 402 and the bottom jaw 404 of the jaw assembly 400 to open and close. As noted above, and as will be discussed in more detail below, the engagement of the handle 120 in a first direction will case movement of the inner tube 308, relative to the outer tube 206, in the first direction. This can cause the jaw assembly 400 to open. Similarly, release of the handle 120 in a second direction can cause movement of the inner tube 308, relative to the outer tube 206, in the second direction. This can cause the jaw assembly 400 to close.

Outer Tube Assembly

Figure 2A:
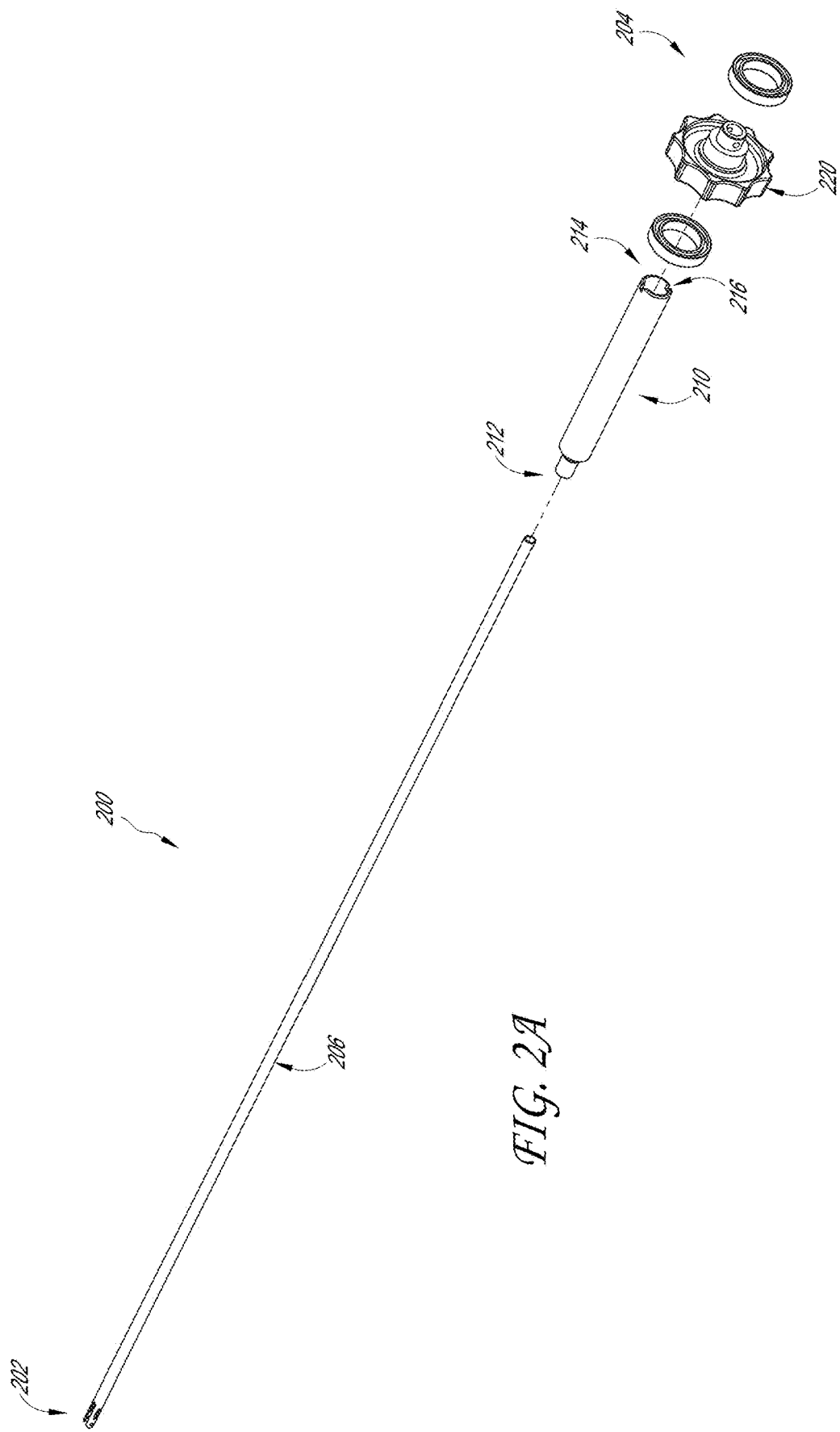
FIG. 2A illustrates an exploded view of the outer tube assembly of the sample therapeutic ultrasound device of FIG. 1A.
Figure 2B:
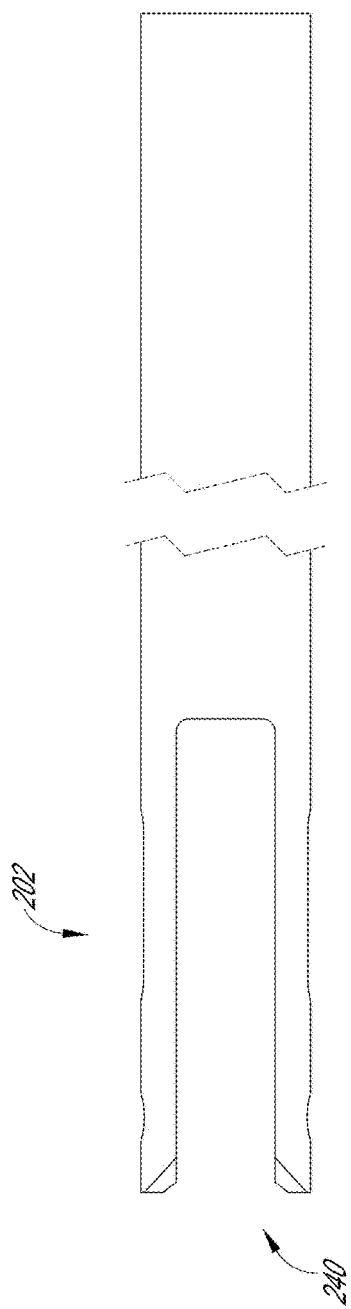
FIGS. 2B-2C illustrate a plurality of views of a distal end of the outer tube assembly of the sample therapeutic ultrasound device of FIG. 1A.
Figure 2C:
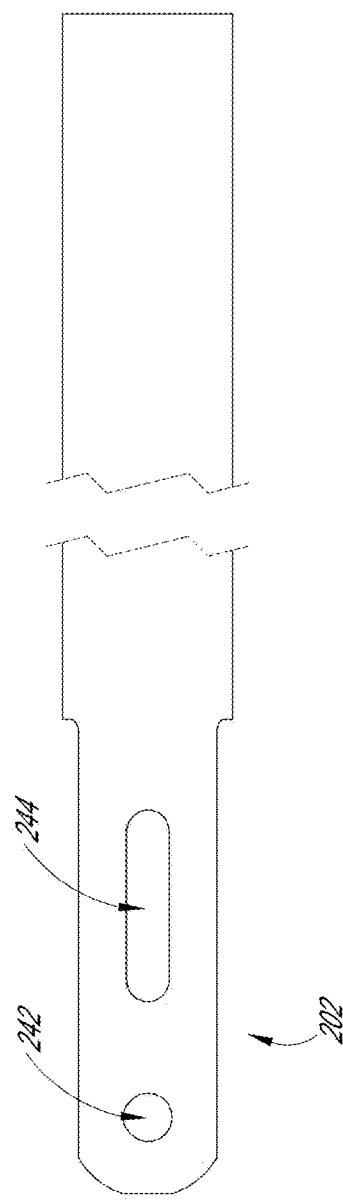
Figure 2D:
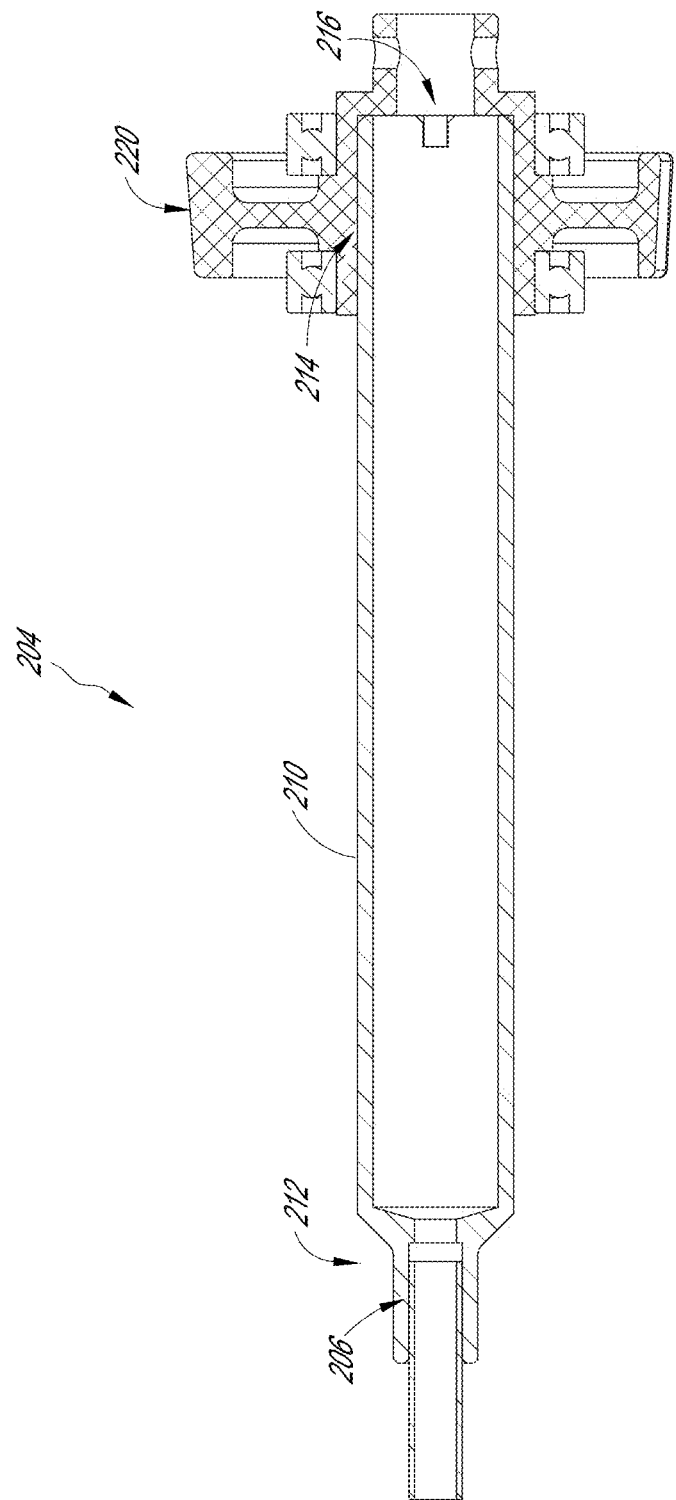
FIG. 2D illustrates a cross-sectional view of a proximal end of the outer tube assembly of the sample therapeutic ultrasound device of FIG. 1A.

FIGS. 2A-2G illustrate various embodiments of the outer tube assembly 200. FIG. 2A illustrates an exploded view of certain components of the outer tube assembly 200; FIGS. 2B-2C illustrate the distal end 202 of the outer tube 206; FIG. 2D illustrates the proximal end 204 of the outer tube assembly 200; and FIGS. 2E-2H illustrate a plurality of views of the adaptor 210.

As discussed above, the outer tube assembly 200 can include the outer tube 206, the adaptor 210, and the rotation mechanism 220. As shown in FIG. 2A, a proximal end of the outer tube 206 can be secured to the adaptor distal end 212 and the adaptor proximal end 214 can be attached to the rotation mechanism 220. In some embodiments, the rotation mechanism 220 can comprise any material such as plastic, metal, rubber, etc.

As will be discussed in more detail below, the jaw assembly 400 can have a width ranging from 3 mm to 10 mm. In some embodiments, the jaw assembly 400 can have a width ranging up to 15 mm. The jaw assembly 400 should therefore be configured to apply sufficient clamping or engagement force to the target tissue in order to generate sufficient force for treatment. In some embodiments, this can be 10-14 lbs. of clamping force at the jaw assembly 400. In some embodiments, the clamping force at the jaw assembly 400 can be less than 10 lbs., between 10-11 lbs., between 11 lbs.-12 lbs., between 12 lbs.-13 lbs., between 13 lbs.-14 lbs., or greater than 14 lbs. In some embodiments, the clamping force at the jaw assembly 400 can be any of 10 lbs., 11 lbs., 12 lbs., 13 lbs., or 14 lbs. To translate the force required for the device, the outer tube 206 can comprise a material that is configured to withstand these forces. For example, the outer tube 206 can comprise double hard stainless steel tubing, aluminum, titanium, plastic, carbon fiber, etc. In some examples, the adaptor 210 can comprise a material that is configured to withstand these forces. For example, the adaptor 210 can comprise double hard stainless steel tubing, aluminum, titanium, plastic, carbon fiber, etc. The outer tube 206 and the adaptor 210 will be discussed in turn.

FIGS. 2B-2C illustrate the distal end 202 of the outer tube 206. The distal end 202 of the outer tube 206 can include a yoke 240 that includes a pair of arms. Each of the pair of arms of the yoke 240 can include an opening 242 and a slot 244. As shown in FIG. 1D, a pivot pin 460 can be configured to fit through the opening 242 and the inner tube pin 470 can be configured to move along the slot 244. As will be discussed in more detail below, movement of the inner tube pin 470 along the slot 244 can be configured to open and close the jaw assembly 400.

FIG. 2D illustrates the proximal end 204 of the outer tube assembly 200. The proximal end 204 of the outer tube assembly 200 can include the adaptor 210 having a distal end 212 and a proximal end 214. In some embodiments, the distal end 212 of the adaptor 210 is disposed over the proximal end of the outer tube 206. In some examples, the proximal end 214 of the adaptor 210 is located within the rotation mechanism 220. FIGS. 2E-2H illustrates a plurality of views of the adaptor 210. A proximal end 214 of the adaptor 210 can include a plurality of proximal grooves 216. In some examples, the proximal grooves 216 are configured to lock into a rotation knob. This can allow the user to rotate the tip of the therapeutic ultrasound device 100 (e.g., the jaw assembly 400).

Inner Tube Assembly

Figure 3A:
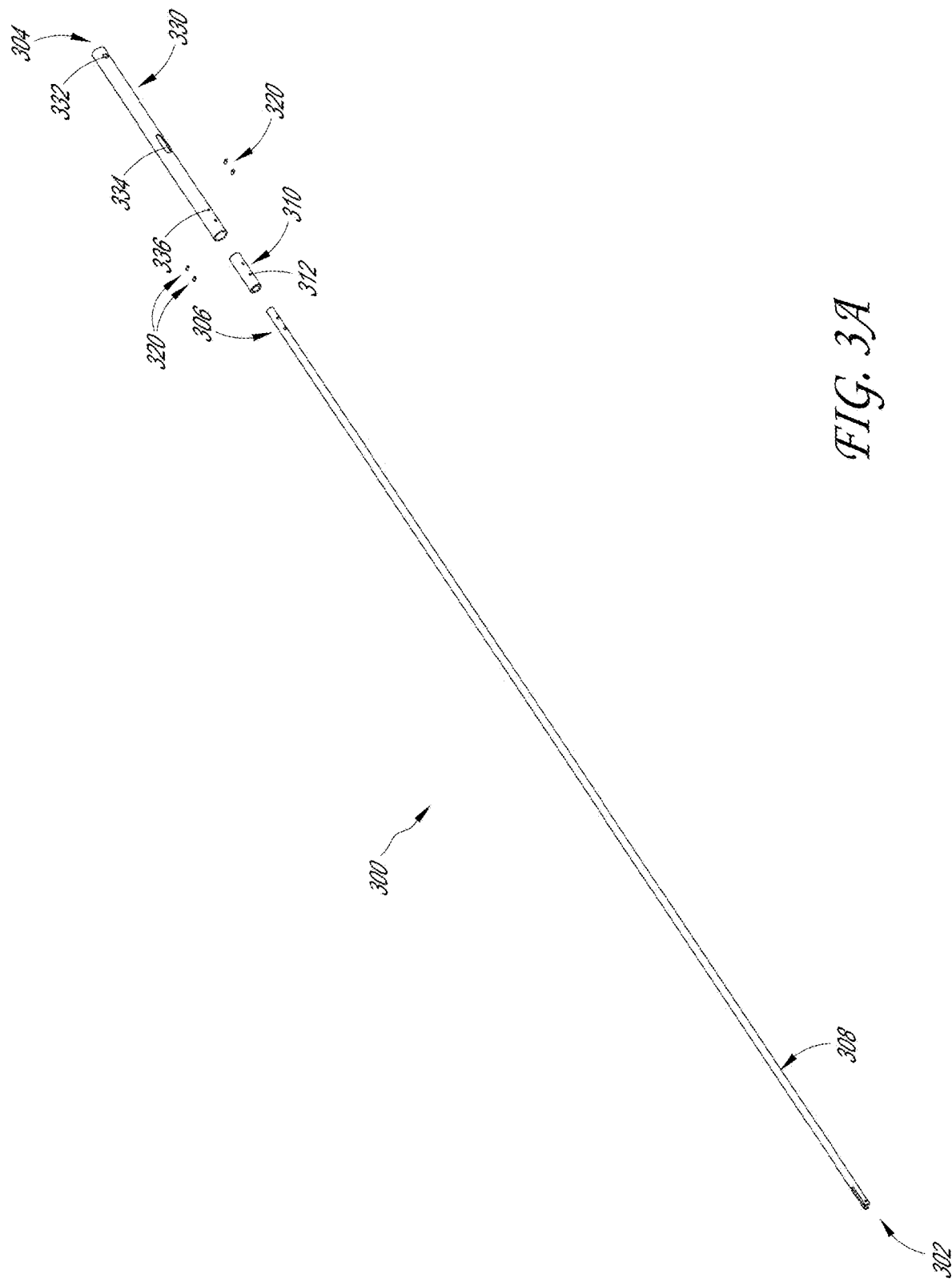
FIG. 3A illustrates an exploded view of the inner tube assembly of the sample therapeutic ultrasound device of FIG. 1A.
Figure 3D:
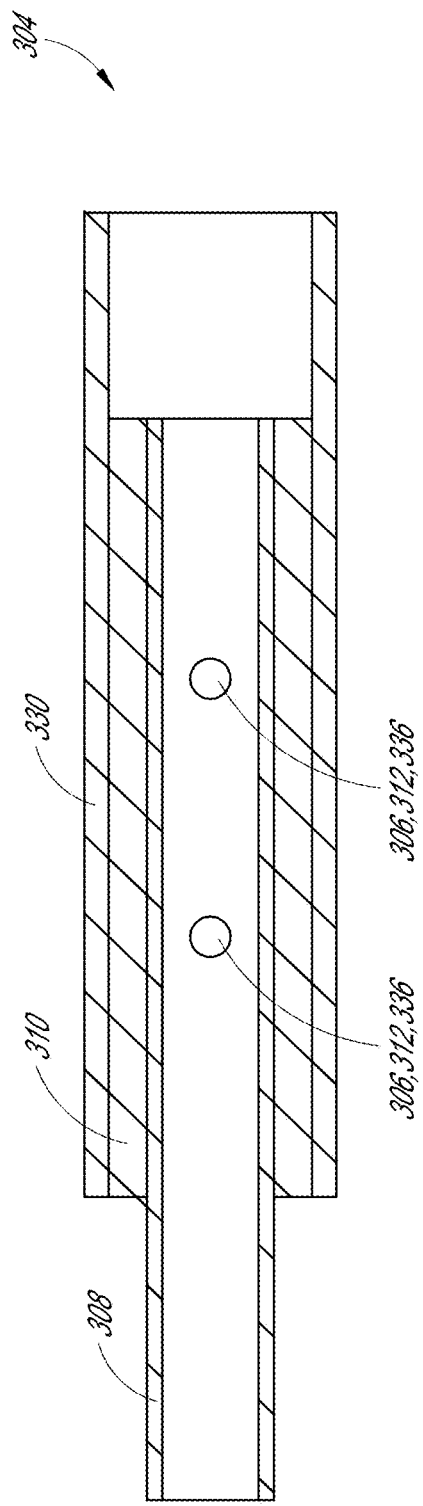
FIG. 3D illustrates a cross-section of an engagement of various components of the inner tube assembly of the sample therapeutic ultrasound device of FIG. 1A.

FIGS. 3A-3D illustrate various embodiments of the inner tube assembly 300. FIG. 3A illustrates an exploded view of the components of the inner tube assembly 300; FIG. 3B-3C illustrates a plurality of views of the distal end 302 and proximal end 304 of the inner tube assembly 300; and FIG. 3D illustrates a cross-sectional view of the intersection of the components of the inner tube assembly 300.

As shown in FIG. 3A, the inner tube assembly 300 can include the inner tube 308, a spacer 310, and a connector 330. In some embodiments, the proximal end of the inner tube 308 is configured to engage with the spacer 310 and the distal end of the connector 330. In some examples, the inner tube 308, spacer 310 and connector 330 comprise a material that is configured to withstand these forces. For example, any of the inner tube 308, spacer 310, and connector 330 can comprise double hard stainless steel tubing, aluminum, titanium, plastic, carbon fiber, etc. In some embodiments, the inner tube and the outer tube can be flexible or articulating. In some examples, the inner tube assembly 300 can be hollow to allow cables and/or wires to run from the distal end 102 to the proximal end 104 of the device.

As discussed with regard to the outer tube 206, the jaw assembly 400 can be configured to apply sufficient clamping or engagement pressure to the target tissue in order to generate sufficient force for treatment. To translate the force required for the device, the inner tube 308 can comprise a material that is configured to withstand these forces. For example, the inner tube 308 can comprise double hard stainless steel tubing, aluminum, titanium, plastic, carbon fiber, etc. In some embodiments, instead of a hollow tube, the inner tube 308 can instead comprise a solid pull rod (e.g., a rectangular pull rod). In examples where the inner tube 308 is solid instead of hollow, traces (rather than cables or wires) can be used to provide power to the distal end 102 of the device.

As seen in FIG. 3A, the proximal end of the inner tube 308 can include a plurality of openings 306. Similarly, the spacer 310 can include a plurality of openings 312 and the distal end of the connector 330 can include a plurality of distal openings 336. In some examples, the spacer 310 can be disposed over the proximal end of the inner tube 308 such that the plurality of openings 306 of the inner tube 308 aligns with the plurality of openings 312 of the spacer 310. In some embodiments, the spacer 310 is configured to provide an interference fit between the inner diameter of the connector 330 and the outer diameter of the inner tube 308. In some embodiments, the distal end of the connector 330 can be disposed over the spacer 310 and the proximal end of the proximal end of the inner tube 308. In some examples, the plurality of distal openings 336 of the connector 330 are configured to align with the plurality of openings 312 of the spacer 310 and the plurality of openings 306 at the proximal end of the inner tube 308.

FIG. 3D illustrates a cross section of the inner tube assembly 300 and an embodiment of the connection between the inner tube 308, spacer 310, and a connector 330. As noted above, the plurality of openings 306, 312, 336 can be aligned and secured by fasteners. In some embodiments, the fasteners securing the inner tube 308, spacer 310, and the connector 330 are a plurality of dowel pins 320. In some examples, the inner tube 308, spacer 310, and the connector 330 can be bolted, welded, screwed together, or glued.

In some embodiments, the inner tube assembly 300 can include the connector 330. As noted above, the connector 330 can be configured to secure the inner tube 308 with the proximal end 104 of the therapeutic ultrasound device 100 (e.g., the handle 120). In some examples, the proximal end of the inner tube assembly 300 and the outer tube assembly 200 is configured to interface with a device (e.g., other than the handle 120) that is configured to actuate the jaw assembly 400. For example, this can include a robotic articulating arm such that the therapeutic ultrasound device 100 can be used in a variety of applications (e.g., endoluminal, laparascopic, thoracoscopic procedures).

As noted above, the connector 330 can include a plurality of distal openings 336 at the distal end of the connector 330, a slot 334, and a proximal opening 332 at the proximal end of the connector 330. In some examples, the slot 334 is configured to allow the inner tube 308 of the inner tube assembly 300 to translate through the therapeutic ultrasound device 100. The retaining pin 230 can be held in place by the proximal opening 332 and fit into the slot 334 of the connector 330. In some embodiments, the proximal end of the connector 330 is free floating.

As noted above, in some embodiments, the distal end 302 of the inner tube assembly 300 can include a yoke 340 comprising a pair of arms. In some examples, each of the pair of arms of the yoke 340 includes an opening 342. In some embodiments, the opening 342 is configured to receive the inner tube pin 470.

As will be discussed in more detail below, the outer tube 206 can disposed over the inner tube 308 such that the yoke 240 of the outer tube 206 is disposed about the yoke 340 of the inner tube 308. In some examples, the openings 342 and the engaged inner tube pin 470 of the distal end 302 of the inner tube 308 are aligned with the slot 244 of the distal end 202 of the outer tube 206. This can allow the distal end 302 of the inner tube 308 to move the inner tube pin 470 within the slot 244 of the distal end 202 of the outer tube 206.

Jaws and Jaw Assembly

FIGS. 4A-4F illustrate an embodiment of individual jaws of the jaw assembly 400. Although only half of the jaw assembly 400 is illustrated in FIGS. 4A-4F, the jaw illustrated in FIGS. 4A-4F can describe the top jaw 402 and/or the bottom jaw 404.

In some embodiments, the jaws 402, 404 include an ear 420 on the proximal end 408 of the jaw 402, 404 and a body 430 on the distal end 406 of the jaw 402, 404. The jaw 402, 404 can include an opening 422 adjacent to the ears 420 and between the ear 420 and the body 430. As will be discussed in more detail below, the opening 422 can be configured to receive the pivot pin 460 such that the jaw 402, 404 can rotate about the pivot pin 460. In some embodiments, the jaw 402, 404 can be comprised of stainless steel or ceramics. In some examples, the jaws 402, 404 can have a width between 3 mm and 10 mm. In some embodiments, the jaws 402,404 can have a width between 1 mm and 15 mm. In some embodiments, the jaws 402, 404 can have any of the widths of 1 mm, 2 mm, 3 mm, 4 mm, 5 mm, 6 mm, 7 mm, 8 mm, 9 mm, 10 mm, 11 mm, 12 mm, 13 mm, 14 mm, and 15 mm. In some embodiments, the jaws 402, 404 can have a length between 5 mm and 100 mm. In some embodiments, the jaws 402, 404 can have a length between any of the ranges of 5 mm-10 mm, 10 mm-15 mm, 15 mm-20 mm, 20 mm-25 mm, 25 mm-30 mm, 30 mm-35 mm, 35 mm-40 mm, 40 mm-45 mm, 45 mm-50 mm, 50 mm-55 mm, 55 mm-60 mm, 60 mm-65 mm, 65 mm-70 mm, 70 mm-75 mm, 75 mm-80 mm, 80 mm-85 mm, 85 mm-90 mm, 90 mm-95 mm, or 95 mm-100 mm. In some embodiments, the jaws 402, 404 can have any of the lengths of 5 mm, 10 mm, 15 mm, 20 mm, 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, and 100 mm.

In some embodiments, the ear 420 includes a slot 424. The slot 424 can be curved (as shown in FIG. 4A), straight, or any other configuration. The slot 424 can be configured to receive the inner tube pin 470. As will be discussed in more detail below, movement of the inner tube pin 470 within the slot 424 can be configured to cause the pair of jaws 402, 404 of the jaw assembly 400 to move (e.g., open and close).

In some embodiments, the body 430 comprises an opening 434 configured to receive an acoustic stack (not shown). As shown in FIGS. 4A and 4E, the opening 434 can be rectangular in shape; however, the opening 434 can be any shape so long as it can receive and secure an acoustic stack. In some embodiments, the body 430 forms a shell 432. As will be discussed in more detail below, the shell 432 of the body 430 can be configured to provide an air-pocket for a transducer formed with the acoustic stack.

The base of the body 430 can further include an opening 490. The opening 490 can be configured to allow a cable (not illustrated) of the acoustic stack to be threaded through the opening 490. The cable can then be run through the outer tube assembly 200/inner tube assembly 300 where it is attached to the cable 150 (as shown in FIG. 1A). In this way, a power source can be provided to the acoustic stack to power the therapeutic ultrasound device 100.

In some embodiments, the distal end 406 of the jaw 402, 404 includes teeth 410. For example, as shown in FIGS. 4A-4E, the teeth 410 can be formed as wave-like folds in the distal end 406 of the jaw 402, 404 adjacent to the body 430. In other embodiments, the teeth 410 are formed along the edge of the distal end 406 of the jaw 402, 404 or along the entire perimeter of the body 430. The teeth 410 can have any shape or configuration, such as serrated, triangular, needlelike, etc. As well, the teeth 410 can be located on one or both of the jaws 402, 404. In some embodiments, as the jaw assembly 400 closes on the target tissue, the tissue can be inclined to move out of place. The teeth 410 are therefore configured to engage with and retain the target tissue as the jaw assembly 400 clamps downward.

FIGS. 5A-5D detail an example of the connection between the jaw assemblies 400 on the distal end 102 of the therapeutic ultrasound device 100. As discussed above, the jaw assembly 400 can be assembled to engage with the distal end 202 of the outer tube 206 and the distal end 302 of the inner tube 308. The jaw assembly 400 illustrated in FIGS. 5A-5D includes an acoustic stack 500 with a cable 440. In some examples, the proximal end of the jaw assembly 400 is configured to interface with a device (e.g., other than the distal end 202 of the outer tube 206 and the distal end 302 of the inner tube 308) that is configured to actuate the jaw assembly 400. For example, this can include a robotic articulating arm such that the therapeutic ultrasound device 100 can be used in a variety of applications (e.g., endoluminal, laparascopic, thorascopic procedures).

As discussed above, the outer tube 206 can be disposed over the inner tube 308 such that the pair of arms of the yoke 340 of the inner tube 308 are generally aligned with the pair of arms of the yoke 240 of the outer tube 206. This can be better seen in the cross-sectional view of FIGS. 5C and 5D where the outer tube 206 is disposed over the inner tube 308. To allow the inner tube 308 to fit within and move relative to the outer tube 206, the diameter of the inner tube 308 can be less than the outer tube 206. For example, the inner tube 308 can have a diameter of 0.103 inches and the outer tube 206 can have a diameter of 0.133 inches.

As seen in FIGS. 5A-5D the yoke 240 of the outer tube 206 and the yoke 340 of the inner tube 308 are spaced apart to allow the ears 420 of the jaw assembly 400 to fit between. In some embodiments, the pair of arms of the yoke 240 and the yoke 340 are sufficiently long such that there is clearance to allow the ears 420 of the top jaw 402 and the bottom jaw 404 to rotate freely about the pivot pin 460.

As discussed above, each of the pair of arms of the yoke 240 of the outer tube 206 can include an opening 242 and a slot 244. These openings, along with the opening 342 located in each of the pair of arms of the yoke 340 of the inner tube 308, are configured to retain and move the top jaw 402 and the bottom jaw 404 of the jaw assembly 400. As noted above, in some embodiments this can be accomplished using a combination of the pivot pin 460 and the inner tube pin 470.

As shown in FIGS. 5A-5D, the opening 422 of each of the top jaw 402 and the bottom jaw 404 are aligned with the openings 242 on each of the pair of arms of the yoke 240 of the outer tube 206. In some embodiments, a pivot pin 460 is fitted through and secured to the outer tube 206 such that the top jaw 402 and the bottom jaw 404 of the jaw assembly 400 are retained between the yoke 240 of the outer tube 206. The pivot pin 460 may also be configured to allow the top jaw 402 and the bottom jaw 404 to rotate about the pivot pin 460.

Figure 5A:
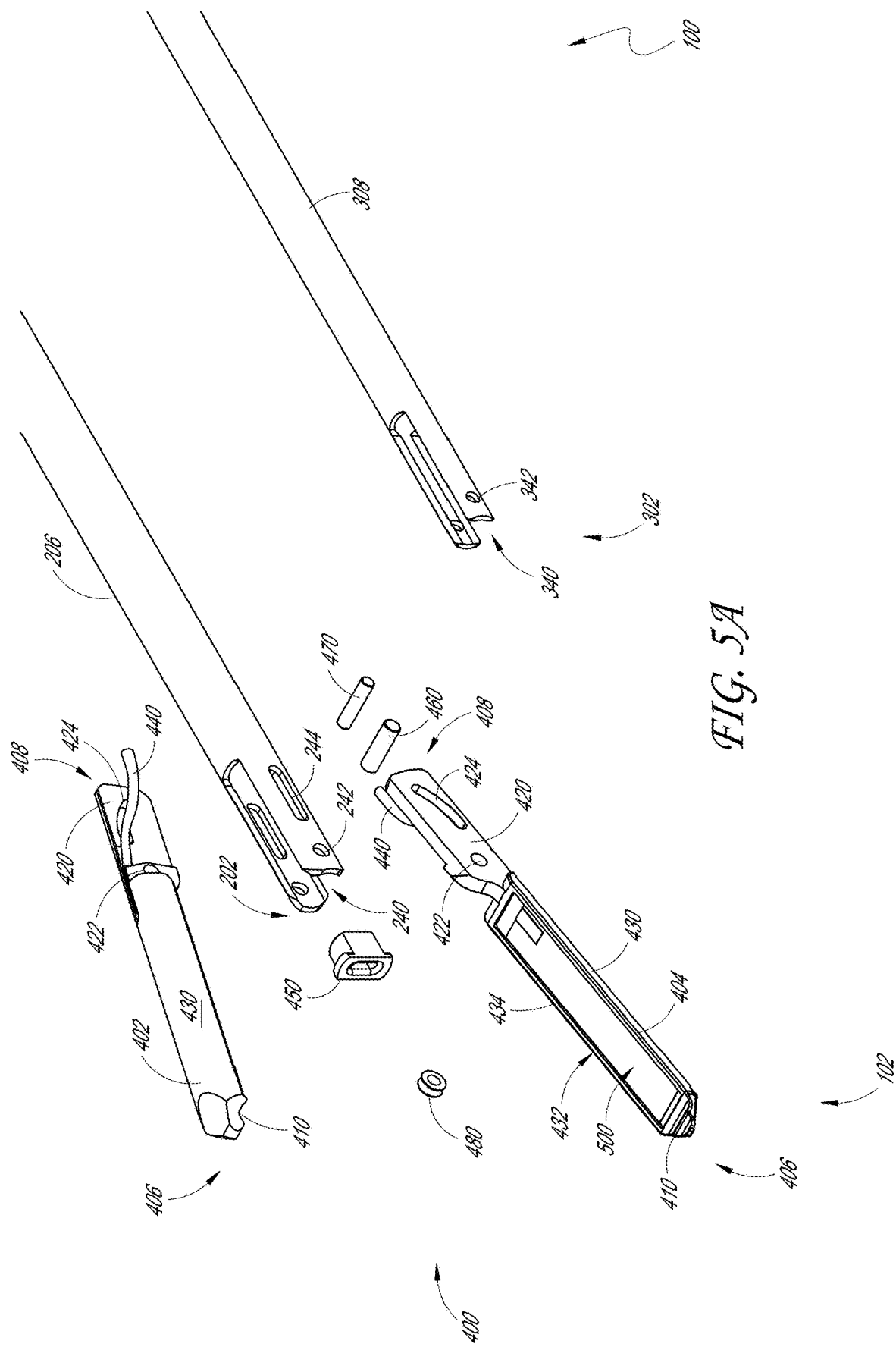
FIG. 5A illustrates an exploded view of the tissue engagement assembly located at the distal end of the sample therapeutic ultrasound device of FIG. 1A.
Figure 5C:
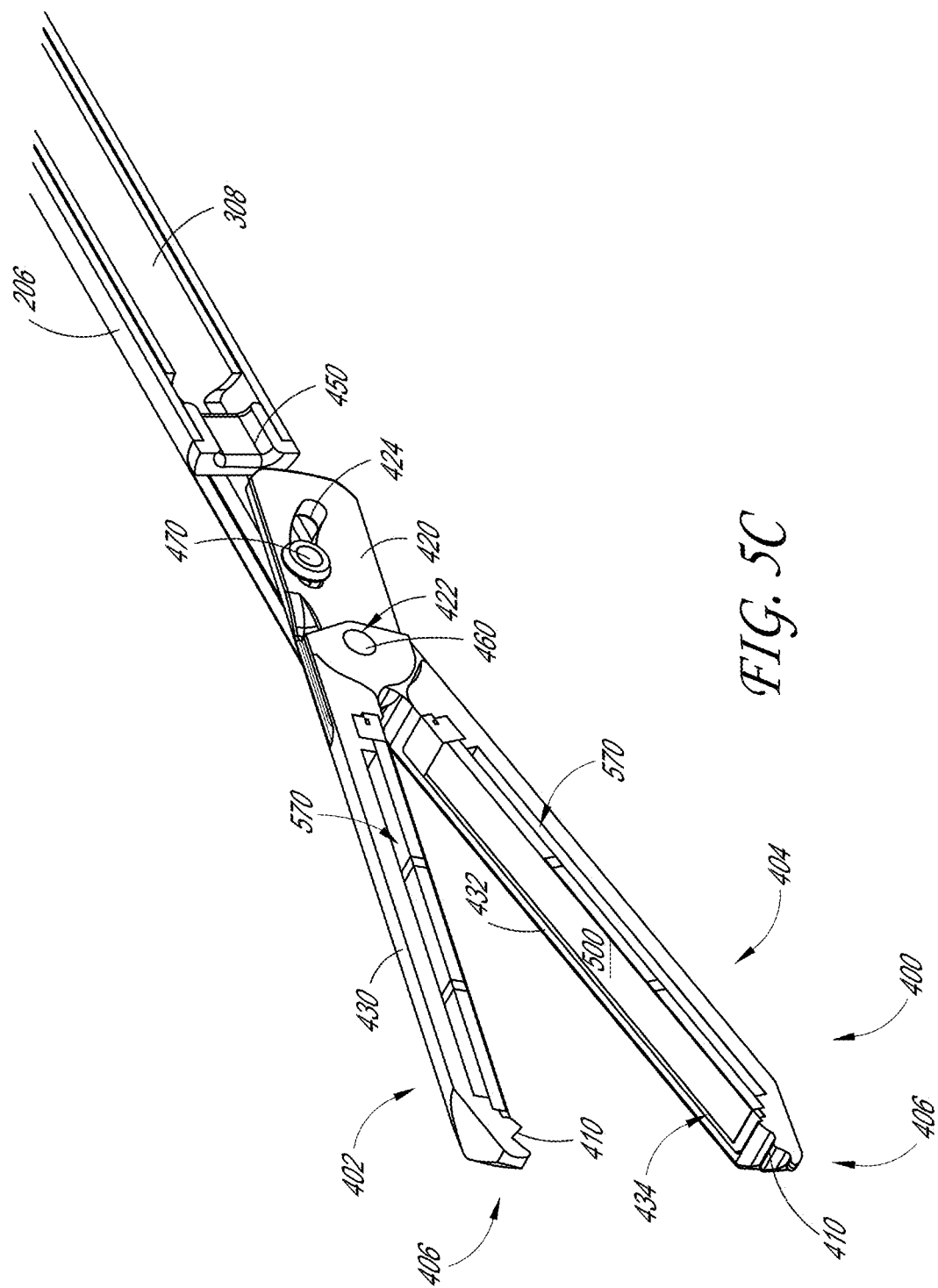
FIGS. 5C-5D illustrate cross-sectional views of the tissue engagement assembly located at the distal end of the sample therapeutic ultrasound device of FIG. 1A.
Figure 5D:
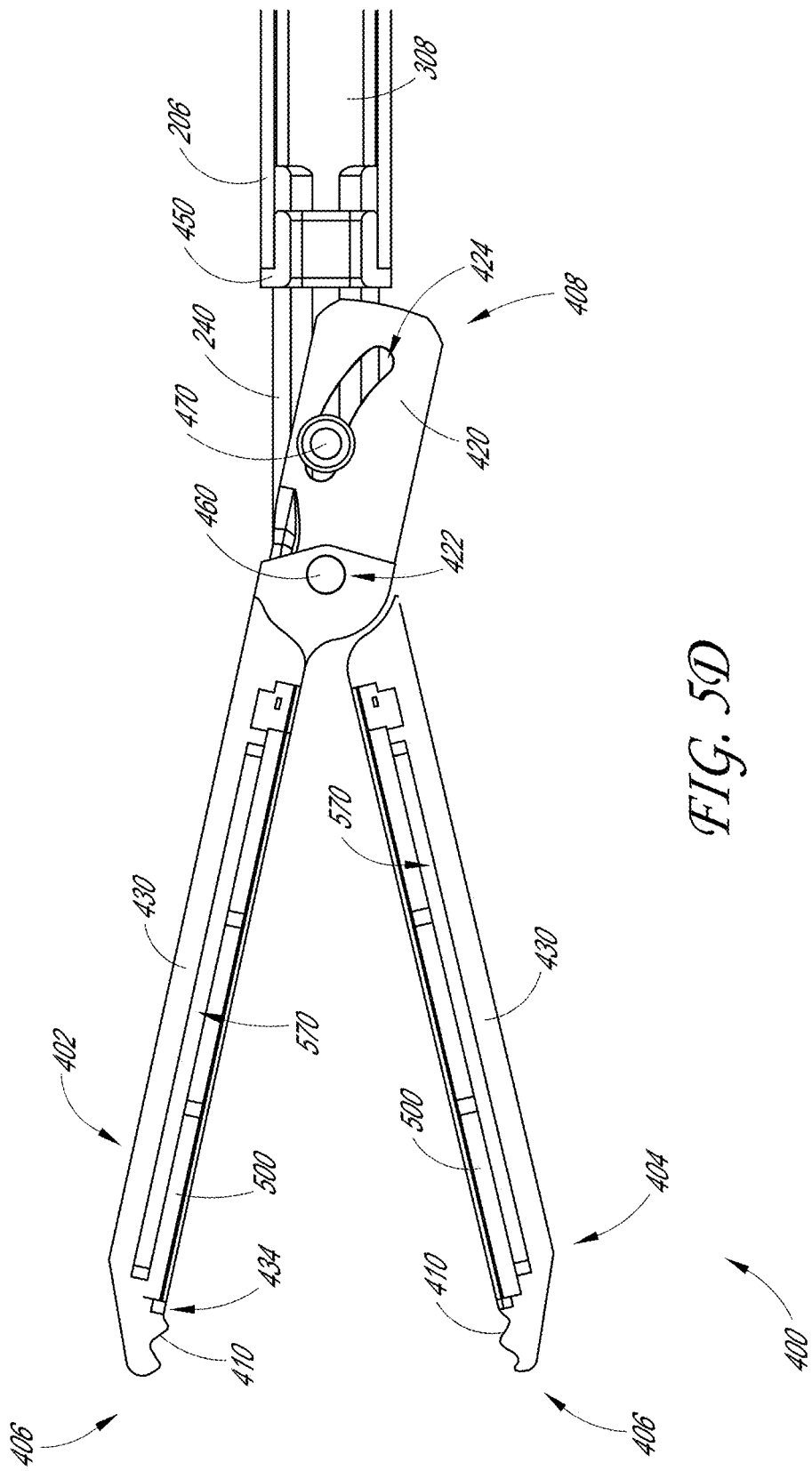

As discussed above, the inner tube pin 470 can be configured to cause the top jaw 402 and the bottom jaw 404 of the jaw assembly 400 to open and close. As shown in FIGS. 5A through 5D, the opening 342 in the pair of arms of the yoke 340 is aligned with the slot 244 in the pair of arms of the yoke 240. As illustrated in FIGS. 5B-5D, the ears 420 of the top jaw 402 and the bottom jaw 404 of the jaw assembly 400 are located between the yoke 340, such that a portion of the slot 424 intersects the plane on which the slot 244 of the outer tube 206 extends.

As better seen in the cross-sectional views in FIGS. 5B-5D, the inner tube pin 470 can be fitted through and secured to each of the openings 342. In some embodiments, the inner tube pin 470 is press-fit into the bushing 480. In some embodiments, ends of the inner tube pin 470 are configured to extend through the slot 244 of the outer tube 206 such that the inner tube pin 470 can move freely along the slots 424. The inner tube pin 470 can also be fitted through each of the slots 424 of the ears 420 in the top jaw 402 and bottom jaw 404. This configuration can allow the inner tube 308 to advance or retract the inner tube pin 470 along the slot 244 as the inner tube 308 can be advanced or retracted relative to the outer tube 206. As the inner tube pin 470 moves along the length of the slot 244, the inner tube pin 470 is configured to move along the track of the slot 424 in each of the ears 420. As the inner tube pin 470 moves in a first direction, the inner tube pin 470 moves to a first end of the slot 424, causing the jaw assembly 400 to open. Similarly, as the inner tube pin 470 moves in a second direction, the inner tube pin 470 moves to a second end of the slot 424, causing the jaw assembly 400 to close.

In some embodiments, a wire guide 450 is configured to fit within the outer tube 206 distal to the inner tube 308. The wire guide 450 may be configured to protect the wires located between the ears 420 of the jaws 402, 404 such that the wires are not impinged in the jaws 402, 404. The wire guide 450 may include an opening to receive the cable 440 and guide it along the length of the interior of the inner tube 308. In some embodiments the wire guide 450 can be comprised of a compliant material. For example, the material can be a thermoplastic such as a resin polymer.

In some embodiments, the jaw assembly 400 includes a bushing 480. As noted above, the bushing 480 can be located between the ears 420 of the top jaw 402 and the bottom jaw 404. The bushing 480 can be configured to secure the pivot pin 460 in place and to maintain the space between the ears 420 of the top jaw 402 and the bottom jaw 404. The bushing 480 can, for example, keep the ears 420 of the top jaw 402 and the bottom jaw 404 separated such that the wires do not get impinged. As well, the bushing 480 can be configured to retain the draw pin 470. As discussed above, in some examples, the draw pin 470 is pressed into the bushing 480. The bushing 480 may also or alternatively be configured to prevent rotation of the top jaw 402 and the bottom jaw 404 within the jaw assembly 400. In some embodiments, the bushing 480 can be comprised of a material such as stainless steel.

FIG. 5E illustrates a cross-sectional view of the distal end 102 of the therapeutic ultrasound device 100 through the pivot pin 460. As illustrated, the plurality of ears 420 of the top jaw 402 and the bottom jaw 404 are located between the pair of arms of the yoke 240 of the outer tube 206. In some embodiments, as discussed above, the pivot pin 460 extends through the openings 422 in the top jaw 402 and the bottom jaw 404 to allow the pair of jaws to rotate. As noted above, the wire guide 450 can be located near the base of the yoke 240 and adjacent to the ears 420.

FIG. 5F illustrates a cross-sectional view of the distal end 102 of the therapeutic ultrasound device 100 through the inner tube pin 470. As noted above, the inner tube pin 470 can extend through the slot 244 of the outer tube 206 and through the distal end 302 of the yoke 340. In some embodiments, the inner tube pin 470 also extends through the slot 424 in each of the top jaw 402 and the bottom jaw 404. A bushing 480 can be located between the ears 420 of the pair of jaws of the jaw assembly 400. As discussed, this can help to maintain the space between the ears 420 of the pair of jaws of the jaw assembly 400 and prevent rotation of the pair of jaws of the jaw assembly 400.

The jaw assembly 400 can be configured such that both the top jaw 402 and the bottom jaw 404 are movable. In some embodiments, only one of the pair of jaws of the jaw assembly 400 is movable. In some embodiments, the top jaw 402 and bottom jaw 404 form an angle when open and the movement of the top jaw 402 and the bottom jaw 404 is a scissor-like movement. In other embodiments, the top jaw 402 and the bottom jaw 404 are parallel to one another and open and close such that the pair of jaws remain in parallel with one another.

Acoustic Stack

In some embodiments, the therapeutic ultrasound device 100 can include an acoustic stack 500 within each jaw of the jaw assembly 400. In some embodiments, the jaw assembly 400 can include a jaw with an acoustic stack 500 and a jaw without an acoustic stack. FIGS. 6A-6C, 7A-7C, and 8A-8C illustrate a plurality of embodiments of the acoustic stack 500.

Figure 6C:
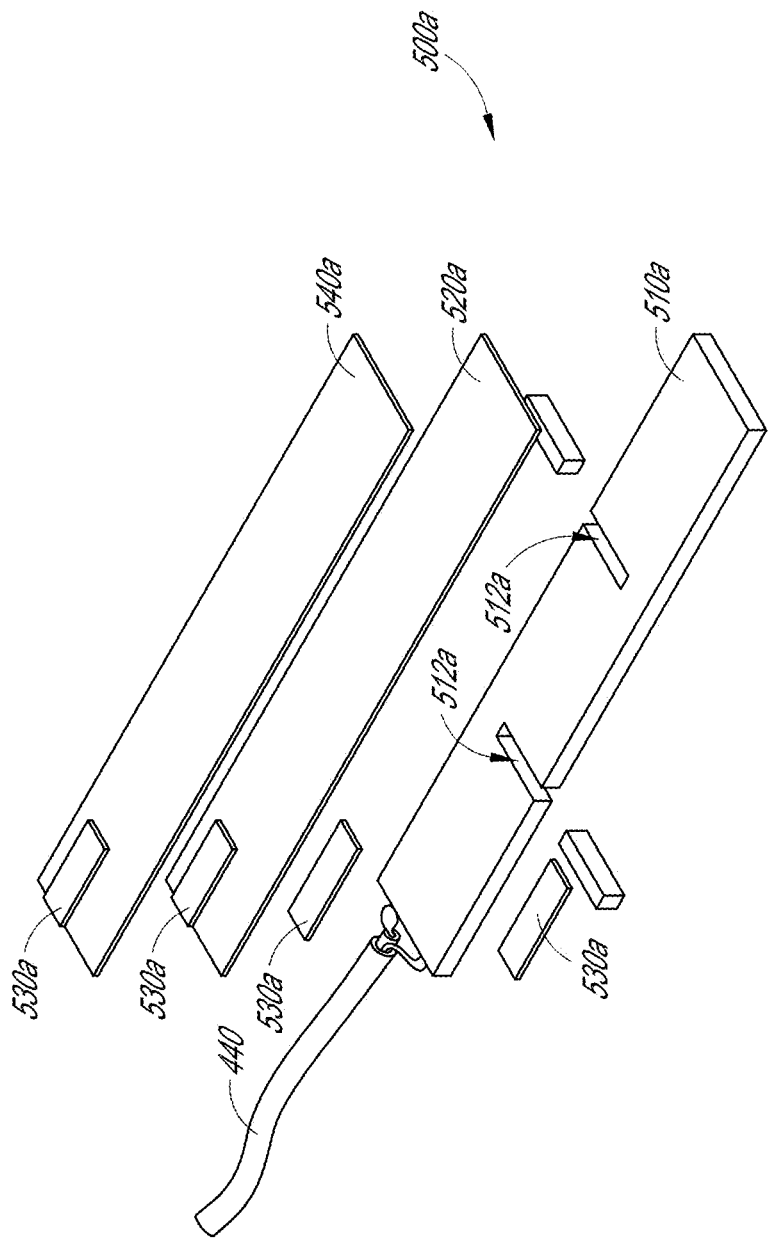
FIG. 6C illustrates an exploded view of a first embodiment of the acoustic stack of FIGS. 6A-6B.

FIGS. 6A-6C illustrate a first embodiment of an acoustic stack 500a. The acoustic stack 500a can include an acoustic wave generating layer 510a layer, an adhesive 520a layer, and a matching layer 540a. In some embodiments, the 510a layer is a piezoelectric transducer (PZT). In some embodiments, the 510a layer can be a capacitive machined ultrasound transducer (CMUT) or any other silicon chip comprising machined drums that are configured to apply a voltage and pulse. In some examples, the 510a layer can have a width of 2.6 mm and a length of 15 mm.

In some examples, the matching layer 540a is configured to allow the transmission of acoustic energy into a target site by matching the acoustic wave propagation from the 510a layer (e.g., the PZT layer) to the target tissue. As the frequency of the acoustic wave is a function of the thickness and type of material passing through it, the matching layer 540a is configured to prevent the wave from getting reflected from the target tissue. In order for a wave to propagate from one material to the next they should have similar acoustic impedances. If there is an impedance mismatch the wave is reflected. The degree of reflection depends on the degree of mismatch.

One or more electrodes 530a can be located on an end of the acoustic stack 500a between each layer of the PZT 510a, adhesive 520a, and matching layer 540a. In some embodiments, the electrodes 530a can comprise copper. In other embodiments the electrodes 530a can comprise any conductive material. A cable 440 can be located on an end of the acoustic stack 500a and electrically in contact with the electrodes 530a to provide power to the acoustic stack 500a. In some embodiments, as shown in FIG. 6C, the PZT 510a can include a plurality of slots 512a. The slots 512a can be configured to can be configured to produce a more uniform acoustic field along the length of the transducer 600a.

Figure 7C:
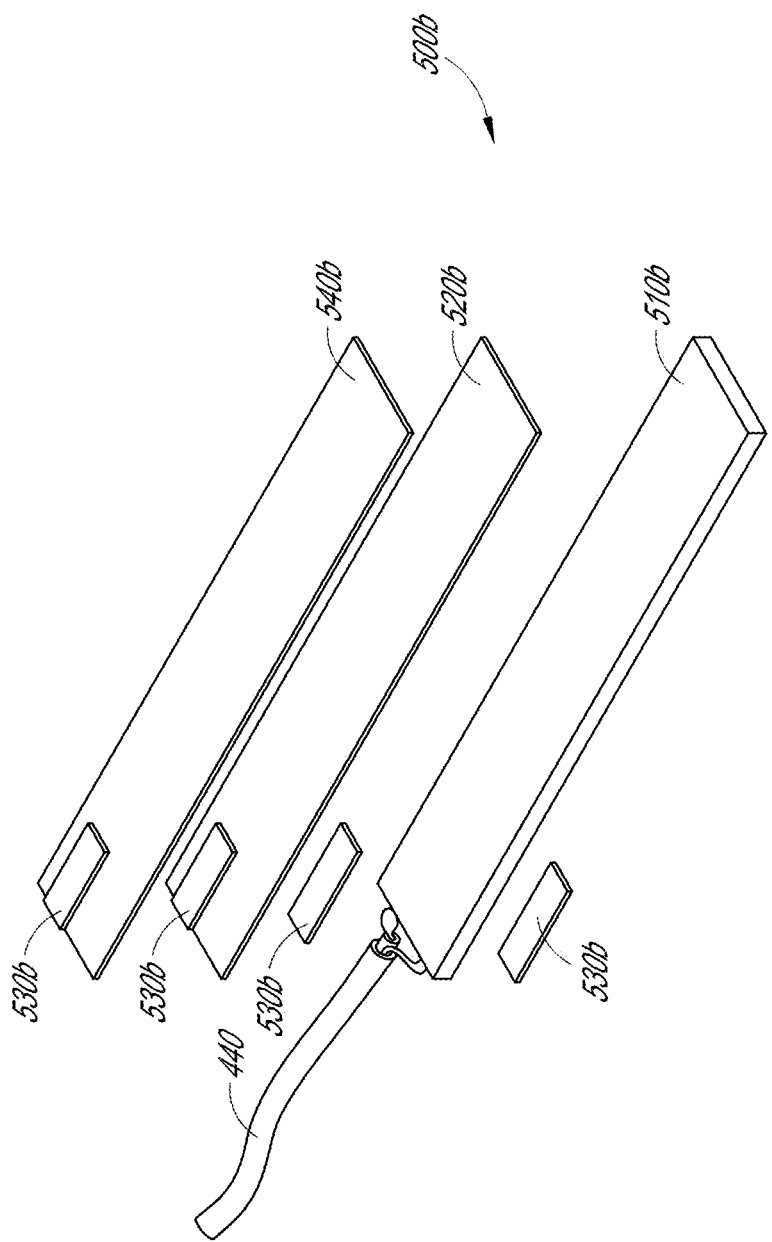
FIG. 7C illustrates an exploded view of a second embodiment of the acoustic stack of FIGS. 7A-7B.

FIGS. 7A-7C illustrate a second embodiment of an acoustic stack 500b. As with the acoustic stack 500a, the acoustic stack 500b can include a PZT 510b layer, an adhesive 520b layer, and a matching layer 540b. One or more electrodes 530b can be located on an end of the acoustic stack 500b between each layer of the PZT 510b, adhesive 520b, and matching layer 540b. As with the acoustic stack 500a, a cable 440 can be electrically connected to the plurality of electrodes 530b to provide power to the acoustic stack 500b.

Figure 8C:
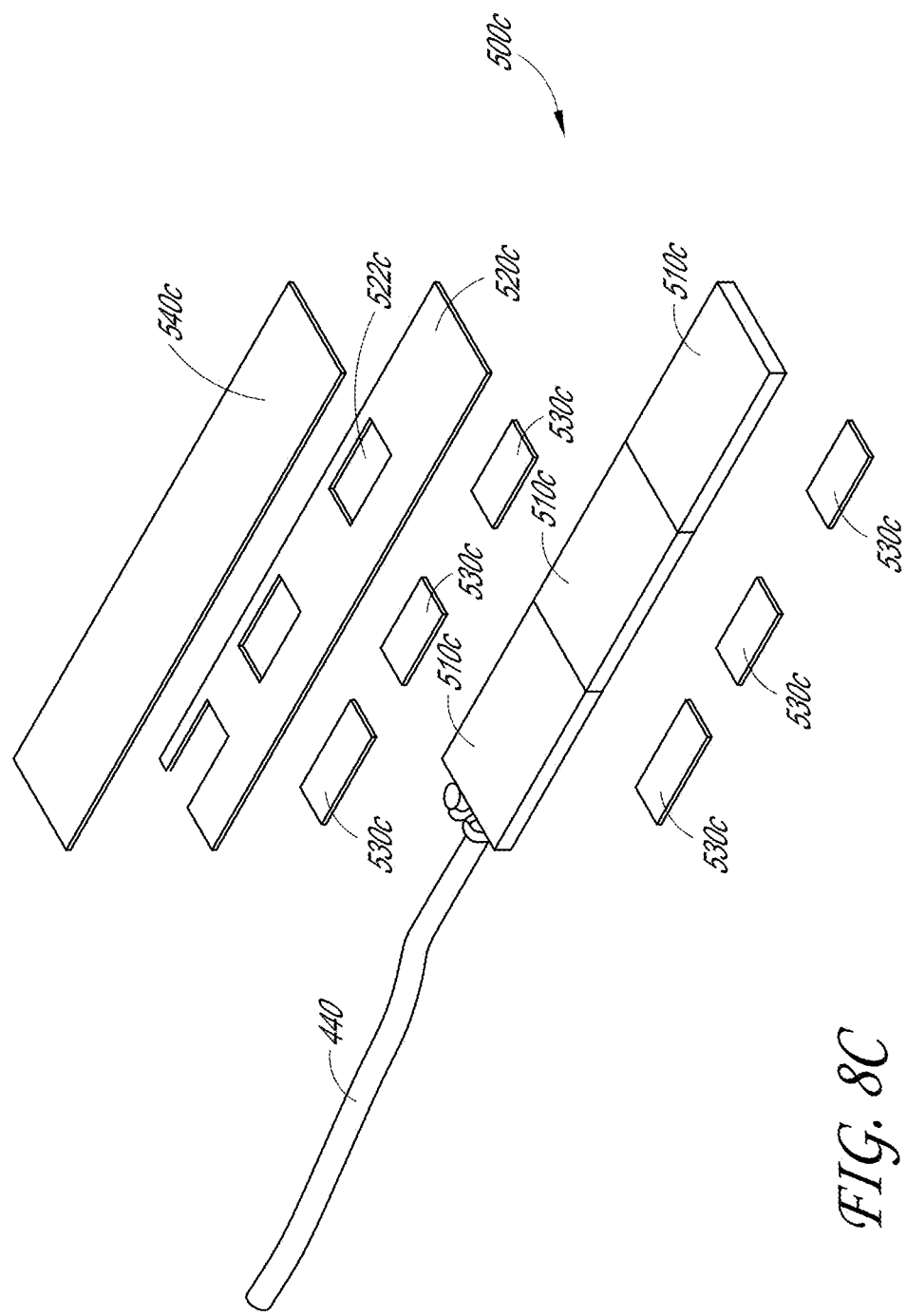
FIG. 8C illustrates an exploded view of the third embodiment of the acoustic stack of FIGS. 8A-8B.

FIGS. 8A-8C illustrate a third embodiment of an acoustic stack 500c. As discussed with regard to the acoustic stack 500a, 500b, the acoustic stack 500c can include a PZT 510c layer, an adhesive 520c layer, and a matching layer 540c. As illustrated in FIG. 8C, the PZT 510c layer can comprise a plurality of side-by-side PZTs. In the example shown, the PZT 510c layer includes three (3) adjacent PZTs. One or more electrodes 530c can be located in layers above and below the PZT 510c layer. As shown in FIG. 8C, the electrodes 530c can be aligned above and below the PZT 510c layer such that each of the plurality of PZTs 510c are connected by an electrode 530c. In some embodiments, as seen in FIG. 8C, the adhesive 520c can be configured to receive a plurality of electrodes 530c. A cable 440 can be electrically connected to at least one of the plurality of electrodes 530c to provide power to the acoustic stack 500c.

The matching layer 540 in each of the above-described embodiments of the acoustic stack 500 can be configured to adapt the sound speed of the PZT 510 with the sound speed through the tissue to which the therapeutic ultrasound device is being applied, which tissue may have a higher impedance. The matching layer 540 can comprise graphite or fluoropolymer and the surface of the matching layer 540 can be coated with parylene or any other material that provides the matching layer 540 with a nonstick and/or biocompatible surface.

In some embodiments, the matching layer 540 can be attached to the surface of the PZT 510 with the adhesive 520 layer. The adhesive 520 layer can be an epoxy or a layer of metal formed from soldering the PZT 510 to the matching layer 540.

As will be discussed in more detail below, each of the acoustic stacks 500a, 500b, and 500c are configured to be secured in at least one of the jaws 402, 404 of the jaw assembly 400. The acoustic stack, when secured in the jaw 402, 404 forms a transducer that can produce therapeutic ultrasound. As each of the acoustic stacks 500a, 500b, 500c are simplistic in construction, the transducer formed is capable of producing a higher intensity of energy in comparison to other transducer constructions currently in existence. In this way, the small size of the jaw assembly (e.g., 3 mm-15 mm) can efficiently seal and/or cut tissue.

Each of the acoustic stacks 500a, 500b, and 500c are configured to provide the acoustic field and power described above. In some embodiments, each of the acoustic stacks 500a, 500b, 500c provide for varying resultant acoustic field maps when driven in water. Each of the acoustic stacks 500a, 500b, and 500c differ in the complexity in construction. In some examples, the acoustic stack 500b has the most simplistic construction compared to the construction of the acoustic stack 500c.

Transducer and Relationship Between Applied Power and Force

In some examples, as discussed above, by placing the ultrasound transducers on opposing arms of a clamp, we achieve a well-confined and controlled high intensity region midline between the transducers where the absorbed energy cauterizes the tissue progressing from the midline toward the transducers resulting in a complete plane of cauterization. Particularly where DTU is used, significant collateral damage due to high focal gains and long transmission paths through intervening tissue can be avoided and instead provide for invasive or minimally-invasive procedures. The use of DTU can provide the ability to induce planes of cauterization/ablations to treat volumes (up to ~30 cm$^3$) of tissue in seconds as opposed to the raster scanning technique frequently required with transcutaneous HIFU. Existing raster scanning can require long treatment times (e.g., hours) to ablate a comparable volume as ablated using the presently disclosed device.

In some embodiments, ablation occurs in seconds due to the heat generation via ultrasound absorption and because the high intensity region is well-contained within the midline of the transducer heads. In the disclosed device, there is no collateral thermal spreading beyond the region of interest, and the face of the transducers does not heat excessively, thus preventing tissue adhering to the applicator. Ablated tissue is resorbed by the body similar. The disclosed device has a considerable advantage over existing ablative technologies in that ablation and hemostasis can be reached in significantly quicker treatment time and any complications due to thermal spreading and tissue adherence to the device are fully avoided. In conjunction with the innovative therapy modality/device, ultrasound also affords the ability to interrogate the treated region to evaluate the progression of the therapy with the same transducers that are administering the therapy.

In some embodiments, to provide treatment at a target site, sufficient clamping force and power from the jaw assembly 400 must be delivered. Particularly when the jaw assembly 400 is within the 3 mm-15 mm range, the configuration of the transducers of the jaw assembly 400 can be relevant to providing sufficient power to the target site.

In most constructions of transducers, the transducer includes a backing layer, a copper electrode layer, a PZT layer, a second copper electrode layer, and another backing layer. Each of these layers, in particular the plurality of backing layers, provide an increased resistance that limits the power that can be delivered by the transducer. However, conventional transducers are built with these components to form a transducer that can be operated over a broad range of frequencies.

Figure 9B:
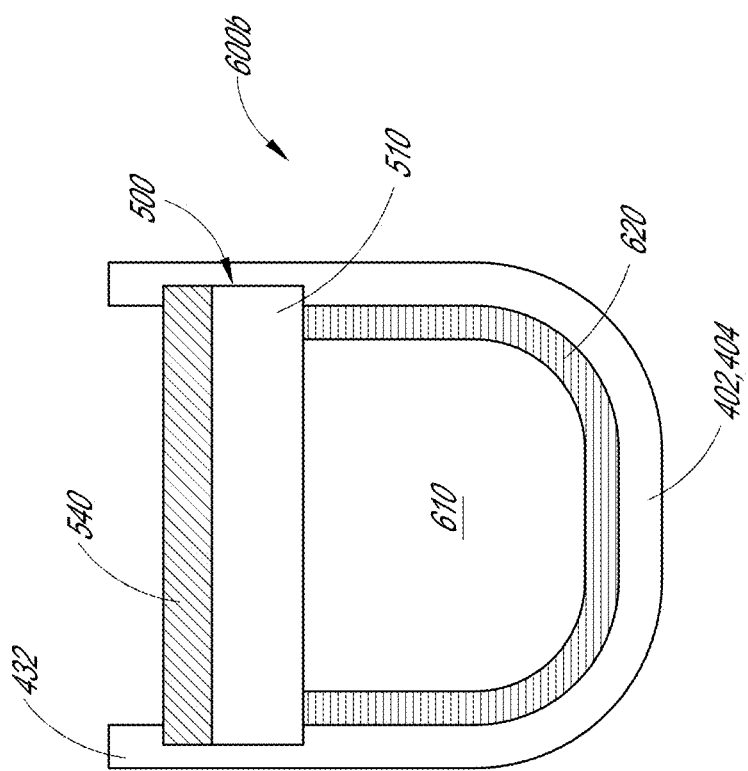
FIG. 9B illustrates a cross-sectional view of another embodiment of a transducer formed from one of the jaws of the tissue engagement assembly of the sample therapeutic ultrasound device of FIG. 1A, and configured to receive any of the disclosed acoustic stacks illustrated in FIGS. 6A-6B, 7A-7B, and 8A-8B.
Figure 9A:
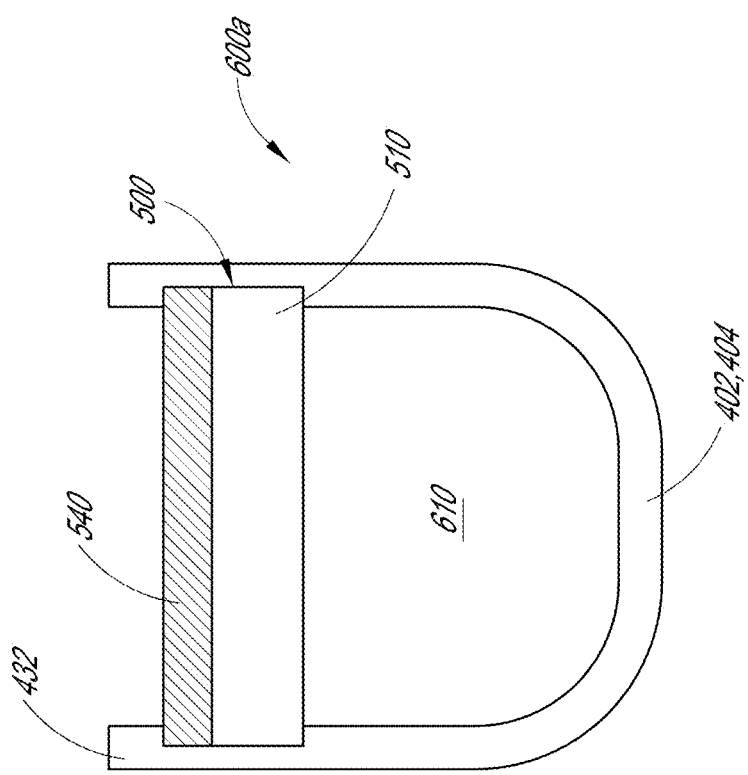
FIG. 9A illustrates a cross-sectional view of an embodiment of a transducer formed from one of the jaws of the tissue engagement assembly of the sample therapeutic ultrasound device of FIG. 1A, and configured to receive any of the disclosed acoustic stacks illustrated in FIGS. 6A-6B, 7A-7B, and 8A-8B.

In contrast, the disclosed therapeutic ultrasound device 100 includes a transducer in the jaw assembly 400 that is constructed to operate within a narrow range of frequencies so as to provide for greater power/cm³. In some embodiments, the transducer can be designed to work at any ultrasound frequency. For example, the transducer can be designed to work between 1 MHz and 10 MHz. In some embodiments, the disclosed transducer of the therapeutic ultrasound device 100 is driven by a radio frequency (RF) signal generator that produces between 10 W to 200 W of electricity. The transducer of the therapeutic ultrasound device 100 is configured to convert the electrical power into acoustic power. The disclosed transducer of the therapeutic ultrasound device 100 is configured to function at between 60%-80% efficiency. For example, the acoustic power generated by the transducer is approximately 200 Watts. FIGS. 9A and 9B illustrate cross-sectional embodiments of each of the pair of jaws 402, 404 that form transducer 600a and transducer 600a. Each and/or both of these embodiments can be formed within the jaw assembly 400.

FIG. 9A illustrates an embodiment of the transducer 600a in one or both of the jaws 402, 404. As shown, the transducer 600a can include an acoustic stack 500 located in the shell 432 of the jaws 402, 404. As discussed above, the acoustic stack 500 can comprise a matching layer 540 and a PZT 510. In contrast to conventional transducers that include a backing layer, the disclosed transducer 600a has an air-filled pocket 610 backing that is configured to ensure high efficiency as ultrasound does not travel well through air. The acoustic wave generating layer (e.g., PZT 510 layer), is configured to generate acoustic waves through both sides of the 510 layer. As air is the greatest impedance mismatch possible for an acoustic wave generator (e.g., PZT), the air-filled pocket 610 causes most of the acoustic wave to be reflected back on the air-filled side and into the tissue.

Figure 14:
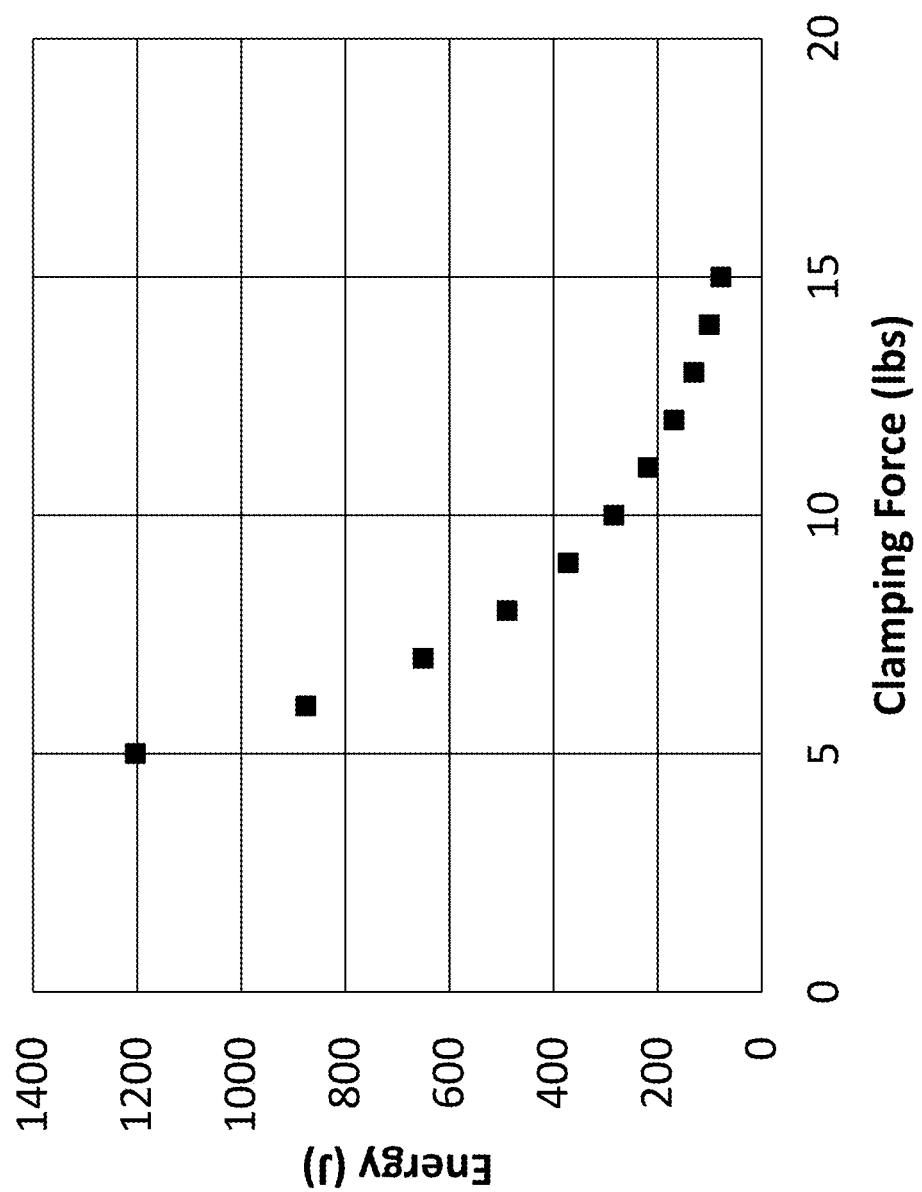
FIG. 14 illustrates an example of the relationship between energy and clamping force as it relates to sealing and dividing tissue.

As noted above, the present construction of the transducer does not include the many layers present (e.g., the plurality of electrode layers and backing layers) in conventional construction of transducers. The embodiments of the transducer 600a therefore encounters less impedance and can generate significantly more power over a relatively short distance when compared to conventional transducers. As well, the fewer layers included in a transducer reduces the amount of loading the PZT layer experiences. This can therefore enable the PZT layer to generate more acoustic power at a given electrical power. This increased power, along with the force that can be produced in the jaw assembly of the therapeutic ultrasound device 100 disclosed above, can allow the relatively small size of the jaw assembly 400 (e.g., 3 mm-15 mm) to seal and/or cut tissue at a target location over a short amount of time. The ability of the therapeutic ultrasound device 100 to seal and/or divide tissue is a function of energy delivered to the tissue, the pressure with which the tissue is clamped, and the amount of time treatment is applied (e.g., Power=Energy/Time). An example of this relationship is illustrated in FIG. 14.

FIG. 9B illustrates another embodiment of the transducer 600b that can be formed in one or both of the jaws 402, 404. Similar to the transducer 600a, the transducer 600b can include an acoustic stack 500 located in the shell 432 of the jaws 402, 404. As well, the acoustic stack 500 can comprise a matching layer 540 and a PZT 510. In addition to the air-filled pocket 610, the transducer 600b includes a lining 620 that serves to further electrically isolate the inside surface of the shell 432. As discussed with regard to the air-filled pocket 610, the lining 620 is configured to further improve the efficiency of the ultrasound. In some examples, the lining 620 comprises a heat resistant polymer. In some embodiments, the lining 620, by further electrically isolating the inside surface of shell 432, further prevents the power generated from the transducer from being dissipated. As noted above, this can increase the power generated in the transducer 600b. Along with the force that can be produced in the jaw assembly 400 of the therapeutic ultrasound device 100 disclosed above, the configuration of the transducer 600b can allow the relatively small size of the jaw assembly 400 (e.g., 3 mm-15 mm) to seal and/or cut tissue at a target location over a short amount of time. As discussed above, the ability of the therapeutic ultrasound device 100 to seal and/or divide tissue is a function of energy delivered to the tissue, the pressure the tissue is clamped with, and the amount of time treatment is applied (e.g., Power=Energy/Time).

In some embodiments, when the jaw assembly 400 of the therapeutic ultrasound device 100 engages a target site, the transducer 600a, 600b can launch an acoustic wave toward the target site in a medium (e.g., tissue) and receive echoes as the acoustic wave reflects off the tissue. For example, a wavelength of 0.15 mm can be produced using 10 MHz, a wavelength of 0.3 mm can be produced using 5 MHz, a wavelength of 0.4 mm can be produced using 3.5 MHz, and a wavelength of 1.5 mm can be produced using 1 MHz. In some examples, the target site may be diseased or not diseased tissue, muscle, vasculature, etc. In some examples, the transmitted ultrasound waves can become nonlinear as they propagate through the tissue, and the nonlinear propagation can generate harmonics in the acoustic beam that develop at or near the focal region of the transducer 600a, 600b from which they are transmitted. In some embodiments, at the focal region, the harmonic content can cause acoustic beam narrowing, enhanced tissue heating and proximal focal shifts. In some examples, the focal region can refer to a point, area, or volume at which the intensity of the transducer 600a, 600b source is the highest.

Figure 11:
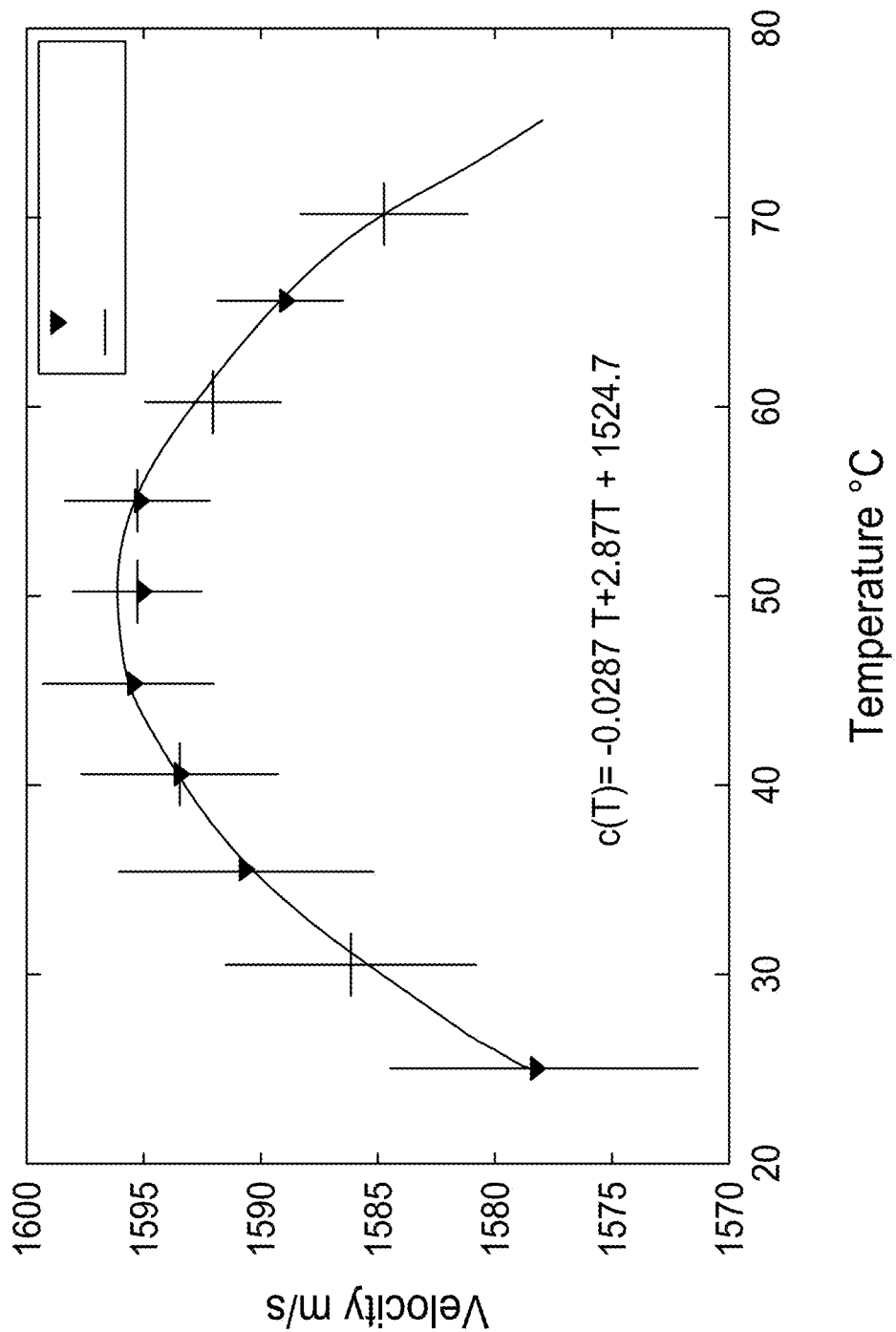
FIG. 11 illustrates the relationship between the velocity of sound in tissue and temperature.

As illustrated in FIGS. 14A-14D, the tissue can be heated to between 40° C. and 100°. As illustrated in FIG. 11, the velocity of sound in tissue is temperature dependent. As the tissue temperature increases to approximately 50° C., protein denaturation occurs and results in an inflexion point in the slope of the sound velocity vs. temperature plot. Near 50° C., the slope can be zero.

Figure 12A:
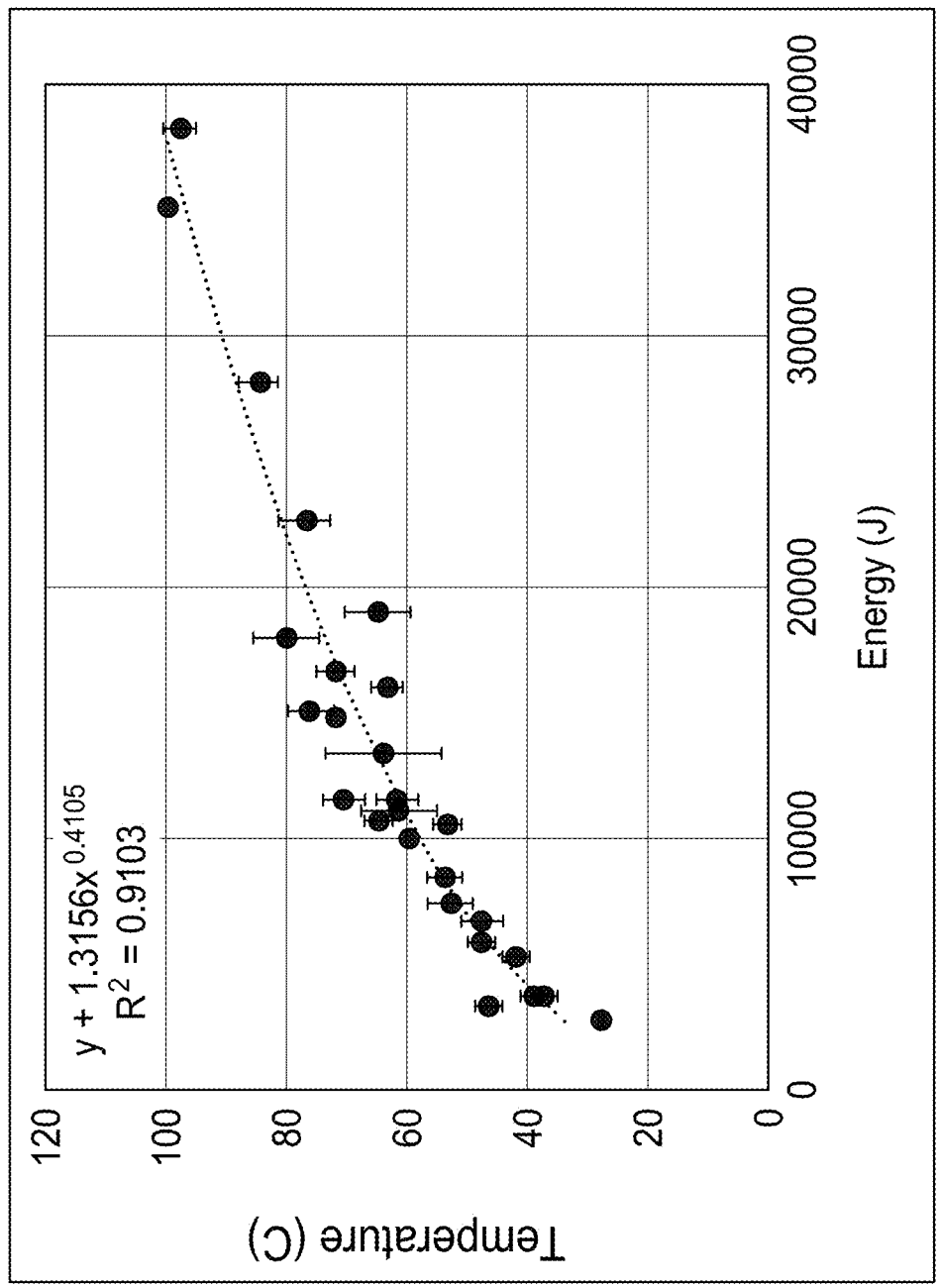
FIG. 12A illustrates the relationship between the maximum temperature and acoustic energy with time fixed.
Figure 12B:
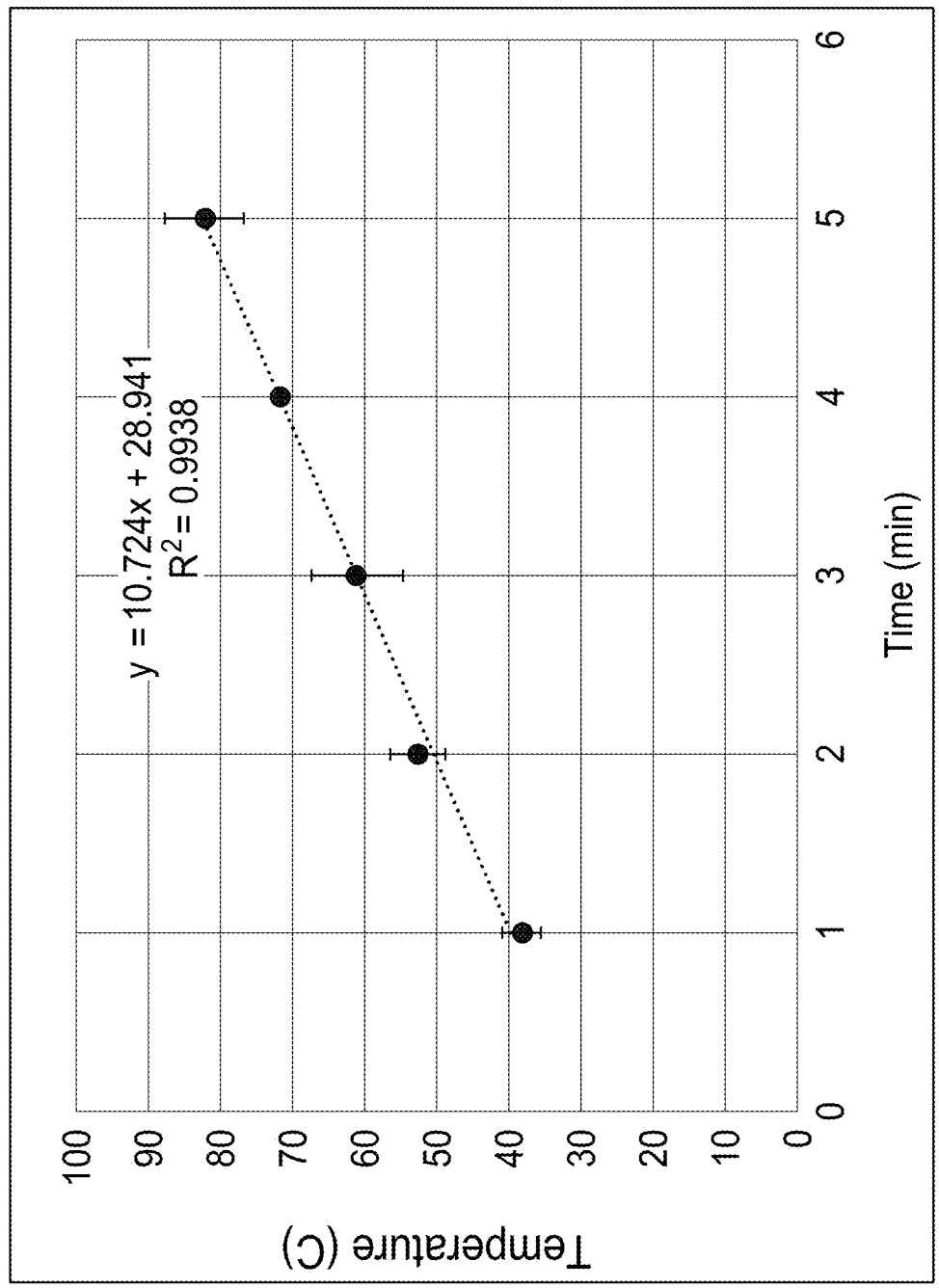
FIG. 12B illustrates the relationship between maximum temperature and time with power and intensity fixed.
Figure 12C:
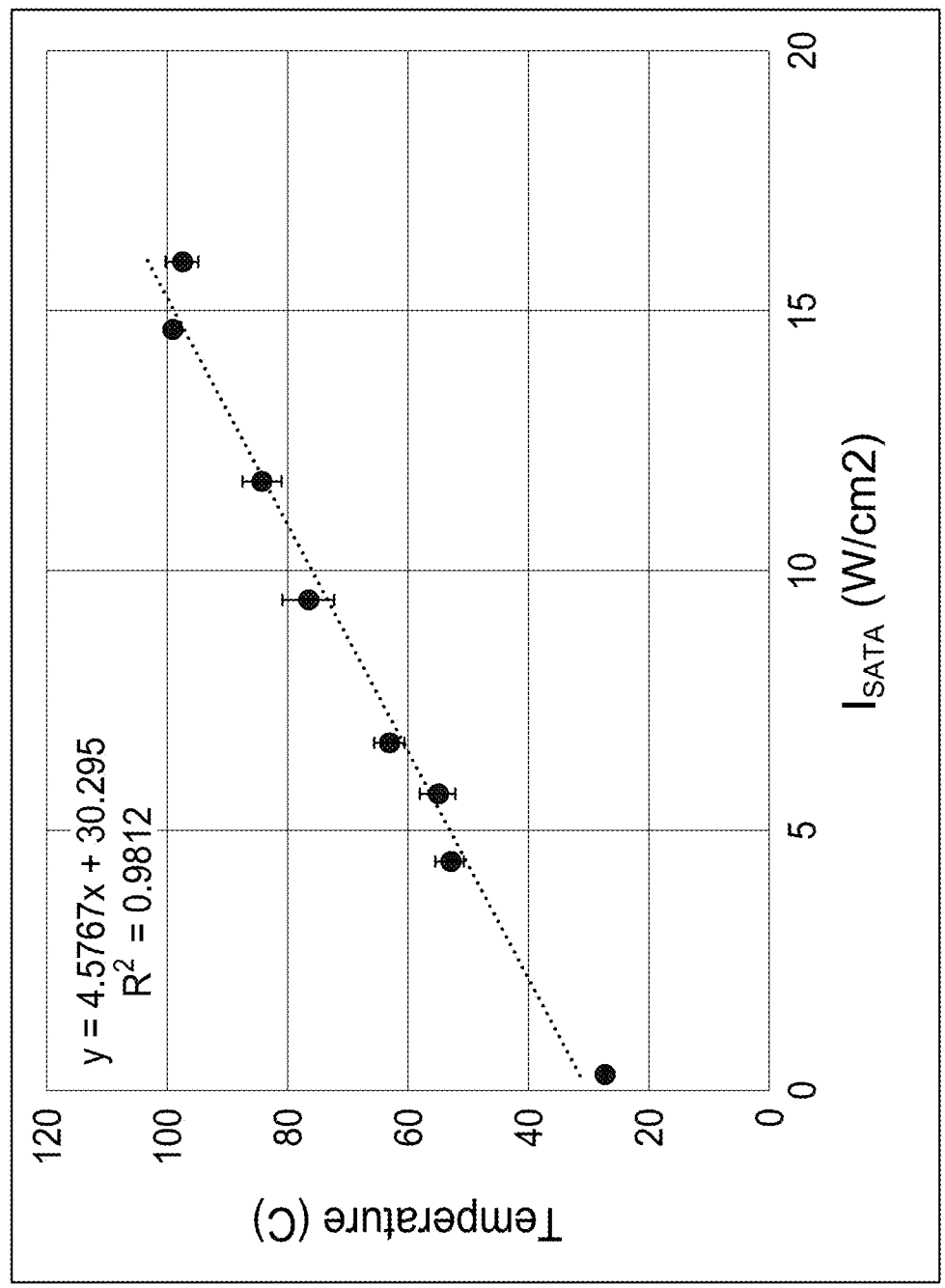
FIG. 12C illustrates the relationship between the maximum temperature and intensity with time fixed.
Figure 12D:
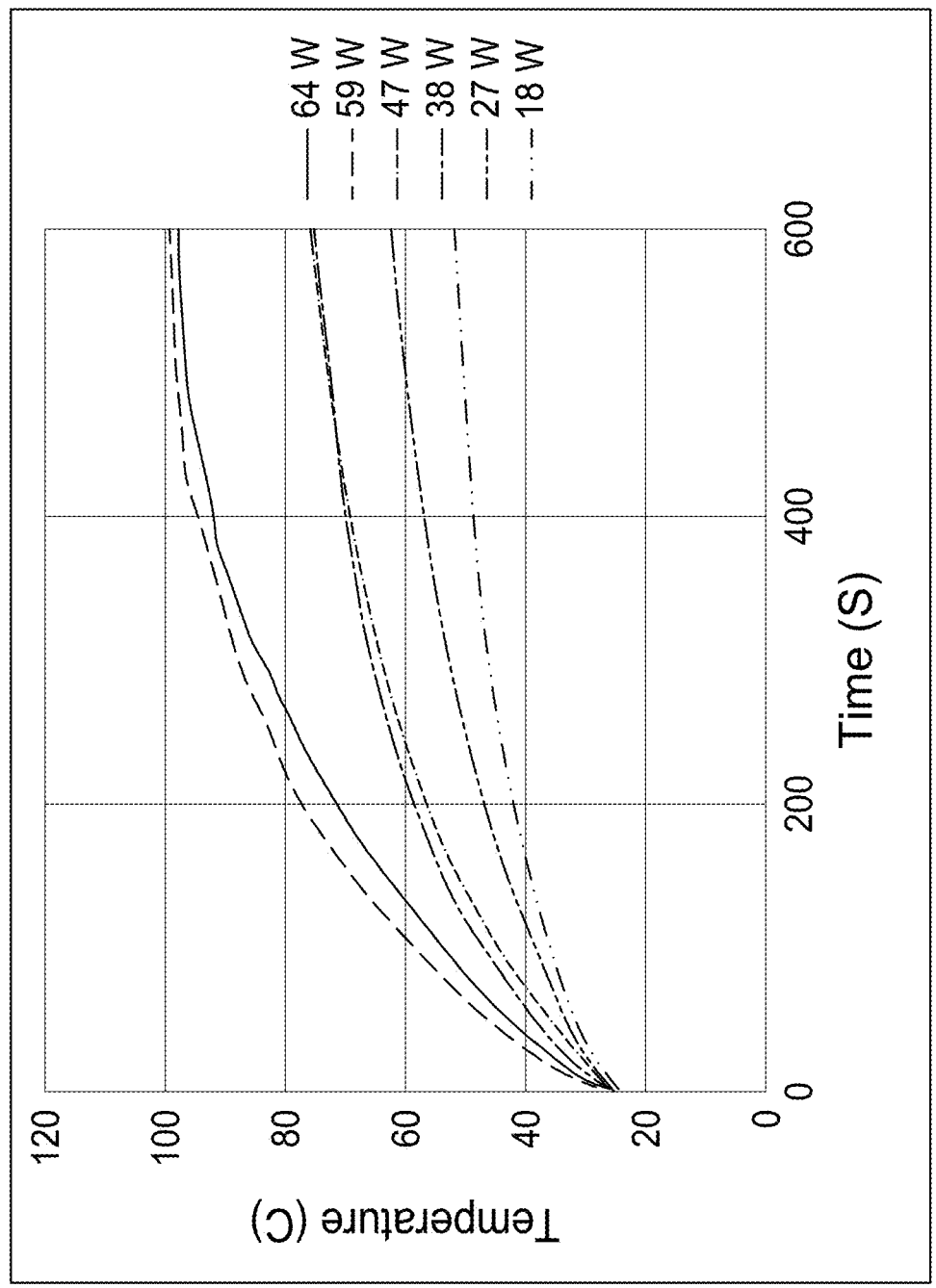
FIG. 12D illustrates the time required to reach a given temperature at a specific power.

FIG. 12A illustrates that the relationship between maximum temperature and acoustic energy followed a power law relationship versus intensity with time fixed, FIG. 12B illustrates a linear relationship versus time with power and intensity fixed, and FIG. 12C illustrates a linear relationship versus intensity at a fixed time. These preliminary trends can be configured to predict the energy, time, and intensity required to achieve desired temperatures. FIG. 12D further indicates the time required to reach a given temperature at a specific power.

In some examples, the jaw assembly 400 is configured to monitor the power that is reflected back as the ultrasound is passed through the target site. In some embodiments, the power reflected back can help the therapeutic ultrasound device 100 to determine the degree in which target site has been cauterized (e.g., sealed or cut). In some examples, this can be determined, over time, as tissue is being cauterized and the acoustic impedance changes. This change in impedance can affect the amount of power reflected back and sensed by the jaw assembly 400.

In some embodiments, the therapeutic ultrasound device 100 can sense (e.g., significant) change in the voltage standing wave ratio (VSWR) between the two transducers in the jaw assembly 400 as an indicator for ending of therapy, which is defined as complete ablation and hemostatic control. In vivo experiments were conducted in which the jaw assembly 400 was positioned on porcine kidneys which were instrumented with thermocouples. Therapy was administered until a significant change in VSWR was observed (average time of approximately 140 seconds). Upon resection of the distal portion of the kidney, no bleeding was observed (immediately after and for a 10-minute time frame) and the ablation plane was clearly and completely demarked. Furthermore, treatment times exceeding the VSWR inflexion point did not show excessive heating adjacent to the clamp heads. The results of these studies confirmed that VSWR is a potentially viable mechanism for determining end-of-treatment time thus ensuring robust ablation and hemostasis while at the same time avoiding overtreatment and possible collateral damage due to thermal spread.

Figure 13A:
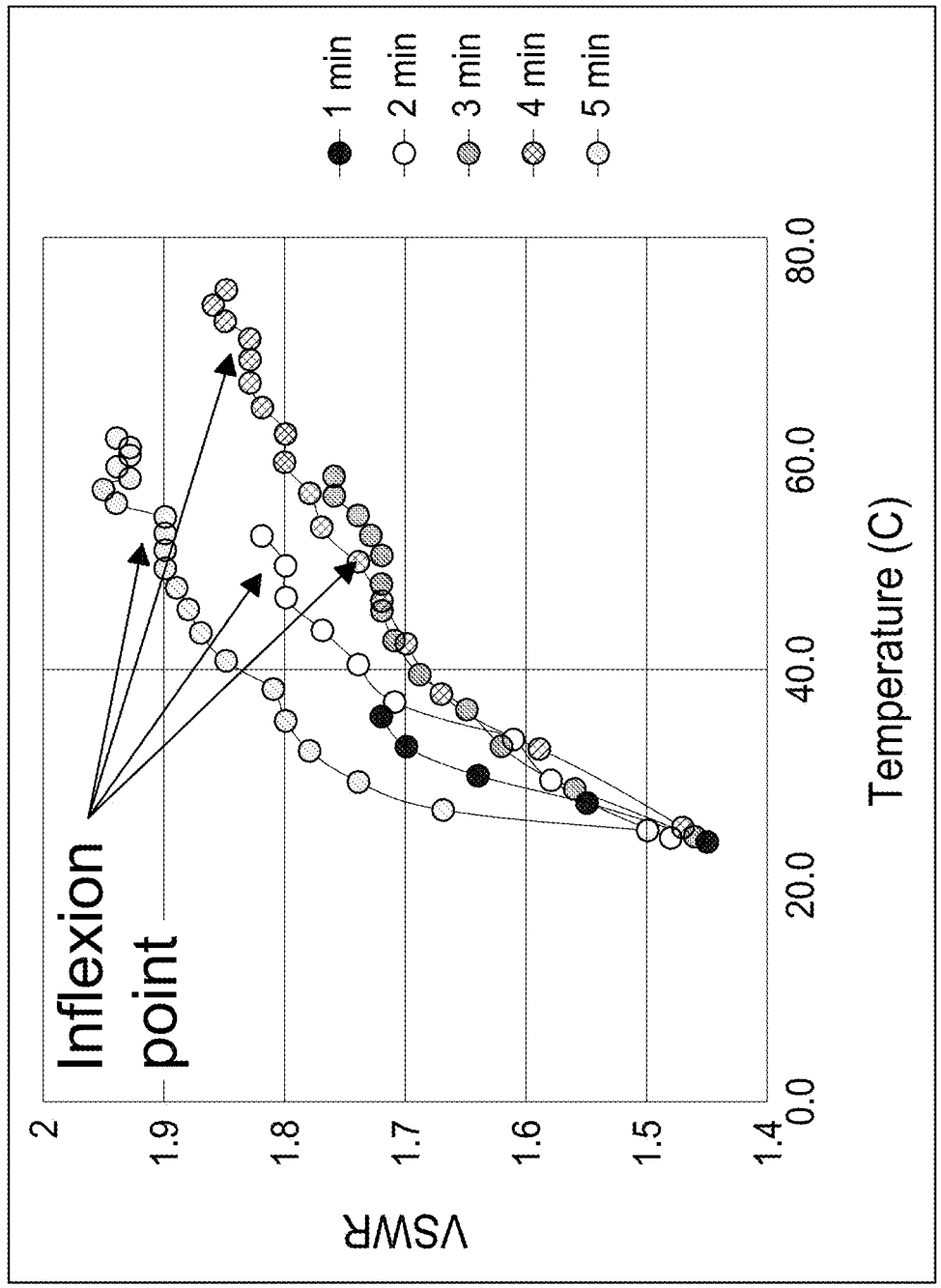
FIG. 13A-13D illustrate the use of the voltage standing wave ratio to determine end of treatment.
Figure 13B:
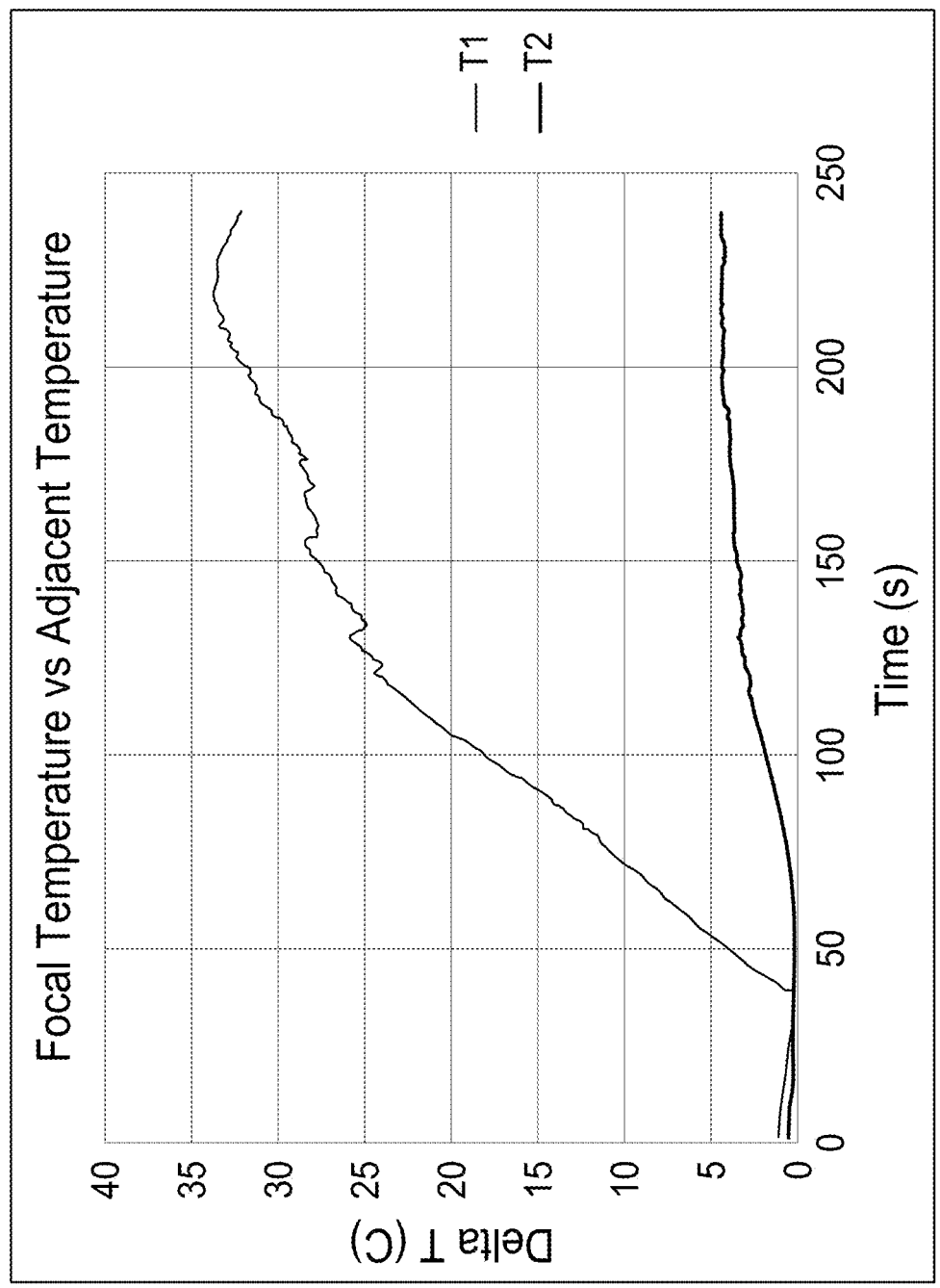
Figure 13C:
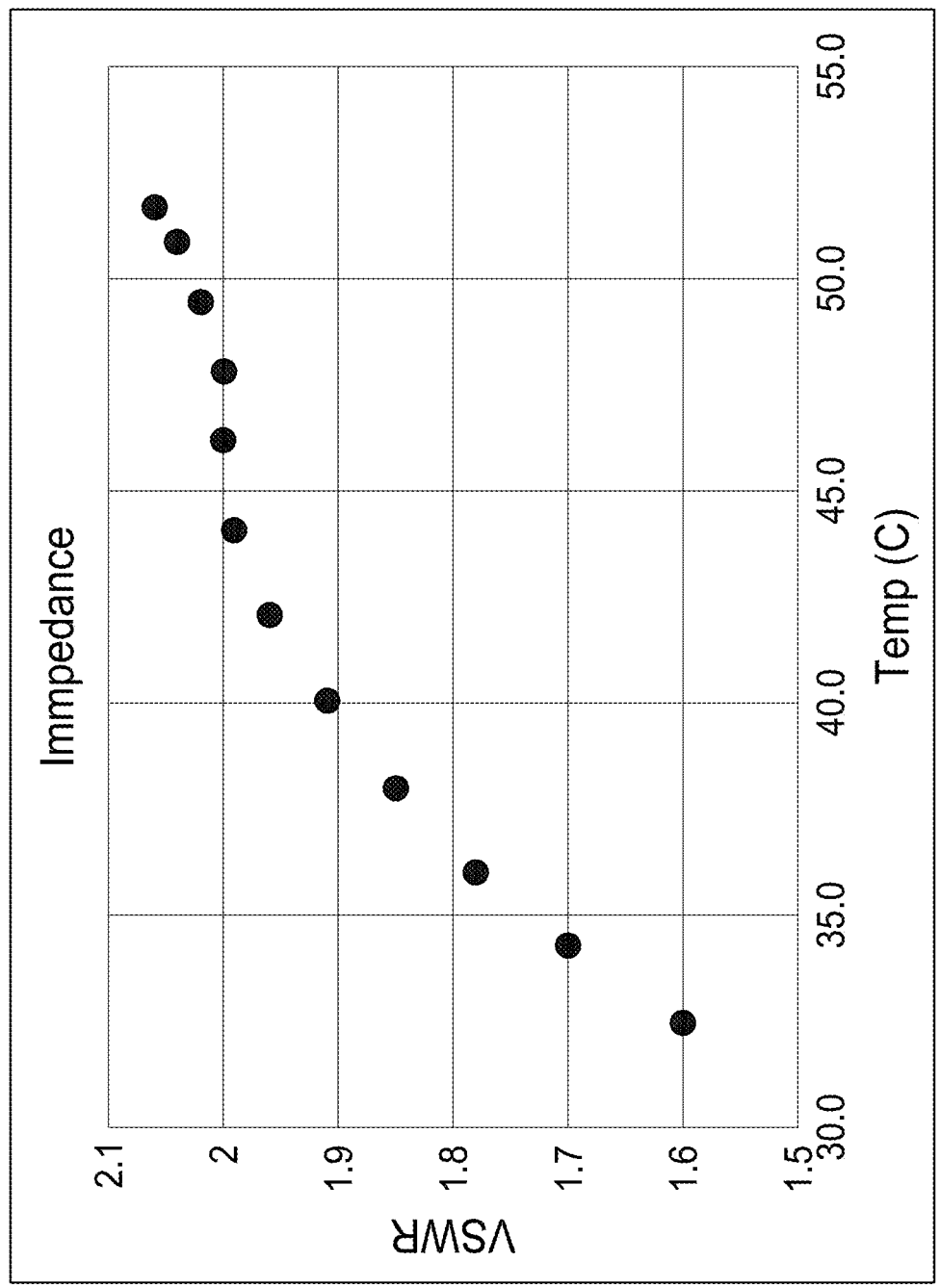
Figure 13D:
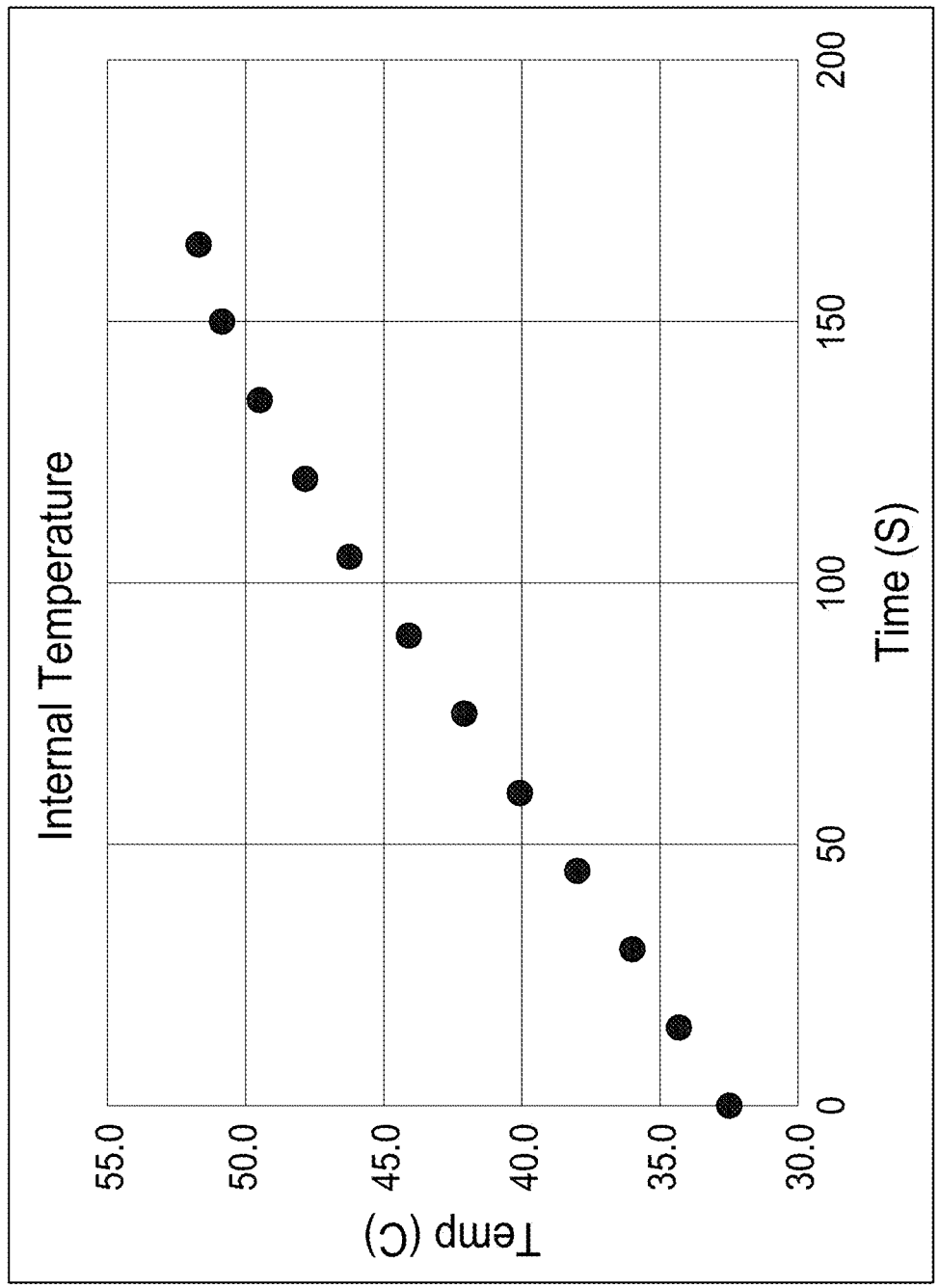

FIGS. 13A-13D illustrate the use of VSWR to determine end of treatment. Turning first to FIG. 13A, an inflection point is observed in treatments in which 43° C. was exceeded. FIG. 13B illustrates that extended treatments (e.g., 240 s) indicated a slight elevation in temperatures adjacent to the clamp as opposed to significant temperature increases in the focal region. FIG. 13C illustrates an example of where using the VSWR to determine the end of therapy in vivo results in complete hemostasis. Lastly, FIG. 13D illustrates that internal temperature reached approximately 50° C. at 140 s during in vivo experiments.

In some examples, in addition to the ultrasound generated by the transducer 600a, 600b, the force applied by the jaw assembly 400 can be effective in sealing and/or cutting the target tissue. In some embodiments, particularly with vessel sealing, there exists a relationship between the clamping force applied by the jaw assembly 400 and the power required. An example of the relationship is illustrated in FIG. 14. For example, when the clamping force applied by the jaw assembly 400 is too low, a higher energy from the transducer 600a, 600b is required and vice versa.

In some embodiments, as discussed above, the jaw assembly 400 can be configured to provide 10 lbs. of clamping force. In some embodiments, this can range between 10-14 lbs. of clamping force at the jaw assembly 400. In some embodiments, the clamping force at the jaw assembly 400 can be less than 10 lbs., between 10-11 lbs., between 11 lbs.-12 lbs., between 12 lbs.-13 lbs., between 13 lbs.-14 lbs., or greater than 14 lbs. In some embodiments, the clamping force at the jaw assembly 400 can be any of 10 lbs., 11 lbs., 12 lbs., 13 lbs., or 14 lbs. In order to generate the aforementioned clamping force in the jaw assembly 400—particularly when the top jaw 402 and the bottom jaw 404 have a width of only 3 mm-10 mm—sufficient force must be applied at the handle 120 of the therapeutic ultrasound device 100. In some embodiments, the ratio of the transfer of force is about 20:1. In some examples, the ratio of the transfer of force is between 15:1 to about 20:1; the ratio is 15:1, 16:1, 17:1, 18:1, 19:1, or 20:1; or the ratio is between 15:1 and 16:1, the ratio is between 16:1 and 17:1, the ratio is between 17:1 and 18:1, the ratio is between 18:1 and 19:1, or the ratio is between 19:1 and 20:1. In some embodiments, the ratio of the transfer of force satisfies the FDA requirement wherein 95% of the female population can actuate the therapeutic ultrasound device 100. In some examples, the combination of the pivot pin 460 and the angle and/or curvature of the slot 424 on the ears 420 of the pair of jaws 402, 404 are configured to increase the moment on the jaw assembly 400 to help increase the force generated at the jaw assembly 400.

Figure 10:
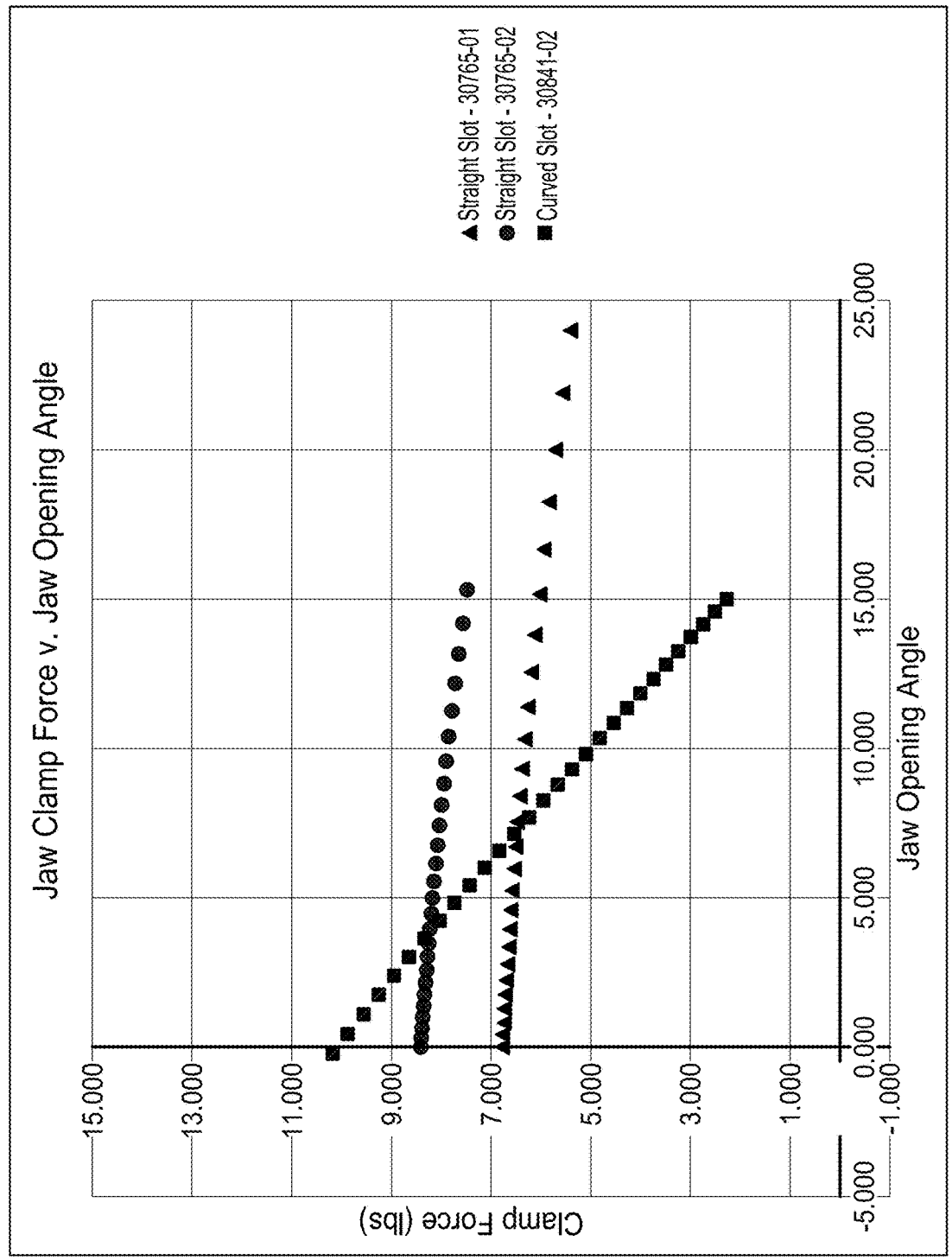
FIG. 10 illustrates the relationship between jaw clamp force over a range of jaw opening angles for straight and curved slots in the ears of the pair of jaws.

FIG. 10 illustrates the relationship between the clamping force generated by the jaw assembly 400 versus the jaw opening angle for a straight slot 424 compared to a curved slot 424 in the ears 420 of the pair of jaws 402, 404. As shown in FIG. 10, a straight slot 424 can provide a jaw clamp force that ranges between approximately 5.0 lbs. and 6.8 lbs. over a range of approximately 25 to 0 degrees. In another example, a straight slot 424 can provide a jaw clamp force that ranges between approximately 7.50 lbs. and 8.50 lbs. over a range of approximately 15 to 0 degrees. By comparison, a curved slot 424 can provide a jaw clamp force that ranges between 2 lbs. and 10 lbs. over a range of 15 to 0 degrees. As illustrated, a curved slot 424 can be configured to generate a moment to provide a greater jaw clamping force over a smaller range of angles.

In addition to the force applied by the jaw assembly 400 and the power generated by the transducer 600, the time in which the jaw assembly 400 is applied to the target tissue can affect whether the tissue and/or vessel is sealed or cut. In some embodiments the Energy to seal is a function of clamping pressure, acoustic power, and time:

$$E(s)=F(cp(t),ap(t))$$

In some embodiments, tissue and/or vessels can be sealed within approximately 2 seconds. In some examples, tissue and/or vessels can be cut within approximately 10 seconds. This time is in contrast to thermal or RF technology which requires approximately 10 to 25 seconds for comparable tissue. As well, use of ultrasound in the transducer 600 can provide for controlled tissue sealing and/or cutting within a very short time frame. In some examples, the transducer 600 can seal and/or cut tissue within 2 to 10 seconds, depending on the tissue. For example, a 5 mm vessel can be sealed using 100 Joules of acoustic energy. Similarly, the 5 mm vessel can be cut with an additional 50 Joules of acoustic energy. In some embodiments, a 5 mm vessel requires about 270 Joules to seal. In some examples, a 5 mm vessel requires about 640 Joules to divide. The amount of energy required will vary depending on tissue type and vessel size as well as the acoustic regime used to treat the target tissue.

Certain Terminology

Terms of orientation used herein, such as "top," "bottom," "horizontal," "vertical," "longitudinal," "lateral," and "end" are used in the context of the illustrated embodiment. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular" or "cylindrical" or "semi-circular" or "semi-cylindrical" or any related or similar terms, are not required to conform strictly to the mathematical definitions of circles or cylinders or other structures, but can encompass structures that are reasonably close approximations.

Conditional language, such as "can," "could," "might," or "may," unless specifically stated otherwise, or otherwise understood within the context as used, is generally intended to convey that certain embodiments include or do not include certain features, elements, and/or steps. Thus, such conditional language is not generally intended to imply that features, elements, and/or steps are in any way required for one or more embodiments.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

The terms "approximately," "about," and "substantially" as used herein represent an amount close to the stated amount that still performs a desired function or achieves a desired result. For example, in some embodiments, as the context may dictate, the terms "approximately," "about," and "substantially" may refer to an amount that is within less than or equal to 10% of the stated amount. The term "generally" as used herein represents a value, amount, or characteristic that predominantly includes or tends toward a particular value, amount, or characteristic. As an example, in certain embodiments, as the context may dictate, the term "generally parallel" can refer to something that departs from exactly parallel by less than or equal to 20 degrees.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A working in conjunction with a second processor configured to carry out recitations B and C.

The terms "comprising," "including," "having," and the like are synonymous and are used inclusively, in an open-ended fashion, and do not exclude additional elements, features, acts, operations, and so forth. Likewise, the terms "some," "certain," and the like are synonymous and are used in an open-ended fashion. Also, the term "or" is used in its inclusive sense (and not in its exclusive sense) so that when used, for example, to connect a list of elements, the term "or" means one, some, or all of the elements in the list.

Overall, the language of the claims is to be interpreted broadly based on the language employed in the claims. The language of the claims is not to be limited to the non-exclusive embodiments and examples that are illustrated and described in this disclosure, or that are discussed during the prosecution of the application.

Summary

Although various covers have been disclosed in the context of certain embodiments and examples (e.g., surgical assemblies and methods), this disclosure extends beyond the specifically disclosed embodiments to other alternative embodiments and/or uses of the embodiments and certain modifications and equivalents thereof. For example, any of the disclosed covers can be used on the leading edge of other types of devices, such as wings, vanes, blades, propellers, impellers, or otherwise. Various features and aspects of the disclosed embodiments can be combined with or substituted for one another in order to form varying modes of the conveyor. The scope of this disclosure should not be limited by the particular disclosed embodiments described herein.

Certain features that are described in this disclosure in the context of separate implementations can also be implemented in combination in a single implementation. Conversely, various features that are described in the context of a single implementation can also be implemented in multiple implementations separately or in any suitable sub-combination. Although features may be described above as acting in certain combinations, one or more features from a claimed combination can, in some cases, be excised from the combination, and the combination may be claimed as any sub-combination or variation of any sub-combination.

Moreover, while operations may be depicted in the drawings or described in the specification in a particular order, such operations need not be performed in the particular order shown or in sequential order, and all operations need not be performed, to achieve the desirable results. Other operations that are not depicted or described can be incorporated in the example methods and processes. For example, one or more additional operations can be performed before, after, simultaneously, or between any of the described operations. Further, the operations may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Some embodiments have been described in connection with the accompanying figures. The figures are drawn and/or shown to scale, but such scale should not be limiting, since dimensions and proportions other than what are shown are contemplated and are within the scope of the present disclosure. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, any methods described herein may be practiced using any device suitable for performing the recited steps.

In summary, various embodiments and examples of leading edge assemblies have been disclosed. Although the assemblies have been disclosed in the context of those embodiments and examples, this disclosure extends beyond the specifically disclosed embodiments to other alternative embodiments and/or other uses of the embodiments, as well as to certain modifications and equivalents thereof. This disclosure expressly contemplates that various features and aspects of the disclosed embodiments can be combined with, or substituted for, one another. Thus, the scope of this disclosure should not be limited by the particular disclosed embodiments described above, but should be determined only by a fair reading of the claims that follow.

What is claimed is:

1. A therapeutic ultrasound system for tissue engagement, the system comprising:
   a tissue engagement assembly having a width less than about 15 millimeters and configured to apply an engagement force to tissue at a target site, the tissue engagement assembly comprising:
      a first jaw and a second jaw, wherein each of the first jaw and the second jaw comprise:
         a body portion housing an acoustic stack, wherein the acoustic stack is configured to provide therapeutic ultrasound to the tissue at the target site, and
         an opening located at a proximal end of the body portion,
      wherein the first jaw and second jaw are located opposite of one another and are retained at the respective openings with a moveable fastener, such that the first jaw and the second jaw move relative to each other as the moveable fastener is moved in a first direction or a second direction.

2. The therapeutic ultrasound system of claim 1, wherein the first jaw and the second jaw of the tissue engagement assembly are configured to apply at least about 10 pounds of force to the tissue at the target site.

3. The therapeutic ultrasound system of claim 1, further comprising:
   a housing assembly attached to a proximal end of the tissue engagement assembly, wherein the housing assembly comprises a handle,
   wherein actuating the handle in a first direction is configured to move the moveable fastener in the first direction to reduce a distance between a distal end of the first jaw and a distal end of the second jaw, and
   wherein actuating the handle in a second direction is configured to move the moveable fastener in the second direction to increase a distance between the distal end of the first jaw and the distal end of the second jaw.

4. A therapeutic ultrasound apparatus comprising:
   a first jaw comprising:
      a first body portion having a width less than about 15 millimeters and housing an acoustic stack, wherein the acoustic stack is configured to generate therapeutic ultrasound, and
      a first opening located at a proximal end of the first body portion; and
   a second jaw opposite the first jaw, the second jaw comprising:
      a second body portion, and
      a second opening located at a proximal end of the second body portion,
   wherein the first jaw and the second jaw are retained at the first opening and the second opening with a fastener, such that the first jaw and the second jaw are configured to engage tissue,
   wherein an engagement force is applied to the tissue as the first jaw and the second jaw close, and
   wherein the therapeutic ultrasound generated by the acoustic stack is applied to the tissue as the first jaw and the second jaw close.

5. The therapeutic ultrasound apparatus of claim 4, wherein the second jaw houses an acoustic stack configured to generate therapeutic ultrasound.

6. The therapeutic ultrasound apparatus of claim 5 further comprising a bushing located between the proximal end of the first body portion of the first jaw and the proximal end of the second body portion of the second jaw, wherein the bushing prevents rotation of the first jaw relative to the second jaw.

7. The therapeutic ultrasound apparatus of claim 4, wherein the second jaw has a width less than about 15 millimeters.

8. The therapeutic ultrasound apparatus of claim 4, wherein at least one of the first jaw or the second jaw has a width less than about 15 millimeters and greater than about 3 millimeters.

9. The therapeutic ultrasound apparatus of claim 4, wherein the engagement force applied to the tissue comprises at least about 10 pounds of force.

10. The therapeutic ultrasound apparatus of claim 4, wherein at least one of the first jaw or the second jaw comprises at least one of stainless steel or ceramic.

11. The therapeutic ultrasound apparatus of claim 4, wherein the first body portion and the acoustic stack form an air pocket.

12. The therapeutic ultrasound apparatus of claim 4, wherein at least one of the first jaw or the second jaw includes a plurality of teeth configured to capture the tissue.

13. The therapeutic ultrasound apparatus of claim 12, wherein the plurality of teeth are formed at a distal end of the at least one of the first jaw or the second jaw.

14. The therapeutic ultrasound apparatus of claim 12, wherein the plurality of teeth comprise wave-like folds.

15. The therapeutic ultrasound apparatus of claim 12, wherein the plurality of teeth are located along a portion of the at least one of the first jaw or the second jaw.

16. The therapeutic ultrasound apparatus of claim 4, wherein the first jaw and the second jaw are configured to close in a scissor-like movement.

17. The therapeutic ultrasound apparatus of claim 4, wherein the first jaw and the second jaw are configured to close such that the first jaw and the second jaw remain in parallel with one another.

18. The therapeutic ultrasound apparatus of claim 4, wherein the first jaw and the second jaw are configured to close by moving relative to each other.

19. The therapeutic ultrasound apparatus of claim 4, wherein the first jaw and the second jaw are configured to close by moving only one of the first jaw or the second jaw.

20. A method of applying therapeutic ultrasound to tissue at a target site, the method comprising:
   guiding a tissue engagement assembly comprising a first jaw and a second jaw, wherein at least one of the first jaw or the second jaw comprise a body portion housing an acoustic stack configured to provide therapeutic ultrasound to the tissue at the target site;

actuating the tissue engagement assembly to engage the first jaw and the second jaw with the tissue at the target site;

applying engagement force to the tissue at the target site with the first jaw and the second jaw of the tissue engagement assembly;

providing the therapeutic ultrasound generated by the at least one acoustic stack to the tissue at the target site; and actuating the tissue engagement assembly to disengage the first jaw and the second jaw from the tissue at the target site.

21. The method of applying therapeutic ultrasound to a target tissue site of claim 20, wherein the therapeutic ultrasound that is provided to the tissue at the target site seals the tissue at the target tissue site.

22. The method of applying therapeutic ultrasound to a target tissue site of claim 20, wherein the therapeutic ultrasound that is provided to the tissue at the target site cuts the tissue at the target tissue site.

23. The method of applying therapeutic ultrasound to a target tissue site of claim 20, wherein the tissue engagement assembly has a width less than about 15 millimeters and greater than about 3 millimeters.

24. The method of applying therapeutic ultrasound to a target tissue site of claim 20, wherein the tissue engagement assembly is configured to apply at least about 10 pounds of engagement force to the tissue at the target site.

\* \* \* \* \*